(12) United States Patent
Johnson et al.

(10) Patent No.: US 11,028,183 B2
(45) Date of Patent: *Jun. 8, 2021

(54) HER2/NEU-SPECIFIC ANTIBODIES AND METHODS OF USING SAME

(71) Applicant: MacroGenics, Inc., Rockville, MD (US)

(72) Inventors: Leslie S. Johnson, Darnestown, MD (US); Ling Huang, Bethesda, MD (US); Nadine Tuaillon, Smithland, KY (US); Ezio Bonvini, Potomac, MD (US)

(73) Assignee: MacroGenics, Inc., Rockville, MD (US)

( * ) Notice: Subject to any disclaimer, the term of this patent is extended or adjusted under 35 U.S.C. 154(b) by 77 days.

This patent is subject to a terminal disclaimer.

(21) Appl. No.: 16/156,382

(22) Filed: Oct. 10, 2018

(65) Prior Publication Data

US 2019/0233539 A1    Aug. 1, 2019

Related U.S. Application Data

(60) Continuation of application No. 15/266,421, filed on Sep. 15, 2016, now Pat. No. 10,131,713, which is a continuation of application No. 14/994,892, filed on Jan. 13, 2016, now Pat. No. 9,469,692, which is a continuation of application No. 14/332,239, filed on Jul. 15, 2014, now Pat. No. 9,243,069, which is a division of application No. 12/933,885, filed as application No. PCT/US2009/038201 on Mar. 25, 2009, now Pat. No. 8,802,093.

(60) Provisional application No. 61/041,649, filed on Apr. 2, 2008.

(51) Int. Cl.
| C07K 16/32 | (2006.01) |
| A61K 39/395 | (2006.01) |
| A61K 45/06 | (2006.01) |
| A61K 39/00 | (2006.01) |

(52) U.S. Cl.
CPC ........ C07K 16/32 (2013.01); A61K 39/39558 (2013.01); A61K 45/06 (2013.01); A61K 2039/505 (2013.01); A61K 2039/54 (2013.01); C07K 2317/24 (2013.01); C07K 2317/51 (2013.01); C07K 2317/515 (2013.01); C07K 2317/71 (2013.01); C07K 2317/732 (2013.01); C07K 2317/92 (2013.01)

(58) Field of Classification Search
CPC ........ A61K 39/39558; A61K 2039/505; A61K 2039/54; C07K 16/32
USPC .................................................. 424/133.1
See application file for complete search history.

(56) References Cited

U.S. PATENT DOCUMENTS

| 4,179,337 A | 12/1979 | Davis et al. |
| 4,752,601 A | 6/1988 | Hahn |
| 5,024,835 A | 6/1991 | Rao et al. |
| 5,225,539 A | 12/1993 | Winter |
| 5,348,876 A | 9/1994 | Michaelson et al. |
| 5,576,184 A | 11/1996 | Better et al. |
| 5,585,089 A | 12/1996 | Queen et al. |
| 5,624,821 A | 4/1997 | Winter et al. |
| 5,648,260 A | 7/1997 | Winter et al. |
| 5,693,761 A | 12/1997 | Queen et al. |
| 5,693,762 A | 12/1997 | Queen et al. |
| 5,698,449 A | 12/1997 | Baumann et al. |
| 5,711,944 A | 1/1998 | Gilbert et al. |
| 5,723,584 A | 3/1998 | Schatz |
| 5,736,135 A | 4/1998 | Goeddel et al. |
| 5,736,137 A | 4/1998 | Anderson et al. |
| 5,837,243 A | 11/1998 | Deo et al. |
| 5,874,239 A | 2/1999 | Schatz |
| 5,877,396 A | 3/1999 | Ravetch et al. |
| 5,888,533 A | 3/1999 | Dunn |
| 5,945,115 A | 3/1999 | Dunn et al. |
| 5,932,433 A | 8/1999 | Schatz |
| 5,985,599 A | 11/1999 | Mckenzie et al. |
| 6,019,968 A | 2/2000 | Platz et al. |
| 6,025,485 A | 2/2000 | Kamb et al. |
| 6,114,147 A | 9/2000 | Frenken et al. |
| 6,132,764 A | 10/2000 | Li et al. |
| 6,132,992 A | 10/2000 | Ledbetter et al. |
| 6,165,745 A | 12/2000 | Ward et al. |
| 6,180,370 B1 | 1/2001 | Queen et al. |
| 6,194,551 B1 | 2/2001 | Idusogie et al. |
| 6,218,149 B1 | 4/2001 | Morrison et al. |

(Continued)

FOREIGN PATENT DOCUMENTS

| EP | 0 327 378 | 8/1989 |
| EP | 0 332 865 | 9/1989 |

(Continued)

OTHER PUBLICATIONS

US 6,331,391 B1, 12/2001, Wittrup et al. (withdrawn)

(Continued)

*Primary Examiner* — Lynn A Bristol
(74) *Attorney, Agent, or Firm* — William C. Schrot; Jeffrey I. Auerbach; AuerbachSchrot LLC

(57) ABSTRACT

This invention relates to antibodies that specifically bind HER2/neu, and particularly chimeric 4D5 antibodies to HER2/neu, which have reduced glycosylation as compared to known 4D5 antibodies. The invention also relates to methods of using the 4D5 antibodies and compositions comprising them in the diagnosis, prognosis and therapy of diseases such as cancer, autoimmune diseases, inflammatory disorders, and infectious disease.

38 Claims, 11 Drawing Sheets

Specification includes a Sequence Listing.

(56) References Cited

U.S. PATENT DOCUMENTS

| | | |
|---|---|---|
| 6,242,195 B1 | 6/2001 | Idusogie et al. |
| 6,277,375 B1 | 8/2001 | Ward |
| 6,300,065 B1 | 10/2001 | Kieke et al. |
| 6,339,069 B1 | 1/2002 | Meers et al. |
| 6,420,149 B1 | 7/2002 | Fukuda et al. |
| 6,423,538 B1 | 7/2002 | Wittrup et al. |
| 6,455,263 B2 | 9/2002 | Payan |
| 6,472,511 B1 | 10/2002 | Leung et al. |
| 6,528,624 B1 | 3/2003 | Idusogie et al. |
| 6,538,124 B1 | 3/2003 | Idusogie et al. |
| 6,548,640 B1 | 4/2003 | Winter |
| 6,696,550 B2 | 2/2004 | Larosa et al. |
| 6,737,056 B1 | 5/2004 | Presta |
| 6,800,738 B1 | 10/2004 | Carter et al. |
| 6,821,505 B2 | 11/2004 | Ward |
| 6,982,321 B2 | 1/2006 | Winter |
| 7,315,786 B2 | 1/2008 | Dahiyat et al. |
| 7,317,091 B2 | 1/2008 | Lazar et al. |
| 7,355,008 B2 | 4/2008 | Stavenhagen et al. |
| 7,371,379 B2 * | 5/2008 | Baughman .............. A61P 35/04 424/138.1 |
| 7,425,619 B2 | 9/2008 | Koenig et al. |
| 7,425,620 B2 | 9/2008 | Koenig et al. |
| 7,632,497 B2 | 12/2009 | Stavenhagen |
| 7,655,229 B2 | 2/2010 | Chan et al. |
| 7,662,925 B2 | 2/2010 | Lazar et al. |
| 7,662,926 B2 | 2/2010 | Chan et al. |
| 7,960,512 B2 | 6/2011 | Stavenhagen et al. |
| 8,187,593 B2 | 5/2012 | Koenig et al. |
| 8,193,318 B2 | 6/2012 | Koenig et al. |
| 8,802,093 B2 | 8/2014 | Johnson et al. |
| 9,096,877 B2 | 8/2015 | Johnson et al. |
| 9,243,069 B2 | 1/2016 | Johnson et al. |
| 9,469,692 B2 | 10/2016 | Johnson et al. |
| 2001/0036459 A1 | 11/2001 | Ravetch |
| 2002/0004587 A1 | 1/2002 | Miller et al. |
| 2002/0028486 A1 | 3/2002 | Morrison et al. |
| 2003/0077282 A1 | 4/2003 | Bigler et al. |
| 2003/0115614 A1 | 6/2003 | Kanda et al. |
| 2003/0158389 A1 | 8/2003 | Idusogie et al. |
| 2003/0190319 A1 | 10/2003 | Adolf et al. |
| 2003/0207346 A1 | 11/2003 | Arathoon et al. |
| 2004/0002587 A1 | 1/2004 | Watkins et al. |
| 2004/0110226 A1 | 6/2004 | Lazar et al. |
| 2004/0132101 A1 | 7/2004 | Lazar et al. |
| 2004/0185045 A1 | 9/2004 | Koenig et al. |
| 2004/0191244 A1 | 9/2004 | Presta |
| 2004/0220388 A1 | 11/2004 | Mertens et al. |
| 2004/0235065 A1 | 11/2004 | Hansen et al. |
| 2004/0236078 A1 | 11/2004 | Carter et al. |
| 2005/0025764 A1 | 2/2005 | Watkins et al. |
| 2005/0037000 A1 | 2/2005 | Stavenhagen et al. |
| 2005/0054832 A1 | 3/2005 | Lazar et al. |
| 2005/0064514 A1 | 3/2005 | Stavenhagen et al. |
| 2005/0090648 A1 | 4/2005 | Tsurushita et al. |
| 2005/0215767 A1 | 9/2005 | Koenig et al. |
| 2005/0260213 A1 | 11/2005 | Koenig et al. |
| 2006/0013810 A1 | 1/2006 | Johnson et al. |
| 2006/0018899 A1 | 1/2006 | Kao et al. |
| 2006/0024298 A1 | 2/2006 | Lazar et al. |
| 2006/0073142 A1 | 4/2006 | Chan et al. |
| 2006/0134709 A1 | 6/2006 | Stavenhagen et al. |
| 2006/0177439 A1 | 8/2006 | Koenig et al. |
| 2007/0004909 A1 | 1/2007 | Johnson et al. |
| 2007/0036799 A1 | 2/2007 | Stavenhagen et al. |
| 2007/0253948 A1 | 11/2007 | Chan et al. |
| 2008/0044417 A1 | 2/2008 | Johnson et al. |
| 2008/0050373 A1 | 2/2008 | Cohen et al. |
| 2008/0051563 A1 | 2/2008 | Lazar et al. |
| 2008/0131435 A1 | 6/2008 | Stavenhagen et al. |
| 2008/0138344 A1 | 6/2008 | Stavenhagen et al. |
| 2008/0138349 A1 | 6/2008 | Stavenhagen et al. |
| 2008/0286819 A1 | 11/2008 | Ravetch et al. |
| 2009/0053218 A1 | 2/2009 | Koenig et al. |
| 2012/0219551 A1 | 8/2012 | Johnson et al. |
| 2016/0257761 A1 * | 9/2016 | Koenig ................ A61K 9/0019 |
| 2018/0298100 A1 * | 10/2018 | Wigginton .......... C07K 16/2863 |

FOREIGN PATENT DOCUMENTS

| | | |
|---|---|---|
| EP | 0 629 703 | 12/1994 |
| EP | 0 359 096 | 11/1997 |
| EP | 0 953 639 | 11/1999 |
| EP | 1 006 183 | 6/2000 |
| EP | 0 343 950 | 10/2000 |
| WO | WO 1988/007089 | 9/1988 |
| WO | WO 1989/007142 | 8/1989 |
| WO | WO 1992/016562 | 10/1992 |
| WO | WO 1993/022332 | 11/1993 |
| WO | WO 1994/018330 | 8/1994 |
| WO | WO 1994/029351 | 12/1994 |
| WO | WO 1995/005468 | 2/1995 |
| WO | WO 1997/028267 | 8/1997 |
| WO | WO 1997/034631 | 9/1997 |
| WO | WO 1997/044362 | 11/1997 |
| WO | WO 1998/005787 | 2/1998 |
| WO | WO 1998/023289 | 6/1998 |
| WO | WO 1998/052975 | 11/1998 |
| WO | WO 1999/019362 | 4/1999 |
| WO | WO 1999/041285 | 8/1999 |
| WO | WO 1999/043713 | 9/1999 |
| WO | WO 1999/051642 | 10/1999 |
| WO | WO 1999/058572 | 11/1999 |
| WO | WO 2000/009560 | 2/2000 |
| WO | WO 2000/042072 | 7/2000 |
| WO | WO 2001/079299 | 10/2001 |
| WO | WO 2002/002781 | 1/2002 |
| WO | WO 2002/060919 | 8/2002 |
| WO | WO 2002/086070 | 10/2002 |
| WO | WO 2003/035835 | 5/2003 |
| WO | WO 2003/066095 | 8/2003 |
| WO | WO 2003/074679 | 9/2003 |
| WO | WO 2004/003019 | 1/2004 |
| WO | WO 2004/016750 | 2/2004 |
| WO | WO 2004/029207 | 4/2004 |
| WO | WO 2004/063351 | 7/2004 |
| WO | WO 2004/065423 | 8/2004 |
| WO | WO 2004/074455 | 9/2004 |
| WO | WO 2004/099249 | 11/2004 |
| WO | WO 2008/009545 | 1/2005 |
| WO | WO 2005/018669 | 3/2005 |
| WO | WO 2005/063815 | 7/2005 |
| WO | WO 2005/070963 | 8/2005 |
| WO | WO 2005/110474 | 11/2005 |
| WO | WO 2005/115452 | 12/2005 |
| WO | WO 2006/020114 | 2/2006 |
| WO | WO 2006/028956 | 3/2006 |
| WO | WO 2006/066078 | 6/2006 |
| WO | WO 2006/088494 | 8/2006 |
| WO | WO 2006/113665 | 10/2006 |
| WO | WO 2006/124886 | 11/2006 |
| WO | WO 2007/021841 | 2/2007 |
| WO | WO 2007/024249 | 3/2007 |
| WO | WO 2007/106707 | 9/2007 |
| WO | WO 2008/002933 | 1/2008 |
| WO | WO 2008/019199 | 2/2008 |
| WO | WO 2008/105886 | 9/2008 |
| WO | WO 2008/157379 | 12/2008 |
| WO | WO 2009/083009 | 7/2009 |
| WO | WO 2009/151717 | 9/2009 |
| WO | WO 2010/033279 | 3/2010 |

OTHER PUBLICATIONS

Stagg et al. (PNAS 108:7142-7147 (2011).*
Abra et al. The next generation of liposome delivery systems: recent experience with tumor-targeted, sterically-stabilized immunoliposomes and active-loading gradients. J Liposome Res. Feb.-May 2002;12(1-2):1-3.
Adams et al. (2004) A Single Treatment of Yttrium-90-labeled CHX-A"-C6.5 Diabody Inhibits the Growth of Established Human

(56) References Cited

OTHER PUBLICATIONS

Tumor Xenografts in Immunodeficient Mice, Cancer Research 64:6200-6206.
Alt et al., "Novel Tetravalent and Bispecific IgG-Like Antibody Molecules Combining Single-Chain Diabodies With the Immunoglobin Gamma 1 Fc or CH3 Region," FEBS Letters 454: 90-94, 1999.
Altman et al., "Phenotypic Analysis of Antigen-Specific T Lymphocytes", Science 274:94-96, 1996.
Amit et al. (1986) Three-dimensional structure of an antigen-antibody complex at 2.8 A resolution.; Science 233:747-753.
Angal et al., "A single amino acid substitution abolishes the heterogeneity of chimeric mouse/human (IgG4) antibody," Mol Immunol 30 :105-108, 1993.
Armour et al., "Differential binding to human FcgammaRIIa and FcgammaRIIb receptors by human IgG wildtype and mutant antibodies," Mol Immunol 40 :585-593, 2003.
Armour et al., "Recombinant human IgG molecules lacking Fcgamma receptor I binding and monocyte triggering activities," Eur J Immunol 29:2613-2624, 1999.
Armour et al., "The contrasting IgG-binding interactions of human and herpes simplex virus Fc receptors," Biochemical Society Transactions 30:495-500, 2002.
Armstrong, S. et al. "Heterogeneity of IgG1 monoclonal anti-Rh(D): an investigation using ADCC and macrophage binding assays," Brit. J. Haematol. 66:257-262 (1987).
Bachmann et al. (2005) "Recall Proliferation of Memory CD8+ T Cells and Antiviral Protection," J. Immunol. 175:4677-4685.
Baggiolini M, Dewald B. "Cellular models for the detection and evaluation of drugs that modulate human phagocyte activity," Experientia. Oct. 15;44(10):841-848, 1988.
Beckman et al. (2007) "Antibody Constructs in Cancer Therapy," Cancer 109(2):170-179.
Bendas G, Immunoliposomes: a promising approach to targeting cancer therapy. BioDrugs. 2001;15(4):215-24.
Bernard et al. (1986) "A unique epitope on the CD2 molecule defined by the monoclonal antibody 9-1: epitope-specific modulation of the E-rosette receptor and effects on T-cell functions," Hum. Immunol. 17(4):388-405.
Bewarder et al., 1996, "In vivo and in vitro specificity of protein tyrosine kinases for immunoglobulin G receptor (FcgammaRII) phosphorylation," Mol. Cell. Biol. 16 (9):4735-43.
Billadeau et al., ITAMs versus ITIMs: striking a balance during cell regulation, J Clin Invest. Jan. 2002;109(2):161-8.
Boder and Wittrup, "Optimal screening of surface-displayed polypeptide libraries," Biotechnol Prog 14:55-62, 1998.
Boder and Wittrup, "Yeast surface display for directed evolution of protein expression, affinity, and stability," Methods in Enzymology 328:430-444, 2000.
Boder and Wittrup, 1997, "Yeast surface display for screening combinatorial polypeptide libraries", Nature Biotechnology 15:553-557.
Boder et al., "Directed evolution of antibody fragments with monovalent femtomolar antigen-binding affinity," Proc. Natl. Acad. Sci. USA 97:10701-10705, 2000.
Bolland and Ravetch., Inhibitory pathways triggered by ITIM-containing receptors. Adv Immunol. 1999;72:149-177.
Bolland et al., Genetic modifiers of systemic lupus erythematosus in Fc.gamma RIIB(-/-) mice. J Exp Med. May 6, 2002;195(9):1167-74.
Boruchov et al., "Expression and Modulation of the Inhibitory Fcγ Receptor, FcγRIIB (CD32B), on Human Dendritic Cells (DCs)," Blood 102(11):Abstract #1908, 2003.
Boruchov et al., Activating and inhibitory IgG Fc receptors on human DCs mediate opposing. functions. The Journal of Clinical Investigation 115; 10:2914-2923.
Boyer et al. (1999) "Relative cytotoxic activity of immunotoxins reactive with different epitopes on the extracellular domain of the c-erbB-2 (HER-2/neu) gene product p185," Int. J. Cancer. 82(4):525-531.

Brauweiler et al., Partially distinct molecular mechanisms mediate inhibitory Fc.gamma.RIIB signaling in resting and activated B cells. J Immunol. 2001;167:204-211.
Bredius et al., "Role of neutrophil Fc gamma RIIa (CD32) and Fc gamma RIIIb (CD16) polymorphic forms in phagocytosis of human IgG1- and IgG3-opsonized bacteria and erythrocytes," Immunology 83:624-630, 1994.
Brekke et al., "Human IgG isotype-specific amino acid residues affecting complement-mediated cell lysis and phagocytosis.," Eur J Immunol 24:2542-2547, 1994.
Brown (2001) "Factors Modifying the Migration of Lymphocytes Across the Blood-Brain Barrier," Int Immunopharmacol. Nov. 2001;1(12):2043-62.
Brown EJ., "In Vitro Assays of Phagocytic Function of Human Peripheral Blood Leukocytes: Receptor Modulation and Signal Transduction," vol. 45 (Microbes as Tools for Cell Biology) in *Methods in Cell Biololgy*, Russell ed. Academic Press Inc. pp. 147-164, 1994.
Budde et al., Specificity of CD32 mAB for Fc.gamma.RIIa, Fc.gamma.RIIb1, and Fc.gamma.RIIb2 expressed in transfected mouse B cells and BHK-21 cells. Leukocyte Typing V: White cell differentiation antigens. 1995;828-832 (Schlossman, Boumsell, Gilks, Harlan, Kishomoto, eds.).
Burgess et al. (1990) "Possible dissociation of the heparin-binding and mitogenic activities of the heparin-binding (acidic fibroblast) growth factor-1 from its receptor binding activities by site directed mutagenesis of a single lysine residue," J. Cell Biol. 111:2129-2138.
Burmeister et al., "Crystal structure of the complex of rat neonatal Fc receptor with Fc," Nature 372:379-383, 1994.
Burton and Woof, "Human antibody effector function," Advances in Immunology 51:1-84, 1992.
Burton et al., "Molecular recognition of antibody (IgG) by cellular Fc receptor (FcRI)," Mol Immunol 25:1175-1181, 1988.
Burton, "Immunoglobulin G: functional sites," Mol Immunol 22:161-206, 1985.
Callanan et al., The IgG Fc Receptor, Fc.gamma.RIIB is a target for deregulation by chromosomal translocation in malignant lymphoma. PNAS. Jan. 2000;97(1):309-314.
Cameron et al., Differentiation of the human monocyte cell line, U937, with dibutyryl cyclicAMP induces the expression of the inhibitory Fc receptor, Fc.gamma.RIIb. Immunol Lett. Oct. 1, 2002;83(3):171-9.
Camilleri-Broet et al., Fc.gamma.RIIB is differentially expressed during B cell maturation and in B-cell lymphomas. Br J Haematol. 2004;124(1):55-62.
Campbell et al. (2003) "Monoclonal antibody therapy for lymphoma," Blood Rev. 17(3):143-152.
Canfield and Morrison, "The binding affinity of human IgG for its high affinity Fc receptor is determined by multiple amino acids in the CH2 domain and is modulated by the hinge region," J Exp Med 173:1483-1491, 1991.
Caron et al., "Engineered humanized dimeric forms of IgG are more effective antibodies," J Exp Med 176 :1191-5, 1992.
Carter et al., "Humanization of an anti-p185$^{HER2}$ antibody for human cancer therapy," Proc. Natl. Acad. Sci. USA 89:4285-4289, 1992.
Cartron et al., "Therapeutic activity of humanized anti-CD20 monoclonal antibody and polymorphism in IgG Fc receptor FcgammaRIIIa gene," Blood 99 :754-758, 2002.
Cassard et al., Modulation of tumor growth by inhibitory Fc.gamma. receptor expressed by human melanoma cells. The J Clin Invest. Nov. 2002;110(10):1549-1557.
Casset et al. (2003) A peptide mimetic of an anti-CD4 monoclonal antibody by rational design, Biochem. Biophs. Res. Commun. 307:198-205.
Cavacini et al. (1995) "Influence of heavy chain constant regions on antigen binding and HIV-1 neutralization by a human monoclonal antibody," J Immunol. 155(7):3638-3644.
Cespedes et al. (2006) "Mouse Models in Oncogenesis and Cancer Therapy," Clin. Transl. Oncol. 8(5):318-329.
Chappel et al., "Identification of a secondary Fc gamma RI binding site within a genetically engineered human IgG antibody," J. Biol. Chem. 268:25124-25131, 1993.

(56) References Cited

OTHER PUBLICATIONS

Chappel et al., "Identification of the Fc gamma receptor class I binding site in human IgG through use of recombinant IgG1/IgG2 hybrid and point-mutated antibodies," Proc. Natl. Acad. Sci USA 88:9036-9040, 1991.
Chattergee et al. (1994) "Idiotypic Antibody Immunotherapy of Cancer," Cancer Immuno. Immunother. 38:75-82.
Chen, et al. (1999) "Selection and Analysis of an Optimized Anti-VEGF Antibody: Crystal Structure of an Affinity-Matured Fab in Complex with Antigen," J. Molec. Biol. 293:865-881.
Chen, Y. et al. (1999) "Selection and Analysis of an Optimized Anti-VEGF Antibody: Crystal Structure of an Affinity-Matured Fab in Complex with Antigen," J. Mol. Biol. 293:865-881.
Ciccimarra et al., "Localization of the IgG effector site for monocyte receptors," Proc. Natl. Acad. Sci. U.S.A. 72 :2081-2083, 1975.
Clynes and Ravetch, "Cytotoxic antibodies inflammation through Fc receptors," Immunity 3:21-26, 1995.
Clynes et al., "Fc receptors are required in passive and active immunity to melanoma," Proc. Natl. Acad Sci USA 95:652-656, 1998.
Clynes et al., "Inhibitory Fc receptors modulate in vivo cytoxicity against tumor targets," Nature Medicine 6 :443-446, 2000.
Clynes et al., "Modulation of immune complex-induced inflammation in vivo by the coordinate expression of activation and inhibitory Fc receptors," J Exp Med 189:179-185, 1999.
Clynes et al., "Uncoupling of immune complex formation and kidney damage in autoimmune glomerulonephritis," Science 279:1052-1054, 1998.
Cobleigh et al. (1999) Multinational Study of the Efficacy and Safety of Humanized Anti-HER2 Monoclonal Antibody in Women Who Have HER2-Overexpressing Metastatic Breast Cancer That Has Progressed After Chemotherapy for Metastatic Disease, J Clin Oncol 17(9):2639-2648.
Colman, P.M. (1994) "Effects of amino acid sequence changes on antibody-antigen interactions," Res. Immunol. 145:33-36.
Daeron (1997) "Fc Receptor Biologoy" Annu Rev. Immunol. 15:203-34.
Daeron et al., The Same Tyrosine Based Inhibition Motif, in the Intracytoplasmic Domain of Fc.gamma.RIIB, regulates negatively BCR, TCR- and FcR dependent cell activation. Immunity. Nov. 1995;3: 635-646.
Damle et al., B-cell chronic lymphocytic leukemia cells express a surface membrane phenotype of activated, antigen-experienced B lymphocytes. Blood Jun. 1, 2002;99(11):4087-4093.
Davies et al. (1995) Antibody Vh domains as small recognition units, Bio/Technology 13:475-479.
Davies et al., Expression of GnTIII in a recombinant anti-CD20 CHO production cell line: Expression of antibodies with altered glycoforms leads to an increase in ADCC through higher affinity for Fc.sub..gamma RIII. Biotechnol Bioeng. Aug. 20, 2001;74(4):288-94.
De Haas, Wien Kin "IgG-Fc receptors and the clinical relevance of their polymorphisms," Wien Klin Wochenscha 113:825-831, 2001.
De Pascalis et al., (2002) "Grafting of "Abbreviated" Complementarity-Determining Regions Containing Specificity-Determining Residues Essential for Ligand Contact to Engineer a Less Immunogenic Humanized Monoclonal Antibody," J. Immunol. 169:3076-3084.
De Santes et al. (1992) "Radiolabeled Antibody Targeting of the Her-2/neu Oncoprotein," Cancer Res. 52:1916-1923.
Dennis, C. (2006) "Cancer: Off by a Whisker," Nature 442:739-741.
Ding et al., Inhibition of the function of the Fc.gamma.RIIB by a monoclonal antibody to thymic shared antigen-1, a Ly-6 family antigen. Immunology. Sep. 2001;104(1):28-36.
Dumoulin et al. (2002) Single-domain antibody fragments with high conformational stability, Protein Science 11:500-512.
Duncan and Winter, "Localization of the binding site for the human high-affinity Fc receptor on IgG," Nature 332:563-564, 1998.
Duncan and Winter, "The binding site for C1q on IgG," Nature 332 :738-740, 1988.

Edberg et al., "Modulation of Fcgamma and Complement Receptor Function by the Glycosyl-Phosphatidylinositol-Anchored Form of FcgammaRIII," Journal of Immunology 152: 5826-5835, 1994.
Efferson et al. (2005) "Stimulation of Human T Cells by an Influenza A Vector Expressing a CTL Epitope from the HER-2/neu Protooncogene Results in Higher Numbers of Antigen Specific TCRhi Cells than Stimulation with Peptide," Anticancer Research 25:715-724.
Eigenbrot et al. (1993) "X-ray Structures of the Antigen-binding Domains from Three Variants of Humanized anti-p185$^{HER2}$ Antibody 4D5 and Comparison with Molecular Modeling," J. Mol. Biol. 229(4):969-995.
Ellman, J et al. "Biosynthetic Method for Introducing Unnatural Amino Acids Site-Specifically into Proteins," Methods Enzymol. 202:301-336, 1991.
Eppstein et al., Biological activity of liposome-encapsulated murine interferon .gamma. is mediated by a cell membrane receptor. Proc Natl Acad Sci U S A. Jan. 1985;82(11):3688-9.
European Search Report (EP 05778285) dated Apr. 14, 2008.
Extended Search Report EP 05854332.2 (PCT/US2005/045586) (2009).
Extended Search Report EP 05857521.8 (WO 06/088494) (2009).
Extended Search Report EP 07758130.4 (PCT/US2007/063548) (2009).
Extended Search Report EP 07812341.1 (PCT/US2007/72153) (2009) (9 pages).
Extended Search Report EP 07873826.7 (PCT/US2007/069767) (2009) 8 pages).
Extended Search Report EP07799049 (PCT/US2007/072151) (2010) (7 pages).
Fanger et al., Production and use of anti-FcR bispecific antibodies. Immunomethods. Feb. 1994;4(1):72-81.
Farag, et al., Fc.gamma.RIIIa and Fc.gamma.RIIIa polymorphisms do not predict response to Rituximab in B-cell chronic lymphocytic leukemia. Blood. Oct. 16, 2003 (15 pp.).
Fidler, I. J., Macrophages and metastasis—a biological approach to cancer therapy. Cancer Res. Oct. 1985;45(10):4714-26.
Fleit et al., 1995 "Cross-linking of mAb to Fc.gamma.RII results in tyrosine phosphorylation of multiple polypeptides including FC.gamma. RII itself." Leukocyte Typing V: White cell differentiation antigens 826-827 (Schlossman, Boumsell, Gilks, Harlan, Kishomoto, eds.).
Flesch and Neppert, "Functions of the Fc receptors for immunoglobulin G," J Clin Lab Anal 14:141-156, 2000.
Fujimori et al. (1990) "A Modeling Analysis of Monoclonal Percolation Through Tumors: a Binding-Site Barrier," J. Nucl. Med. 31(7):1191-1198.
Gamberale et al., 2003, "To the Editor: Expression of Fc.gamma. receptors type II (Fc.gamma.RIII) in chronic lymphocytic leukemia B cells." Blood (Correspondence) 102(7):2698-2699.
Gerber et al., Stimulatory and inhibitory signals originating from the macrophage Fc.gamma. receptors. Microbes Infect. Feb. 2001;3(2):131-9.
Gergeley et al., "Fc receptors on lymphocytes and K cells," Biochemical Society Transactions 12:739-743, 1984.
Gergely and Sarmay, "The two binding-site models of human IgG binding Fc gamma receptors," FASEB J 4:3275-3283, 1990.
Greenwood and Clark, Effector functions of matched sets of recombinant human IgG subclass antibodies. (final version edited Feb. 11, 1993).
Greenwood et al., "Engineering multiple-domain forms of the therapeutic antibody CAMPATH-1H: effects on complement lysis," Therapeutic Immunology 1:247-255, 1994.
Horton, J. (2002) Trastuzumab Use in Breast Cancer: Clinical Issues, Cancer Control 9(6):499-507.
Greenwood et al., "Structural motifs involved in human IgG antibody effector functions," Eur J Immunol 23:1098-1104, 1993.
Gura (1997) "Systems for Identifying New Drugs Are Often Faulty," Science 278:1041-1042.
Hadley et al., "The functional activity of Fc gamma RII and Fc gamma RIII on subsets of human lymphocytes," Immunology 76:446-451, 1992.

(56) References Cited

OTHER PUBLICATIONS

Hatta et al., "Association of Fc gamma receptor IIIB, but not of Fc gamma receptor IIA and IIIA polymorphisms with systemic lupus erythematosus in Japanese," Genes and Immunity 1:53-60, 1999.
Hayes, Fc Engineering to Enhance Monoclonal Antibody Effector Functions. (Presentation) Xecor, CA, 2003.
Henry et al. (2004) "A prostate-specific membrane antigen-targeted monoclonal antibody-chemotherapeutic conjugate designed for the treatment of prostate cancer," Cancer Res. 64(21):7995-8001.
Herzenberg et al., "The history and future of the fluorescence activated cell sorter and flow cytometry: a view from Stanford," Clinical Chem. 2002:48:1819-1827, 2002.
Heyman, "Regulation of antibody responses via antibodies, complement, and Fc receptors," Annu Rev Immunol 18:709-737, 2000.
Hogarth et al., "Characterization of FcR Ig-binding sites and epitope mapping," Immunomethods 4 :17-24, 1994.
Holler et al., "In vitro evolution of a T cell receptor with high affinity for peptide/MHC," Proc. Natl. Acad. Sci. U.S.A. 97 :5387-92, 2000.
Holliger, P. (1993) "Diabodies: Small bivalent and bispecific antibody fragments," Proc. Natl. Acad. Sci. (U.S.A.) 90(14):6444-6448.
Holm et al, (2007) "Functional Mapping and Single Chain Construction of the Anti-Cytokeratin 8 Monoclonal Antibody TS1," Molecular Immunology 44:1075-1084.
Holmes et al., Alleles of the Ly-17 alloantigen define polymorphisms of the murine IgG Fc receptor. Proc Natl Acad Sci USA. Nov. 1985;82(22):7706-10.
Holt, L.J. (2003) "Domain Antibodies: Proteins for Therapy," TRENDS in Biochemistry 21(11)484-490.
Hulett et al., "Chimeric Fc receptors identify functional domains of the murine high affinity receptor for IgG," J Immunol 147 :1863-1868, 1991.
Hulett et al., "Identification of the IgG binding site of the human low affinity receptor for IgG Fc gamma RII. Enhancement and ablation of binding by site-directed mutagenesis," J. Biol. Chem. 269:15287-15293, 1994.
Hulett et al., "Multiple regions of human Fc gamma RII (CD32) contribute to the binding of IgG," J. Biol. Chem. 270:21188-21194, 1995.
Hwang et al., Hepatic uptake and degradation of unilamellar sphingomyelin/cholesterol liposomes: a kinetic study. Proc Natl Acad Sci U S A. Jul. 1980;77(7):4030-4.
Hynes and Stern (1994) "The biology of erbB-2/neu/HER-2 and its role in cancer," Biochim. et Biophys. Acta 1198:165-184.
Ibragimova et al. (1999) "Stability of the beta-sheet of the WW domain: A molecular dynamics simulation study," Biophys. J. 77(4):2191-2198.
Idusogie et al., "Engineered antibodies with increased activity to recruit complement," J Immunol 166 :2571-2575, 2001.
Idusogie et al., "Mapping of the C1q binding site on rituxan, a chimeric antibody with a human IgG1 Fc," J Immunol 164: 4178-4184, 2000.
International Preliminary Report on Patentability PCT/US04/000643 (WO04/063351) (2005).
International Preliminary Report on Patentability PCT/US05/024645(WO06/088494) (2007).
International Preliminary Report on Patentability PCT/US05/12798 (WO06/088494) (2005).
International Preliminary Report on Patentability PCT/US06/031201(WO07/021841) (2008).
International Preliminary Report on Patentability PCT/US07/069767 (WO08/105886) (2008)(7 pages).
International Preliminary Report on Patentability PCT/US07/086793 (WO08/140603) (2008).
International Preliminary Report on Patentability PCT/US07/72153 (WO08/019199) (2008).
International Search Report; PCT/US04/000643 (WO04/063351) (2004).
International Search Report; PCT/US05/024645 (WO06/088494) (2007).
International Search Report; PCT/US05/12798 (WO06/088494) (2005).
International Search Report; PCT/US06/031201 (WO07/021841) (2008).
International Search Report; PCT/US07/069767 (WO08/105886) (2008) (4pages).
International Search Report; PCT/US07/086793 (WO08/140603) (2008).
International Search Report; PCT/US07/72153 (WO08/019199) (2008).
International Search Report; PCT/US09/38171 (dated Mar. 24, 2010)(12 pages).
International Search Report; PCT/US09/38201 (WO09/123894) (2009) (11 pages).
Isaacs et al., "A therapeutic human IgG4 monoclonal antibody that depletes target cells in humans," Clin Exp Immunol 106 :427-433, 1996.
Isaacs et al., "Therapy with monoclonal antibodies. An in vivo model for the assessment of therapeutic potential," J Immunol 148 :3062-3071, 1992.
Isaacs et al., "Therapy with monoclonal antibodies. II. The contribution of Fc gamma receptor binding and the influence of C(H)1 and C(H)3 domains on in vivo effector function," J Immunol 161 :3862-3869, 1998.
Jain et al. "Barriers to Drug Delivery in Solid Tumors," Scientific American Jul. 1994:58-65.
Jassal et al., "Remodeling glycans on IgG by genetic re-engineering," Biochem Soc Trans 26 :S113, 1998.
Jefferis and Lund, "Interaction sites on human IgG-Fc for Fcgam-maR: current models," Immunology Letters 82 :57-65, 2002.
Jefferis et al., "IgG-Fc-mediated effector functions: molecular definition of interaction sites for effector ligands and the role of glycosylation," Immunol Rev 163:59-76, 1998.
Jefferis et al., "Molecular definition of interaction sites on human IgG for Fc receptors (huFc gamma R)," Mol Immunol 27 :1237-1240, 1990.
Jefferis et al., "Recognition sites on human IgG for Fc gamma receptors: the role of glycosylation," Immunol Lett 44 :111-7, 1995.
Jendeberg et al., "Engineering of Fc(1) and Fc(3) from human immunoglobulin G to analyse subclass specificity for staphylococcal protein A," J Immunological Methods 201 :25-34, 1997.
Jiang et al. (Epub Nov. 9, 2004) "A novel peptide isolated from a phage display peptide library with trastuzumab can mimic antigen epitope of HER-2," J Biol Chem. 280(6):4656-4662.
Kadar et al., "Modulatory effect of synthetic human IgG Fc peptides on the in vitro immune response of murine spleen cells," Int J Immunpharmacol 13 :1147-55, 1991.
Kadar et al., "Synthetic peptides comprising defined sequences of CH-2 and CH-3 domains of human IgG1 induce prostaglandin E2 production from human peripheral blood mononuclear cells," Immunol Lett 32:59-63, 1992.
Kagari et al., Essential Role of Fc.gamma. Receptors in anti-type II collagen antibody induced arthritis. J. Immunol. Apr. 2003;170:4318-24.
Kang, C.Y. et al. (1988) "Inhibition of Self-Binding Antibodies (Autobodies) by a VH-Derived Peptide," Science 240(4855):1034-1036.
Kato et al., "Structural basis of the interaction between IgG and Fcγ receptors," J Mol Biol 295:213-224, 2000.
Keler et al., "Differential effect of cytokine treatment on Fc alpha receptor I- and Fc gamma receptor I-mediated tumor cytotoxicity by monocyte-derived macrophages," J. of Immunol. 164:5746-52, 2000.
Kepley et al. "Co-aggregation FcgammaRII with FcepsilonRI on human mast cells inhibits antigeninduced secretion and involves SHIP-Grb2-Dok complexes" J. Biol. Chem. 279(34) 35139-35149.
Kieke et al., "Selection of functional T cell receptor mutants from a yeast surface-display library," Proc. Natl. Acad. Sci. U.S.A. 96 :5651-56, 1999.
Kim et al. (2002) "Both the epitope specificity and isotype are important in the antitumor effect of monoclonal antibodies against Her-2/neu antigen," Int. J. Cancer. 102(4):428-434.

(56) References Cited

OTHER PUBLICATIONS

Kim et al., "Analysis of FγyRIII and IgG Fc polymorphism reveals functional and evolutionary implications of protein-protein interaction," J Mol Evol 53:1-9, 2001.
Kimura et al. (1981) "A new mouse cell-surface antigen (Ly-m20) controlled by a gene linked to Mls locus and defined by monoclonal antibodies," Immunogenetics. 14(1-2):3-14.
Kipps et al. (1985) "Importance of Immunoglobin Isotype in Human Antibody-Dependent, Cell-Mediated Cytotoxicity Directed by Murine Monoclonal Antbodies," J. Exper. Med. 161:1-17.
Klein et al., "Expression of biological effector functions by immunoglobulin G molecules lacking the hinge region," Proc. Natl. Acad. Sci. U.S.A. 78 :524-528, 1981.
Koene et al., "Fc gammaRIIIa-158V/F of the polymorphism influences the binding of IgG by natural killer cell Fc gammaRIIIa, independently of the Fc gammaRIIIa-48L/R/H phenotype," Blood 90 :1109-1114, 1997.
Kranz et al., "Mechanisms of ligand binding by monoclonal anti-fluorescyl antibodies," J. Biol. Chem. 257:6987-6995, 1982.
Kumar et al. (1991) "Regulation of phosphorylation of the c-erbB-2/HER2 gene product by a monoclonal antibody and serum growth factor(s) carcinoma cells," Mol. Cell. Biol. 11(2):979-986.
Kumpel, B.M. Brit. "Human monoclonal anti-D antibodies," J. Haematol. 71:415-420 (1989).
Kurlander et al., 1986, "Comparison of intravenous gamma globulin and a monoclonal anti-Fc receptor antibody as inhibitors of immune clearance in vivo in mice." J. Clin. Invest. 77(6):2010-2018.
Lazar et al. (1988) Transforming growth factor a: mutation of aspartic acid 47 and leucine 48 results in different biological activities, Molec. Cell. Biol. 8:1247-1252.
Le Gall, F. et al. (Epub May 4, 2004) "Effect of Linker Sequences Between the Antibody Variable Domains on the Formation, Stability and Biological Activity of a Bispecific Tandem Diabody," Protein Eng Des Sel. 17(4):357-366.
Lee et al. (1995) "Requirement for neuregulin receptor erbB2 in neural and cardiac development," Nature 378:394-398.
Lehmann et al., "Phagocytosis: measurement by flow cytometry," J Immunol Methods. 243(1-2):229-42, 2000.
Lehrnbecher et al., "Variant genotypes of the low-affinity Fcgamma receptors in two control populations and a review of low-affinity Fcgamma receptor polymorphisms in control and disease populations," Blood 94:4220-4232, 1999.
Lewis et al. (1993) "Differential responses of human tumor cell lines to anti-p185HER2 monoclonal antibodies," Cancer Immunol Immunother. 37(4):255-263.
Li et al. (2007) Regeneration of nigrostriatal dopaminergic axons by degradation of chondroitin sulfate is accompanied by elimination of the fibrotic scar and glia limitans in the lesion site. J. Neurosci. Res. 85:636-547.
Li et al., "Reconstitution of human Fc gamma RIII cell type specificity in transgenic mice," J Exp Med 183 :1259-1263, 1996.
Lifely et al., Glycosylation and biological activity of CAMPATH-1H expressed in different cell lines and grown under different culture conditions. Glycobiology. Dec. 1995;5(8):813-22.
Lin et al., Colony-stimulating factor 1 promotes progression of mammary tumors to malignancy. J Exp Med. 2001;193(6):727-739.
Lin et al., The macrophage growth factor CSF-1 in mammary gland development and tumor progression. J Mammary Gland Biol Neoplasia. 2002;7(2):147-62.
Liu et al., "Production of a mouse-human chimeric monoclonal antibody to CD20 with potent Fc-dependent biologic activity," J. Immunol. 139:3521-3526, 1987.
Looney et al., 1986, "Human Monocytes and U(#& Cells Bear Two Distinct Fc Receptors for IgG." J. Immunol. 136(5):1641-1647.
Lu et al. (2004) "The effect of variable domain orientation and arrangement on the antigen-binding activity of a recombinant human bispecific diabody," doi:1'0.1016/j./bbre.2004.04.060.
Lu, D. et al. (2003) "Di-Diabody: A Novel Tetravalent Bispecific Antibody Molecule by Design. " J. Immunol. Meth. 279: 219-232.

Lund et al., "Expression and characterization of truncated forms of humanized L243 IgG1. Architectural features can influence synthesis of its oligosaccharide chains and affect superoxide production triggered through human Fcgamma receptor I," Eur J Biochem 267 :7246-57, 2000.
Lund et al., "Human Fc gamma RI and Fc gamma RII interact with distinct but overlapping sites on human IgG," Immunol 147 :2657-62, 1991.
Lund et al., "Multiple binding sites on the CH2 domain of IgG for mouse Fc gamma R11," Molecular Immunology 29:53-59, 1992.
Lund et al., "Multiple interactions of IgG with its core oligosaccharide can modulate recognition by complement and human Fc gamma receptor I and influence the synthesis of its oligosaccharide chains," J Immunol 157 :4963-4969, 1996.
Lund et al., "Oligosaccharide-protein interactions in IgG can modulate recognition by Fc gamma receptors," FASEB J 9 :115-119, 1995.
Lyden et al., The Fc receptor for IgG expressed in the villus endothelium of human placenta is Fc.gamma. RIIb2. J Immunol. Mar. 15, 2001;166(6):3882-9.
MacCallum et al. (1996) "Antibody-Antigen Interactions: Contact Analysis and Binding Site Topography," J. Molec. Biol. 262:732-745.
Maenaka et al., "The human low affinity Fcgamma receptors IIa, IIb, and III bind IgG with fast kinetics and distinct thermodynamic properties," J Biol Chem 48 :44898-904, 2001.
Malbec et al., Fcs receptor I-associated lyn-dependent phosphorylation of Fc.gamma. receptor IIB during negative regulation of mast cell activation. J Immunol. Feb. 15, 1998;160(4):1647-58.
Maresco et al., 1999, "The SH2-Containing 5'-Inositol Phosphatase (SHIP) Is Tyrosine Phosphorylated after Fc.gamma. Receptor Clustering in Monocytes." J. Immunol. 162:6458-6465.
Maruyama K, In vivo targeting by liposomes. Biol Pharm Bull. Jul. 2000;23(7):791-9.
Masui et al. (1986) "Mechanism of antitumor activity in mice for anti-epidermal growth factor receptor monoclonal antibodies with different isotypes.," Canc. Res. 46:5592-5598.
McCann et al. (1990) "c-erbB-2 Oncoprotein Expression in Primary 92 Human Tumors," Cancer 65:88-92.
McDevitt et al. "An alpha-particle emitting antibody ([213Bi]J591) for radioimmunotherapy of prostate cancer.," Cancer Res. 60(21):6095-6100.
Melero et al. (1998) The frequent expansion of a subpopulation of B cells that express RF-associated cross-reactive idiotypes: evidence from analysis of a panel autoreactive monoclonal antibodies; Scand. J. Immunol. 48:152-158 1998.
Metcalfe, Mast Cells, Physiol Rev. Oct. 1997;77(4):1033-79.
Michaelsen et al., "One disulfide bond in front of the second heavy chain constant region is necessary and sufficient for effector functions of human IgG3 without a genetic hinge," Immunology 91 :9243-9247, 1994.
Micklem et al., Different isoforms of human FcRII distinguished by CDw32 antibodies. J Immunol. Mar. 1990;144:2295-2303.
Morgan et al., "The N-terminal end of the CH2 domain of chimeric human IgG1 anti-HLA-DR is necessary for C1q, Fc gamma RI and Fc gamma RIII binding," Immunology 86 :319-324, 1995.
Morrison et al., "Structural determinants of IgG structure," Immunologist 2 :119-124, 1994.
Munn et al., "Phagocytosis of tumor cells by human monocytes cultured in recombinant macrophage colony-stimulating factor," J Exp Med. 172(1):231-7, 1990.
Nagarajan et al., "Ligand binding and phagocytosis by CD16 (Fc gamma receptor III) isoforms. Phagocytic signaling by associated zeta and gamma subunits in Chinese hamster ovary cells," J Biol Chem 270 :25762-25770, 1995.
Nakamura et al. (2005) "Fc receptor targeting in the treatment of allergy, autoimmune diseases and cancer," Expert Opin. Ther. Targets 9(1):169-190.
Nakamura et al., Fc.gamma. receptor IIB-deficient mice develop Goodpasture's Syndrome upon immunization with Type IV collagen: a novel murine model for Autoimmune Glomerular Basement Membrane Disease. J. Exp. Med. Mar. 6, 2000;191(5):899-905.

(56) References Cited

OTHER PUBLICATIONS

NCBI protein sequence report (GenBank entry 1FVE_A "Chain A, X-Ray Structures of the Antigen-Binding Domains from Three Variants of Humanized Anti-P185-HER2 Antibody 4d5 and Comparison with Molecular Modeling" (Oct. 1, 2007).
Neuberger et al., "Recombinant antibodies possessing novel effector functions," Nature 312 :604-608, 1984.
Norderhaug et al., "Chimeric mouse human IgG3 antibodies with an IgG4-like hinge region induce complement-mediated lysis more efficiently than IgG3 with normal hinge," Eur J Immunol 21:2379-84, 1991.
Noren, C.J. et al. "A General Method for Site-Specific Incorporation of Unnatural Amino Acids into Proteins," Science 244:182-188, 1989.
Norris et al., A naturally occurring mutation in Fc.gamma.RIIA: A Q to K.sup.127 change confers unique IgG binding properties to the R.sup.131 allelic form of the receptor. Blood. Jan. 15, 1998;91(2):656-662.
Nose and Leanderson, "Substitution of asparagine324 with aspartic acid in the Fc portion of mouse antibodies reduces their capacity for C1q binding," Eur J Immunol 19 :2179-81, 1989.
Okazaki et al., "Fucose depletion between IgG1 from human IgG1 oligosaccharide enhances binding enthalpy and association rate between IgG1 and FcgammaRIIIa," J Mol Biol 336 :1239-1249, 2004.
Orfao and Ruiz-Arguelles, "General concepts about cell sorting techniques," Clinical Biochem. 29:5-9, 1996.
Ott et al., Downstream of Kinase, p62.sup.dok, Is a mediator of Fc.gamma.RIIB inhibition of Fc.epsilon.RI signaling. J of Immunol. 2002;168:4430-9.
Ott, V.L. et al. "FcgammaRIIB as a potential molecular target for intravenous gamma globulin therapy," J. Allergy Clin Immunol. Oct. 2001:S95-S98.
Panka et al. (1988) Variable region framework differences result in decreased or increased affinity of variant anti-digoxin antibodies. Proc. Natl. Acad. Sci. USA 85:30803084.
Pardridge et al., Blood-brain barrier drug targeting: The future of brain drug development. Molecular Interventions. 2003, 3;2:90-105. See particularly pp. 91-96.
Park et al., Immunoliposomes for cancer treatment. Adv Pharmacol. 1997;40:399-435.
Park YS, Tumor-directed targeting of liposomes. Biosci Rep. Apr. 2002;22(2):267-81.
Partridge et al., "The use of anti-IgG monoclonal antibodies in mapping the monocyte receptor site on IgG," Mol Immunol. 23(12):1365-72, 1986.
Paul, William E, (1993) "Fundamental Microbiology, 3 Ed." pf. 242, 292-296.
Pereira et al. (1998) Cardiolipin Binding a light Chain from Lupus-prone Mice; Biochem. 37:1460-1437.
Perussia "Human Natural Killer Cell Protocols" in *Methods Molecular Biology*. vol. 121 (Campbell et al. eds.) Humana Press Inc., Totowa, NJ. 179-92, 2000.
Pettersen et al. (1999) "CD47 Signals T Cell Death," J. Immunol. 162(12):7031-7040.
Pluckthun, A. et al. (1997) "New protein engineering approaches to multivalent and bispecific antibody fragments," Immunotechnology 3(2):83-105.
Polson, A.G. et al. (Epub Mar. 20, 2007) "Antibody-Drug Conjugates Targeted to CD79 for the Treatment of Non-Hodgkin Lymphoma," Blood. 110(2):616-623.
Presta et al. (2002) "Engineering therapeutic antibodies for improved function," Biochem. Soc. Trans. 30(4):487-490.
Presta LG, Engineering antibodies for therapy. Curr Pharm Biotechnol. Sep. 2002;3(3):237-56.
Presta, L.G. et al. (2005) "Selection, Design and Engineering of Therapeutic Antibodies," J. Allergy Clin. Immunol. 116(4):731-736.
Pricop et al., differential modulation of stimulatory and inhibitory Fc.gamma. receptors on human monocytes by Th1 and Th2 cytokines. J Immunol. Jan. 1, 2001;166(1):531-7.
Pulford et al., 1995 "M6.5: The immunocytochemical distribution of CD16, CD32, and CD64 antigens." Leukocyte Typing V: White cell differentiation antigens 817-821 (Schlossman, Boumsell, Gilks, Harlan, Kishomoto, eds.) pp. 817-821.
Pulford et al., A new monoclonal antibody (KB61) recognizing a novel antigen which is selectively expressed on a subpopulation of human B lymphocytes. Immunology. Jan. 1986;57(1):71-6.
Qin et al., Fc.gamma. receptor IIB on follicular dendritic cells regulates the B cell recall response. J. Immunol. 2000;164:6268-6275.
Radaev and Sun, "Recognition of immunoglobulins by Fcgamma receptors," Molecular Immunology 38 :1073-1083, 2001.
Rankin, et al. CD32B, the human inhibitory Fc-γ receptor IIB, as a target for monoclonal antibody therapy of B-cell lymphoma, Blood Journal, Oct. 1, 2006, vol. 108, No. 7 pp. 2384-2391.
Ravetch and Bolland, "IgG Fc receptors," Annu Rev Immunol 19:275-90, 2001.
Ravetch and Clynes, "Divergent roles for Fc receptors and complement in vivo," Annu Rev Immunol 16:421-432, 1998.
Ravetch and Kinet, "Fc receptors," Annu Rev Immunol 9:457-492, 1991.
Ravetch et al., Fc receptors: rubor redux. Cell. Aug. 26, 1994;78(4):553-60.
Ravetech and Lanier, "Immune inhibitory receptors," Science 290:84-89, 2000.
Reali et al., IgEs targeted on tumor cells: therapeutic activity and potential in the design of tumor vaccines. Cancer Res. 2001;61(14): 5517-22.
Redpath et al., "The influence of the hinge region length in binding of human IgG to human Fcgamma receptors," Hum Immunol 59 :720-727, 1998.
Reff et al., "A review of modifications to recombinant antibodies: attempt to increase efficacy in oncology applications," Critical Reviews in Oncology/Hematology 40: 25-35; 2001.
Reff et al., "Depletion of B cells in vivo by a chimeric mouse human monoclonal antibody to CD20," Blood 83:435-445, 1994.
Riechmann et al., "Reshaping human antibodies for therapy," Nature. 332(6162):323-7, 1988.
Riemer et al. (Epub Jan. 8, 2005) "Matching of trastuzumab (Herceptin) epitope mimics onto the surface of Her-2/neu—a new method of epitope definition.," Mol Immunol. 42(9):1121-1124.
Routledge et al., The effect of aglycosylation on the immunogenicity of a humanized therapeutic CD3 monoclonal antibody. Transplantation Oct. 27, 1995;60(8):847-53.
Rudikoff et al. (1982) "Single amino acid substitution altering antigen-binding specificity" Proc. Natl. Acad. Sci. USA 79:1979-1983.
Rudnick et al. (2009) "Affinity and Avidity in Antibody-Based Tumor Targeting," Can. Biotherp. & Radiopharm. 24:155-162.
Samsom et al. (2005) Fc gamma RIIB regulates nasal and oral tolerance: a role for dendritic cells Immunol. 174:5279-5287.
Samuelsson et al., Anti-inflammatory activity of IVIG mediated through the inhibitory Fc receptor. Science. Jan. 19, 2001; 291:484-486.
Sarkar et al., Negative signaling via Fc.gamma.RIIB1 in B cells blocks phospholipase C.sub..gamma.2. tyrosine phosphorylation but not Syk or Lyn activation. J Biol Chem. Aug. 16, 1996;271(33):20182-6.
Sarmay et al., "Ligand inhibition studies on the role of Fc receptors in antibody-dependent cell-mediated cytotoxicity," Mol Immunol 21 :43-51, 1984.
Sarmay et al., "Mapping and comparison of the interaction sites on the Fc region of IgG responsible for triggering antibody dependent cellular cytotoxicity (ADCC) through different types of human Fc gamma receptor," Mol Immunol 29 :633-639, 1992.
Sarmay et al., "The effect of synthetic peptides corresponding to Fc sequences in human IgG1 on various steps in the B cell activation pathway," Eur J Immunol 18 :289-294, 1988.
Sautes-Fridman et al., "Fc gamma receptors: a magic link with the outside world," ASHI Quarterley, 4th Quarter:148-151, 2003.

(56) References Cited

OTHER PUBLICATIONS

Schaffner et al., "Chimeric interleukin 2 receptor alpha chain antibody derivatives with fused mu and gamma chains permit improved recruitment of effector functions," Mol Immunol 32 :9-20, 1995 (Erratum in 32 :1299, 1995).
Schatz et al., "Use of peptide libraries to map the substrate specificity of a peptide-modifying enzyme: a 13 residue consensus peptide specifies biotinylation in Escherichia coli," Bio/Technology 11:1138-1143, 2000.
Scholl et al., Is colony-stimulating factor-1 a key mediator of breast cancer invasion and metastasis? Mol Carcinog. 7(4):207-11.
Schuna et al., 2000, "New Drugs for the treatment of rheumatoid arthritis." Am J. Health Syst. Phar, 57:225-237.
Seaver (1994) "Monoclonal Antibodies in Industry: More Difficult than Originally Thought," Genetic Engineering News 14(14):10, 21.
Sensel et al., "Amino acid differences in the N-terminus of C(H)2 influence the relative abilities of IgG2 and IgG3 to activate complement," Molecular Immunology 34:1019-1029, 1997.
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem 276 :6591-6604, 2001.
Shields et al., Lack of fucose on human IgG1 N-linked oligosaccharide improves binding to human Fc.gamma. RIII and antibody-dependent on cellular toxicity. J Biol Chem. Jul. 26, 2002;277(30):26733-40.
Shopes et al., "Recombinant human IgG1-murine IgE chimeric Ig. Construction, expression, and binding to human Fc gamma receptors," J Immunol 145 :3842-3848, 1990.
Shopes, "A genetically engineered human IgG mutant with enhanced cytolytic activity," J Immunol 148 :2918-2922, 1992.
Shopes, "A genetically engineered human IgG with limited flexibility fully initiates cytolysis via complement," Molecular Immunology 30 :603-609, 1993.
Shusta et al., "Directed evolution of a stable scaffold for T-cell receptor engineering," Nature Biotechnology 18:754-759, 2000.
Shusta et al., "Increasing the secretory capacity of Saccharomyces cerevisiae for production of single-chain antibody fragments," Nature Biotechnology 16:773-777, 1998.
Shusta et al., "Yeast polypeptide fusion surface display levels predict thermal stability and soluble secretion efficiency," J Mol Biol 292:949-956, 1999.
Siberil, S. et al. (2006) "Molecular Aspects of Human FcgammaR Interactions with IgG: Functional and Therapeutic Consequences," Immunol. Lett. 106:111-118 (2006).
Singapore Search Report SG 200607186-4 dated Nov. 5, 2008.
Skolnick et al. (2000) From Genes to Protein Structure and Function: Novel Aspects of Computational Approaches in the Genomic Era, Trends in Biotechnology 18:34-39.
Sleister et al., "Subtractive Immunization; A tool for the generation of discriminatory antibodies to proteins of similar sequence," Journal of Immunological Methods 261: 213-220, (2002).
Smith and Morrison, "Recombinant polymeric IgG: an approach to engineering more potent antibodies," Bio/Technology 12:683-688, 1994.
Smith-Gill et al. (1987) "Contributions of Immunoglobulin Heavy and Light Chains to Antibody Specificity for Lysozyme and Two Haptens," J. Immunol. 139:4135-4144.
Sondermann and Oosthuizen, "The structure of Fc receptor/Ig complexes: considerations on stoichiometry and potential inhibitors," Immunology Letters, 82:51-56, 2002.
Sondermann et al., "Crystal structure of the soluble form of the human fcgamma-receptor IIb: a new member of the immunoglobulin superfamily at 1.7 A resolution," EMBO J 18:1095-1103, 1999.
Sondermann et al., "Molecular basis for immune complex recognition: a comparison of Fc-receptor structures," J. Mol. Biol. 309:737-749, 2001.
Sondermann et al., "The 3.2—A crystal structure of the human IgG1 Fc fragment-Fc gammaRIII complex," Nature 406:267-273, 2000.

Song et al. (2000) "Light Chaing of Natural Antibody Plays a Dominant Role in Protein Antigen Binding," Biochem. Biophys. Res. Comm. 268:390-394.
Stancovski et al. (1991) "Mechanistic aspects of the opposing effects of monoclonal antibodies to the ERBB2 receptor on tumor growth," Proc Natl Acad Sci U S A. 88(19):8691-8695.
Stavenhagen et al. (2007) "Fc Optimization of Therapeutic Antibodies Enhances Their Ability to Kill Tumor Cells In vitro and Controls Tumor Expansion In vivo via Low-Affinity ActivatingFc ; Receptors" Cancer Res. 67(18):8882-8890.
Stavenhagen et al. (2008) "Enhancing the potency of therapeutic monoclonal antibodies via Fc optimization," Advan. Enzyme Regul. 48:152-164.
Stefanescu et al. (2004) "Inhibitory Fc Gamma Receptors: From Gene to Disease," J. Clinical Immunol. 24(4):315-326.
Steplewski et al., "Biological activity of human-mouse IgG1, IgG2, IgG3, and IgG4 chimeric monoclonal antibodies with antitumor specificity," Proc. Natl. Acad. Sci. U.S.A. 85:4852-4856, 1988.
Strohmeier et al., "Role of the Fc gamma R subclasses Fc gamma RII and Fc gamma RIII in the activation of human neutrophils by low and high valency immune complexes," J Leukocyte Biol. 58:415-422, 1995.
Su et al., Expression profile of Fc.gamma.RIIB on leukocytes and its dysregulation in systemic lupus erythematosus. J. Immunol. 178:3272-3280, 2007.
Sylvestre and Ravetch, "A dominant role for mast cell Fc receptors in the Arthus reaction," Immunity 5:387-390, 1996.
Sylvestre and Ravetch, "Fc receptors initiate the Arthus reaction: redefining the inflammatory cascade," Science 265:1095-1098, 1994.
Takai et al. (2003) "Fc Receptors as Potential Targets for the Treatment of Allergy, Autoimmune Disease and Cancer," Immune, Endo. & Meta. Disorders 3:187-197.
Takai et al., "Augmented humoral and anaphylactic responses in Fc gamma RII-deficient mice," Nature 379:346-349, 1996.
Takai et al., "FcR gamma chain deletion results in pleiotrophic effector cell defects," Cell 76 :519-529, 1994.
Takai, "Roles of Fc receptors in autoimmunity," Nature Reviews 2:580-592, 2002.
Talmadge et al. (2007) "Murine Models to Evaluate Novel and Conventional Therapeutic Strategies for Cancer," Am. J. Pathol. 170(3):793-804.
Tam et al., A bispecific antibody against human mast human IgE and human Fc.gamma.RII that inhibits antigen-induced histamine release by cells and basophils. Allergy 2004;59:772-780.
Tamm et al., "The IgG binding site of human FcγRIIIB receptor involves CC' and FG loops of the membrane-proximal domain," J Biol Chem 271:3659-3666, 1996.
Tao and Morrison, Studies of aglycosylated chimeric mouse-human IgG. Role of carbohydrate in the structure and effector functions mediated by the human IgG constant region. J Immunol. Oct. 15, 1989;143(8):2595-601.
Tao et al., "Structural features of human immunoglobulin G that determine isotype-specific differences in complement activation," Exp Med 178:661-667, 1993.
Tao et al., "The differential ability of human IgG1 and IgG4 to activate complement is determined by the COOH-terminal sequence of the CH2 domain," J Exp Med 173:1025-1028, 1991.
Thurber et al. (2008) "Antibody Tumor Penetration: Transport Opposed by Systemic and Antigen-Mediated Clearance," Adv. Drug Deliv. Rev. 60:1421-1434.
Todorovska et al., Design and application of diabodies, triabodies and tetrabodies for cancer targeting. J Immunol Methods. Feb. 1, 2001;248(1-2):47-66.
Tridandapandi et al., "Regulated Expression Journal of Biological and Inhibitory Function of FegammaRIIB in Human Monocytic Cells," Chemistry 277(7): 5082-5089, 2002.
Umana et al., Engineered glycoforms of an antineuroblastoma IgG1 with optimized antibody-dependent cellular cytotoxic activity. Nat Biotechnol. Feb. 1999;17(2):176-80.
Vajdos et al. (2002) "Comprehensive Functional Maps of the Antigen-Binding Site of an Anti-ErbB2 Antibody Obtained with Shotgun Scanning Mutagenesis," J. Molec. Biol. 320:415-428.

(56) References Cited

OTHER PUBLICATIONS

Van Antwerp and Wittrup, "Fine affinity discrimination by yeast surface display and flow cytometry," Biotechnol Prog 16:31-37, 2000.
Van De Winkel et al., 1995, "CD32 cluster workshop report." Leukocyte Typing V: White Cell differentiation antigens 823-825 (Schlossman, Boumsell, Gilks, Harlan, Kishomoto, eds.).
Van den Beuken et al. (2001) Building novel binding ligands to B7.1 and B7.2 based on human antibody single variable light chain domains; J Molec. Biol. 310:591-601.
Van Nguyen et al., Colony stimulating factor-1 is required to recruit macrophages into the mammary gland to facilitate mammary ductal outgrowth. Dev Biol. 2002;247(1):11-25
Van Sorge et al., "FcgammaR polymorphisms: Implications for function, disease susceptibility and immunotherapy," Tissue Antigens 61:189-202, 2003.
Vely et al., 1997, "A new set of monoclonal antibodies against human Fc gamma RII (CD32) and Fc gamma RIII (CD16): characterization and use in various assays." Hybridoma 16(6):519-28.
Veri et al. (2010) "Therapeutic Control of B Cell Activiation via Recruitment of Fcγ Receptor IIb (CD32B) Inhibitory Function With a Novel Bispecific Antibody Scaffold," Arth. & Rheum. 62(7):1933-1943.
Veri, M.C. et al. (2007) "Monoclonal antibodies capable of discriminating the human inhibitory Fcgamma-receptor IIB (CD32B) from the activating Fcgamma-receptor IIA (CD32A): biochemical, biological and functional characterization," Immunology 121(3):392-404.
Vidarte, "Serine 132 is the C3 covalent attachment point on the CH1 domain of human IgG1," J Biol Chem 276:38217-38233, 2001.
Vingerhoeds et al., Immunoliposomes in vivo. Immunomethods. Jun. 1994;4(3):259-72.
Vitetta, E.S. et al. (2006) "Immunology. Cnsidering Therapeutic Antibodies," Science 313:308-309.
Voskoglou-Nomikos et al. (2003) "Clinical Predictive Value of the in Vitro Cell Line, Human Xenograft, and Mouse Allograft Preclinical Cancer Models," Clin. Can. Res. 9:4227-4239.
Vuist et al. (1990) "Two distinct mechanisms of antitumor activity mediated by the combination of interleukin 2 and monoclonal antibodies," Canc. Res. 50:5767-5772.
Wallick et al., Glycosylation of a VH residue of a monoclonal antibody against {acute over (.alpha.)} (1.fwdarw.6) dextran increases its affinity for antigen. J Exp Med. Sep. 1, 1988;168(3):1099-109.
Ward and Ghetie, "The effector functions of immunoglobulins: implications for therapy," Therapeutic Immunology 2:77-94, 1995.
Ward et al. (1989) Building Activities of a repertoire of single immunoglobulin variable domains secreted from *Escherichia coli*, Nature 341:544-546 (1989).
Warmerdam et al., Molecular basis for a polymorphism of human Fc gamma receptor II (CD32). J Exp Med. Jul. 1, 1990;172(1):19-25.
Warren, HS et al.(1999) "NK cells and apoptosis," Immunol. Cell Biol. 77(1):64-75.
Weinrich, V. et al. "Epitope Mapping of New Monoclonal Antibodies Recognizing Distinct Human FCRII (CD32) Isoforms," Hybridoma 15(2):109-116.

Weng and Levy, "Two immunoglobulin G fragment C receptor polymorphisms independently predict response to rituximab in patients with follicular lymphoma," J Clin Oncol 21:3940-3947, 2003.
Wheeler, "Preventive Vaccines for Cervical Cancer," Salud Publica d Mexico, 1997, vol. 39, pp. 1-9.
Wiener, E. et al. "Differences between the activities of human monoclonal IgG1 and IgG3 anti-D antibodies of the Rh blood group system in their abilities to mediate effector functions of monocytes," Immunol. 65:159-163 (1988).
Wing et al., "Mechanism of first-dose cytokine-release syndrome by CAMPATH 1-H: Involvement ofCD16 (FcγRIII) and CD11a/CD18 (LFA-1) on NK cells," J Clin Invest 98 :2819-2826, 1996.
Wingren et al., "Comparison of surface properties of human IgA, IgE, IgG and IgM antibodies with identical and different specificities," Scand J Immunol 44:430-436, 1996.
Wittrup, "The single cell as a microplate well," Nat Biotechnol 18:1039-1040, 2000.
Wittrup, "Protein engineering by cell-surface display," Curr, Opin. Biotechnol. 12:395-399, 2001.
Woof et al., "Localisation of the monocyte-binding region on human immunoglobulin G," Mol Immunol 23 :319-330, 1986.
Wright and Morrison, Effect of glycosylation on antibody function: implications for genetic engineering. Trends Biotechnol. Jan. 1997;15(1):26-32.
Wu et al. (2001) "Multimerization of a chimeric anti-DC20 Single-Chain Fv-Fc fusion protein is mediated through variable domain exchange," Protein Engineering 14(2): 1025-1033.
Wu et al., "A novel polymorphism of FcγRIIIa (CD16) alters receptor function and predisposes to autoimmune disease," J Clin Invst 100:1059-1070, 1997.
Wu et al., "Humanization of a Murine Monoclonal Antibody by Simultaneous Optimization of Framework and CDR Residues," Journal of Molecular Biology, 1999, vol. 294, pp. 151-162.
Xu et al. (1993) "Antibody-induced growth inhibition is mediated through immunochemically and functionally distinct epitopes on the extracellular domain of the c-erbB-2 (HER-2/neu) gene product p185," Int. J. Cancer. 53(3):401-408.
Xu et al., "Residue at position 331 in the IgG1 and IgG4 CH2 domains contributes to their differential ability to bind and activate complement," J Biol Chem 269 :3469-3474, 1994.
Xu et al., Fc.gamma.RS Modulate Cytotoxicity of Anti-Fas Antibodies: Implications for Agonistic Antibody Based Therapeutics. J Immunol. 2003;171:562-68.
Yeung and Wittrup, "Quantitative screening of yeast surface-displayed polypeptide libraries by magnetic bead capture," Biotechnol Prog 18:212-220, 2002.
Yonemura et al. (1991) "Evaluation of Immunoreactivity for erbB-2 Protein as a Marker of Poor Short Term Prognosis in Gastric Cancer," Cancer Research 51:1034-1038.
Zeidler et al., "The Fc-region of a new class of intact bispecific antibody mediates activation of accessory cells and NK cells and induces direct phagocytosis of tumour cells," British J Cancer 83:261-266, 2000.
Zola et al., 2000, "CD32 (FcgammaRII)." J Biol Regul Homeost Agents 14(4):311-6.
Zuckier et al., "Chimeric human-mouse IgG antibodies with shuffled constant region exons demonstrate that multiple domains contribute to in vivo half-life," Cancer Res 58 :3905-3908, 1998.

\* cited by examiner

```
                      10        20        30
Murine      DIVMTQSHKFMSTSVGDRVSITCKASQDVN
Chimeric    DIVMTQSHKFMSTSVGDRVSITCKASQDVN
Humanized   DIQMTQSPSSLSASVGDRVTITCRASQDVN 40        50        60
Murine      TAVAWYQQKPGHSPKLLIYSASFRYTGVPD
Chimeric    TAVAWYQQKPGHSPKLLIYSASFRYTGVPD
Humanized   TAVAWYQQKPGKAPKLLIYSASFLESGVPS 70        80        90
Murine      RFTGNRSGTDFTFTISSVQAEDLAVYYCQQ
Chimeric    RFTGSRSGTDFTFTISSVQAEDLAVYYCQQ
Humanized   RFSGSRSGTDFTLTISSLQPEDFATYYCQQ 100       109
Murine      HYTTPPTFGGGTKLEIKRA
Chimeric    HYTTPPTFGGGTKVEIKRT
Humanized   HYTTPPTFGQGTKVEIKRT
```

Figure 1

```
MT1  QVQLQQSGPELVKPGASLKLSCTASGFNIKDTYIHWVKQRPEQGLEWIGRIYPTNGYTRY  60
MT2  QVQLQQSGPELVKPGASLKLSCTASGFNIKDTYIHWVKQRPEQGLEWIGRIYPTNGYTRY  60
MT3  QVQLQQSGPELVKPGASLKLSCTASGFNIKDTYIHWVKQRPEQGLEWIGRIYPTNGYTRY  60
WT   QVQLQQSGPELVKPGASLKLSCTASGFNIKDTYIHWVKQRPEQGLEWIGRIYPTNGYTRY  60

MT1  DPKFQDKATITADTSSNTAYLQVSRLTSEDTAVYYCSRWGGDGFYAMDYWGQGASVTVSS  120
MT2  DPKFQDKATITADTSSNTAYLQVSRLTSEDTAVYYCSRWGGDGFYAMDYWGQGASVTVSS  120
MT3  DPKFQDKATITADTSSNTAYLQVSRLTSEDTAVYYCSRWGGDGFYAMDYWGQGASVTVSS  120
WT   DPKFQDKATITADTSSNTAYLQVSRLTSEDTAVYYCSRWGGDGFYAMDYWGQGASVTVSS  120

MT1  ASTKGPSVFPLAPSSKSTSGGTAALGCLVKDYFPEPVTVSWNSGALTSGVHTFPAVLQSS  180
MT2  ASTKGPSVFPLAPSSKSTSGGTAALGCLVKDYFPEPVTVSWNSGALTSGVHTFPAVLQSS  180
MT3  ASTKGPSVFPLAPSSKSTSGGTAALGCLVKDYFPEPVTVSWNSGALTSGVHTFPAVLQSS  180
WT   ASTKGPSVFPLAPSSKSTSGGTAALGCLVKDYFPEPVTVSWNSGALTSGVHTFPAVLQSS  180

MT1  GLYSLSSVVTVPSSSLGTQTYICNVNHKPSNTKVDKRVEPKSCDKTHTCPPCPAPELLGG  240
MT2  GLYSLSSVVTVPSSSLGTQTYICNVNHKPSNTKVDKRVEPKSCDKTHTCPPCPAPELVGG  240
MT3  GLYSLSSVVTVPSSSLGTQTYICNVNHKPSNTKVDKRVEPKSCDKTHTCPPCPAPELLGG  240
WT   GLYSLSSVVTVPSSSLGTQTYICNVNHKPSNTKVDKRVEPKSCDKTHTCPPCPAPELLGG  240

MT1  PSVFLLPPKPKDTLMISRTPEVTCVVVDVSHEDPEVKFNWYVDGVEVHNAKTKPPEEQYN  300
MT2  PSVFLLPPKPKDTLMISRTPEVTCVVVDVSHEDPEVKFNWYVDGVEVHNAKTKPPEEQYN  300
MT3  PSVFLLPPKPKDTLMISRTPEVTCVVVDVSHEDPEVKFNWYVDGVEVHNAKTKPPEEQYN  300
WT   PSVFLFPPKPKDTLMISRTPEVTCVVVDVSHEDPEVKFNWYVDGVEVHNAKTKPREEQYN  300

MT1  STLRVVSILTVLHQDWLNGKEYKCKVSNKALPAPIEKTISKAKGQPREPQVYTLPPSRDE  360
MT2  STLRVVSVLTVLHQDWLNGKEYKCKVSNKALPAPIEKTISKAKGQPREPQVYTLPPSRDE  360
MT3  STLRVVSVLTVLHQDWLNGKEYKCKVSNKALPAPIEKTISKAKGQPREPQVYTLPPSRDE  360
WT   STYRVVSVLTVLHQDWLNGKEYKCKVSNKALPAPIEKTISKAKGQPREPQVYTLPPSRDE  360

MT1  LTKNQVSLTCLVKGFYPSDIAVEWESNGQPENNYKTTPLVLDSDGSFFLYSKLTVDKSRW  420
MT2  LTKNQVSLTCLVKGFYPSDIAVEWESNGQPENNYKTTPLVLDSDGSFFLYSKLTVDKSRW  420
MT3  LTKNQVSLTCLVKGFYPSDIAVEWESNGQPENNYKTTPPVLDSDGSFFLYSKLTVDKSRW  420
WT   LTKNQVSLTCLVKGFYPSDIAVEWESNGQPENNYKTTPPVLDSDGSFFLYSKLTVDKSRW  420

MT1  QQGNVFSCSVMHEALHNHYTQKSLSLSPGK  450
MT2  QQGNVFSCSVMHEALHNHYTQKSLSLSPGK  450
MT3  QQGNVFSCSVMHEALHNHYTQKSLSLSPGK  450
WT   QQGNVFSCSVMHEALHNHYTQKSLSLSPGK  450
```

Figure 2

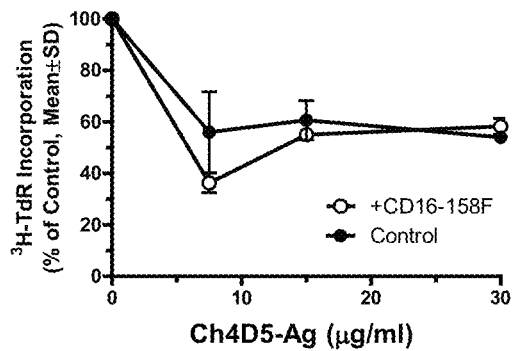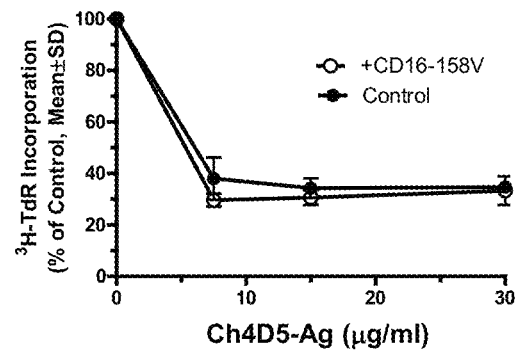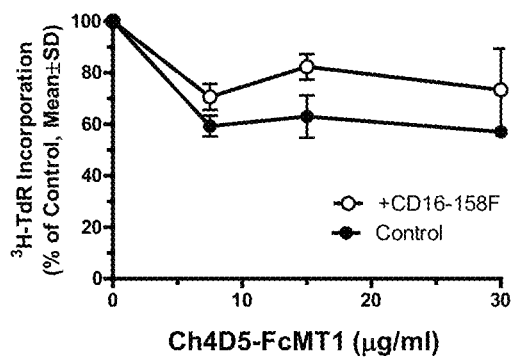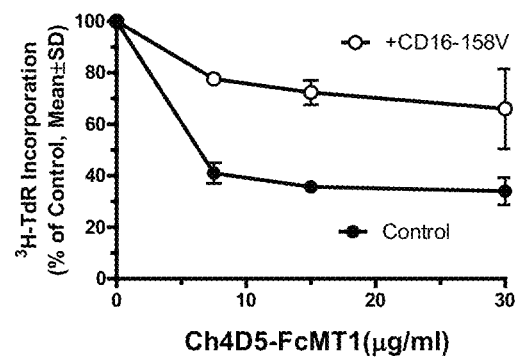
Figure 4

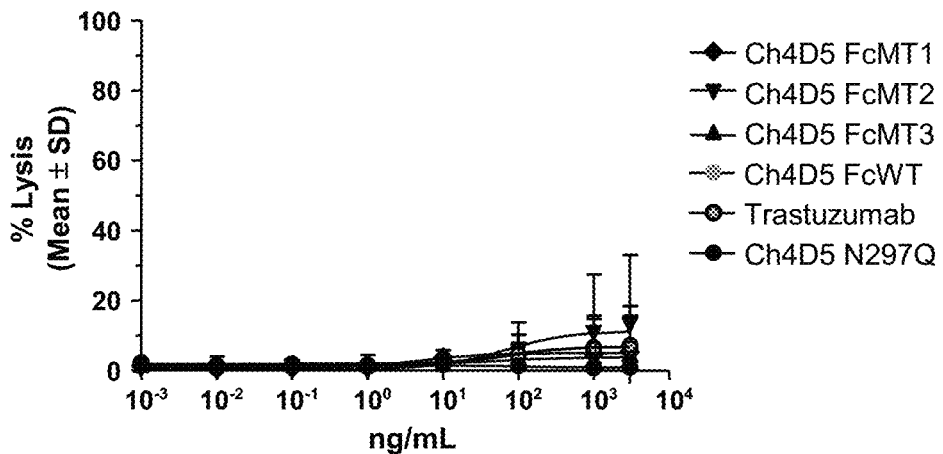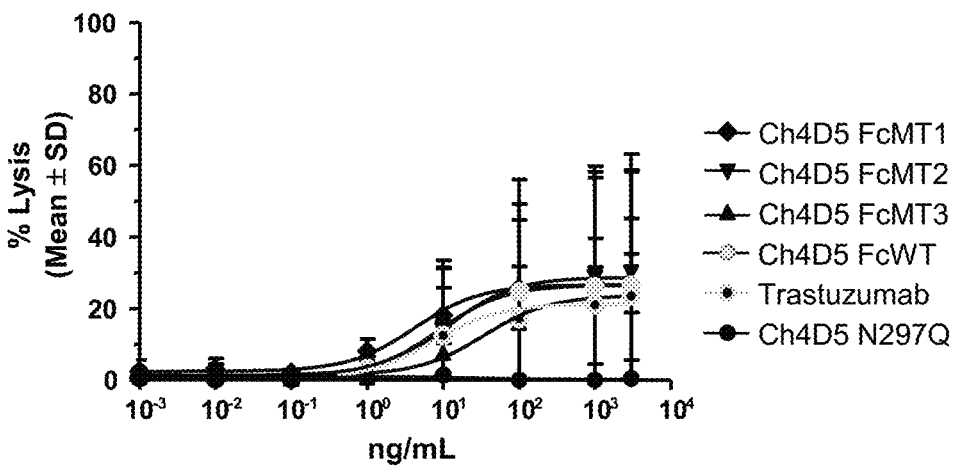
Figure 10

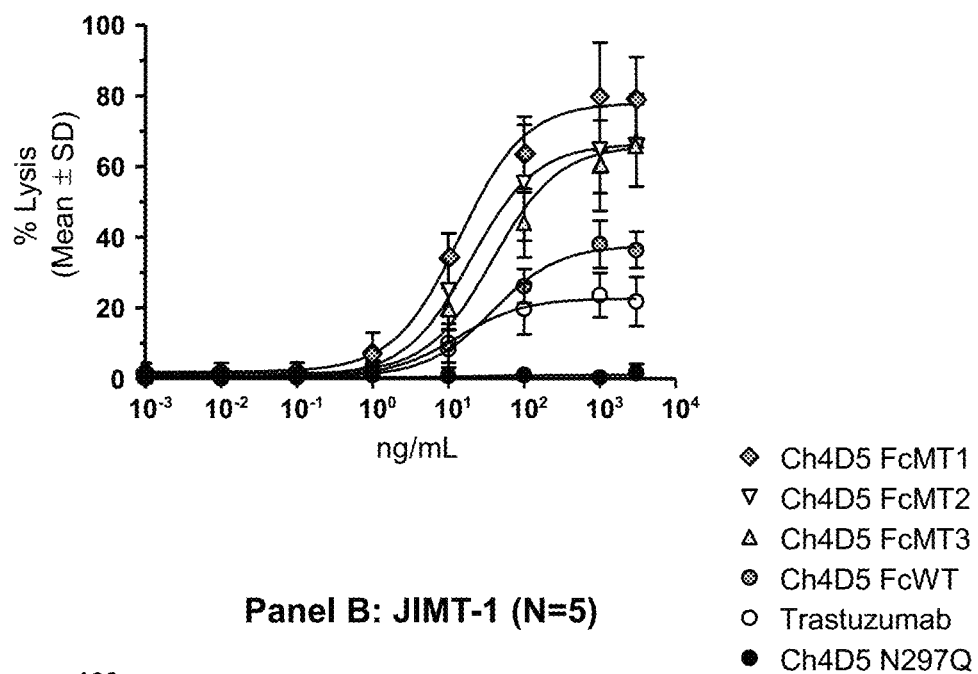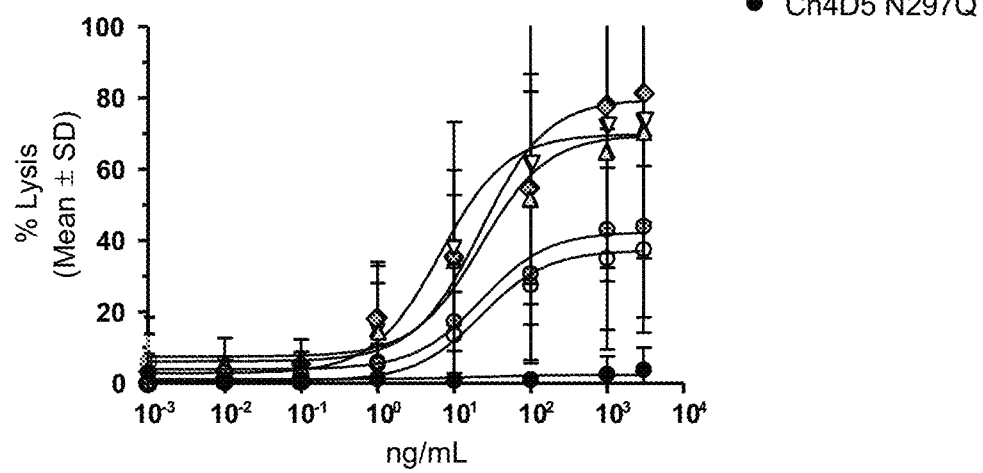
FIG. 12

SEQUENCE LISTING

<160> NUMBER OF SEQ ID NOS: 13

<210> SEQ ID NO 1
<211> LENGTH: 645
<212> TYPE: DNA
<213> ORGANISM: Artificial
<220> FEATURE:
<223> OTHER INFORMATION: Chimeric (murine-human)

<400> SEQUENCE: 1

```
gacatcgtga tgacccagtc ccacaagttc atgtccacct ctgtgggcga tagggtcagc      60
atcacctgca aggccagcca ggatgtgaat actgctgtag cctggtatca gcagaaacca     120
ggacattctc ccaaactgct gatttactcc gcatccttcc ggtacactgg agtccctgat     180
cgcttcactg gcagcagatc tgggacagat ttcactttca ccatcagcag tgtgcaggct     240
gaagacctgg cagtttatta ctgtcagcaa cattatacta cacctccac cttcggaggg      300 ggtaccaagg tggagatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttag                     645
```

<210> SEQ ID NO 2
<211> LENGTH: 214
<212> TYPE: PRT
<213> ORGANISM: Artificial
<220> FEATURE:
<223> OTHER INFORMATION: Chimeric (murine-human)

<400> SEQUENCE: 2

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly His Ser Pro Lys Leu Leu Ile
        35                  40                  45

Tyr Ser Ala Ser Phe Arg Tyr Thr Gly Val Pro Asp Arg Phe Thr Gly
50                  55                  60

Ser Arg Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 3
<211> LENGTH: 109
<212> TYPE: PRT
<213> ORGANISM: Mus musculus

<400> SEQUENCE: 3

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly His Ser Pro Lys Leu Leu Ile
        35                  40                  45

Tyr Ser Ala Ser Phe Arg Tyr Thr Gly Val Pro Asp Arg Phe Thr Gly
50                  55                  60

Asn Arg Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Pro
                85                  90                  95

Thr Phe Gly Gly Gly Thr Lys Leu Glu Ile Lys Arg Ala
            100                 105

<210> SEQ ID NO 4
<211> LENGTH: 109
<212> TYPE: PRT
<213> ORGANISM: Artificial
<220> FEATURE:
<223> OTHER INFORMATION: Chimeric (murine-human)

<400> SEQUENCE: 4

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly His Ser Pro Lys Leu Leu Ile
        35                  40                  45

Tyr Ser Ala Ser Phe Arg Tyr Thr Gly Val Pro Asp Arg Phe Thr Gly
50                  55                  60

Ser Arg Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Pro
                85                  90                  95

Thr Phe Gly Gly Gly Thr Lys Val Glu Ile Lys Arg Thr
            100                 105

<210> SEQ ID NO 5
<211> LENGTH: 109
<212> TYPE: PRT
<213> ORGANISM: Artificial
<220> FEATURE:
<223> OTHER INFORMATION: Humanized

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Glu Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr
            100                 105

<210> SEQ ID NO 6
<211> LENGTH: 1353
<212> TYPE: DNA
<213> ORGANISM: Mus musculus

<400> SEQUENCE: 6
caggttcagc tgcagcagtc tggccctgag ctggtgaagc caggggcctc actcaagttg      60
tcctgtacag cttctggctt caacatcaaa gacacctata tccactgggt gaaacagagg     120
cctgaacagg gcctggaatg gattggaagg atttatccta ccaatggcta tactagatat     180
gacccaaagt tccaggacaa ggccactatc acagcagaca catcctccaa cacagcctac     240
ctgcaagtca gccgcctgac atctgaggac actgccgtct attactgctc ccggtgggga     300
ggggacggct ctatgctat ggactactgg ggtcagggag cctccgtgac cgtgagctcc     360
gcctccacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540

```
ggactctact ccctcagcag cgtggtgacc gtgccctcca gcagcttggg cacccagacc    600
tacatctgca acgtgaatca caagcccagc aacaccaagg tggacaagag agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag gcagccccg agaaccacag gtgtacaccc tgcccccatc ccgggatgag    1080
ctgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctac agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa tga                                1353
```

<210> SEQ ID NO 7
<211> LENGTH: 450
<212> TYPE: PRT
<213> ORGANISM: Mus musculus

<400> SEQUENCE: 7

```
Gln Val Gln Leu Gln Gln Ser Gly Pro Glu Leu Val Lys Pro Gly Ala
1               5                   10                  15

Ser Leu Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Tyr Pro Thr Asn Gly Tyr Thr Arg Tyr Asp Pro Lys Phe
    50                  55                  60

Gln Asp Lys Ala Thr Ile Thr Ala Asp Thr Ser Ser Asn Thr Ala Tyr
65                  70                  75                  80

Leu Gln Val Ser Arg Leu Thr Ser Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Ala Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220
```

| | | | | | | | | | | | |
|---|---|---|---|---|---|---|---|---|---|---|---|
| Lys | Thr | His | Thr | Cys | Pro | Pro | Cys | Pro | Ala | Pro | Glu | Leu | Leu | Gly | Gly |
| 225 | | | | 230 | | | | | 235 | | | | | 240 | |

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
450

<210> SEQ ID NO 8
<211> LENGTH: 1353
<212> TYPE: DNA
<213> ORGANISM: Artificial
<220> FEATURE:
<223> OTHER INFORMATION: Chimeric (murine-human)

<400> SEQUENCE: 8
caggttcagc tgcagcagtc tggccctgag ctggtgaagc caggggcctc actcaagttg      60
tcctgtacag cttctggctt caacatcaaa gacacctata tccactgggt gaaacagagg     120
cctgaacagg gcctggaatg gattggaagg atttatccta ccaatggcta tactagatat     180
gacccaaagt tccaggacaa ggccactatc acagcagaca catcctccaa cacagcctac     240
ctgcaagtca gccgcctgac atctgaggac actgccgtct attactgctc ccggtgggga     300
ggggacggct ctatgctat ggactactgg ggtcagggag cctccgtgac cgtgagctcc     360
gcctccacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagag agttgagccc     660
aaatcttgtg acaaaactca cacatgccca ccgtgcccag cacctgaact cctggggggga     720

```
ccgtcagtct tcctcttacc cccaaaaccc aaggacaccc tcatgatctc ccggacccct      780
gaggtcacat gcgtggtggt ggacgtgagc cacgaagacc ctgaggtcaa gttcaactgg      840
tacgtggacg gcgtggaggt gcataatgcc aagacaaagc cgccggagga gcagtacaac      900
agcacgctcc gtgtggtcag catcctcacc gtcctgcacc aggactggct gaatggcaag      960
gagtacaagt gcaaggtctc caacaaagcc ctcccagccc ccatcgagaa aaccatctcc     1020
aaagccaaag gcagccccg agaaccacag gtgtacaccc tgcccccatc ccgggatgag      1080
ctgaccaaga accaggtcag cctgacctgc ctggtcaaag gcttctatcc cagcgacatc     1140
gccgtggagt gggagagcaa tgggcagccg gagaacaact acaagaccac gcctctcgtg     1200
ctggactccg acggctcctt cttcctctac agcaagctca ccgtggacaa gagcaggtgg     1260
cagcagggga acgtcttctc atgctccgtg atgcatgagg ctctgcacaa ccactacacg     1320
cagaagagcc tctccctgtc tccgggtaaa tga                                  1353
```

<210> SEQ ID NO 9
<211> LENGTH: 450
<212> TYPE: PRT
<213> ORGANISM: Artificial
<220> FEATURE:
<223> OTHER INFORMATION: Chimeric (murine-human)

<400> SEQUENCE: 9

```
Gln Val Gln Leu Gln Gln Ser Gly Pro Glu Leu Val Lys Pro Gly Ala
1               5                   10                  15

Ser Leu Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Tyr Pro Thr Asn Gly Tyr Thr Arg Tyr Asp Pro Lys Phe
    50                  55                  60

Gln Asp Lys Ala Thr Ile Thr Ala Asp Thr Ser Ser Asn Thr Ala Tyr
65                  70                  75                  80

Leu Gln Val Ser Arg Leu Thr Ser Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Ala Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Leu Pro Pro Lys Pro Lys Asp Thr Leu Met Ile
                245                 250                 255
```

```
Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Pro Glu Glu Gln Tyr Asn Ser Thr Leu Arg
290                 295                 300

Val Val Ser Ile Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Leu Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 10
<211> LENGTH: 1353
<212> TYPE: DNA
<213> ORGANISM: Artificial
<220> FEATURE:
<223> OTHER INFORMATION: Chimeric (murine-human)

<400> SEQUENCE: 10
caggttcagc tgcagcagtc tggccctgag ctggtgaagc aggggcctc actcaagttg      60 tcctgtacag cttctggctt caacatcaaa gacaccctata tccactgggt gaaacagagg     120
cctgaacagg gcctggaatg gattggaagg atttatccta ccaatggcta ctagatat       180 gacccaaagt tccaggacaa ggccactatc acagcagaca catcctccaa cacagcctac     240
ctgcaagtca gccgcctgac atctgaggac actgccgtct attactgctc ccggtgggga     300
ggggacggct ctatgctat ggactactgg ggtcagggag cctccgtgac cgtgagctcc      360
gcctccacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagag agttgagccc     660
aaatcttgtg acaaaactca cacatgccca ccgtgcccag cacctgaact cgtggggga     720 ccgtcagtct tcctcttacc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgccggagga gcagtacaac     900
```

```
agcacgctcc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag ggcagccccg agaaccacag gtgtacaccc tgccccccatc ccgggatgag   1080 ctgaccaaga accaggtcag cctgacctgc ctggtcaaag gcttctatcc cagcgacatc   1140
gccgtggagt gggagagcaa tgggcagccg gagaacaact acaagaccac gcctctcgtg   1200
ctggactccg acggctcctt cttcctctac agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa tga                                1353
```

<210> SEQ ID NO 11
<211> LENGTH: 450
<212> TYPE: PRT
<213> ORGANISM: Artificial
<220> FEATURE:
<223> OTHER INFORMATION: Chimeric (murine-human)

<400> SEQUENCE: 11

```
Gln Val Gln Leu Gln Gln Ser Gly Pro Glu Leu Val Lys Pro Gly Ala
1               5                   10                  15

Ser Leu Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Tyr Pro Thr Asn Gly Tyr Thr Arg Tyr Asp Pro Lys Phe
    50                  55                  60

Gln Asp Lys Ala Thr Ile Thr Ala Asp Thr Ser Ser Asn Thr Ala Tyr
65                  70                  75                  80

Leu Gln Val Ser Arg Leu Thr Ser Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Ala Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Val Gly Gly
225                 230                 235                 240

Pro Ser Val Phe Leu Leu Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
```

|     |     |     |     | 275 |     |     |     | 280 |     |     |     | 285 |     |     |
| --- | --- | --- | --- | --- | --- | --- | --- | --- | --- | --- | --- | --- | --- | --- |
| Asn | Ala | Lys | Thr | Lys | Pro | Pro | Glu | Glu | Gln | Tyr | Asn | Ser | Thr | Leu | Arg |
|     |     |     |     | 290 |     |     |     | 295 |     |     |     | 300 |     |     |     |

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Leu Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 12
<211> LENGTH: 1353
<212> TYPE: DNA
<213> ORGANISM: Artificial
<220> FEATURE:
<223> OTHER INFORMATION: Chimeric (murine-human)

<400> SEQUENCE: 12

```
caggttcagc tgcagcagtc tggccctgag ctggtgaagc caggggcctc actcaagttg     60
tcctgtacag cttctggctt caacatcaaa gacaccctat ccactgggt gaaacagagg    120
cctgaacagg gcctggaatg gattggaagg atttatccta ccaatggcta ctagatat    180
gacccaaagt tccaggacaa ggccactatc acagcagaca catcctccaa cacagcctac    240
ctgcaagtca gccgcctgac atctgaggac actgccgtct attactgctc ccggtgggga    300
ggggacggct tctatgctat ggactactgg ggtcagggag cctccgtgac cgtgagctcc    360
gcctccacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagag agttgagccc    660
aaatcttgtg acaaaactca cacatgccca ccgtgcccag cacctgaact cctgggggga    720
ccgtcagtct tcctcttacc cccaaaaccc aaggacaccc tcatgatctc ccggaccct    780
gaggtcacat gcgtggtggt ggacgtgagc cacgaagacc ctgaggtcaa gttcaactgg    840
tacgtggacg gcgtggaggt gcataatgcc aagacaaagc cgcggagga gcagtacaac    900
agcacgctcc gtgtggtcag cgtcctcacc gtcctgcacc aggactggct gaatggcaag    960
gagtacaagt gcaaggtctc caacaaagcc ctcccagccc ccatcgagaa aaccatctcc   1020
```

-continued

```
aaagccaaag ggcagccccg agaaccacag gtgtacaccc tgcccccatc ccgggatgag    1080
ctgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa tga                                 1353

<210> SEQ ID NO 13
<211> LENGTH: 450
<212> TYPE: PRT
<213> ORGANISM: Artificial
<220> FEATURE:
<223> OTHER INFORMATION: Chimeric (murine-human)

<400> SEQUENCE: 13

Gln Val Gln Leu Gln Gln Ser Gly Pro Glu Leu Val Lys Pro Gly Ala
1               5                   10                  15

Ser Leu Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Tyr Pro Thr Asn Gly Tyr Thr Arg Tyr Asp Pro Lys Phe
    50                  55                  60

Gln Asp Lys Ala Thr Ile Thr Ala Asp Thr Ser Ser Asn Thr Ala Tyr
65                  70                  75                  80

Leu Gln Val Ser Arg Leu Thr Ser Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Ala Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Glu Glu Gln Tyr Asn Ser Thr Leu Arg
    290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450
```

HER2/NEU-SPECIFIC ANTIBODIES AND METHODS OF USING SAME

CROSS-REFERENCE TO RELATED APPLICATIONS

This application is a continuation of U.S. patent application Ser. No. 15/266,421 (filed Sep. 15, 2016), which application is a continuation of U.S. patent application Ser. No. 14/994,892 (filed Jan. 13, 2016; issued as U.S. Pat. No. 9,469,692), which application is a continuation of U.S. patent application Ser. No. 14/332,239 (filed Jul. 15, 2014; issued as U.S. Pat. No. 9,243,069), which application is a divisional of U.S. patent application Ser. No. 12/933,885 (filed Jan. 11, 2011; issued as U.S. Pat. No. 8,802,093), which application is a National Stage Application under 35 U.S.C. § 371 of PCT/US2009/038201 (filed Mar. 25, 2009), which claims priority to U.S. Patent Application Ser. No. 61/041,649 (filed Apr. 2, 2008), which applications are herein incorporated by reference in their entireties and to which priority is claimed.

REFERENCE TO SEQUENCE LISTING

This application includes one or more Sequence Listings pursuant to 37 C.F.R. 1.821 et seq., submitted herewith as an ASCII text file Sequence Listing (file name: 13010021I_ST25.txt; created: Oct. 8, 2018; size: 29,391 bytes) and incorporated herein by reference in its entirety.

BACKGROUND OF THE INVENTION

Field of the Invention

This invention relates to novel 4D5 antibodies that specifically bind HER2/neu, and particularly novel chimeric 4D5 antibodies to HER2/neu, which have reduced glycosylation and altered effector functions as compared to known 4D5 antibodies. The invention also relates to methods of using the antibodies and compositions comprising them in the diagnosis, prognosis and therapy of diseases such as cancer, autoimmune diseases, inflammatory disorders, and infectious disease.

Description of the Related Art

HER2/neu and HER2/neu Receptors

Cellular growth and differentiation processes involve growth factors that exert their actions through specific receptors such as the tyrosine kinases. The binding of ligand to a tyrosine kinase receptor triggers a cascade of events that eventually lead to cellular proliferation and differentiation. (Carpenter et al. (1979) Biochem. 48:193-216; Sachs et al. (1987) Cancer Res. 47:1981-8196). Tyrosine kinase receptors can be classified into several groups on the basis of sequence similarity and distinct features. One such family is the ErbB or epidermal growth factor receptor family, which includes multiple receptors known as HER-1 (also known as erbB-1 or EGFR), HER-2 or HER2/neu (also known as erbB-2, c-neu, or p185), HER-3 (also known as erbB-3), and HER-4 (also known as erbB-4). (See, e.g., Carpenter et al., supra; Semba et al. (1985) Proc. Natl. Acad. Sci. (U.S.A.) 82: 6497-6501; Coussens et al. (1985) Science, 230:1130-1139, Bargmann et al. (1986) Cell 45:649-657; Kraus et al. (1989) PNAS 86: 9193-9197; Carraway et al. (1994) J. Biol. Chem. 269:14303-14306; and Plowman et al. (1993) Nature 366: 473-475; Tzahar et al. (1994) Biol. Chem. 269: 25226-25233).

The ErbB receptors play important roles in propagating signals regulating cell proliferation, differentiation, motility, and apoptosis, both in normal developmental processes and in human tumorigenesis. (Slamon et al. (1989) Science 244:707-712). For example, the activation of erbB receptors is coupled to and stimulates downstream MAPK-Erk1/2 and phosphoinositide-3-kinase ($PI_3K$)/AKT growth and survival pathways. The deregulation of these pathways in cancer has been linked to disease progression and refractoriness to therapy. (Fukazawa et al. (1996) J. Biol. Chem. 271:14554-14559; Tzahar et al. (1996) Mol. Cell. Biol. 16:5276-5287; Lange et al. (1998) J. Biol. Chem. 273:31308-31316; Olayioye et al. (1998) Mol. Cell. Biol. 18:5042-5051; Hackel et al. (1999) Curr. Opin. Cell Biol. 11:184-189). Activation of $PI_3K$/AKT promotes cell survival and enhanced tumor aggressiveness, and AKT2 was reported to be activated and overexpressed in HER2/neu-overexpressing breast cancers. (Shak (1999) Semin. Oncol. Suppl 12:71-77; Huang et al. (2000) Clinical Cancer Res. 7:2166-2174; Bacus et al. (2002) Oncogene 21:3532-3540).

Signaling by the ErbB family of receptors is initiated by ligand binding which triggers homo- or hetero-receptor dimerization, reciprocal tyrosine phosphorylation of the cytoplasmic tails, and activation of intracellular signal transduction pathways. (Citri et al. (2003) Exp. Cell Res. 284:54). The availability of ligands that bind to and activate the ErbB receptors is mediated by various metalloproteases, such as the ADAM (A Disintegrin And Metalloprotease) family of zinc-dependent metalloproteases, which catalyze cell surface ectodomain shedding of specific proteins. (See Chang and Werb (2001) Trends in Cell Biology 11:537-543; Moss and Lambert (2002) Essays in Biochemistry 38:141-153; Seals and Courtneidge (2003) Genes and Development 17:7-30). Specifically, the ADAM family has been shown to cleave ligands responsible for activating the ErbB receptors, such as APP and Notch. (Blobel (2005) Nat. Rev. Mol. Cell. Biol. 6:32-43).

An important member of the ErbB family, HER2/neu, is a 185 kDa receptor protein that was originally identified as the product of the transforming gene from neuroblastomas of chemically treated rats. HER2/neu has been extensively investigated because of its role in several human carcinomas and in mammalian development. (Hynes and Stern (1994) Biochim. et Biophys. Acta 1198:165-184; and Dougall et al. (1994) Oncogene 9:2109-2123; Lee et al. (1995) Nature 378:394-398). The human HER2/neu gene and HER2/neu protein are described in Semba et al. (1985) Proc. Natl. Acad. Sci. (U.S.A.) 82:6497-6501 and Yamamoto et al. (1986) Nature 319:230-234, and the sequence is available in GenBank as accession number X03363. HER2/neu comprises four domains: an extracellular domain to which ligand binds; a lipophilic transmembrane domain; a conserved intracellular tyrosine kinase domain; and a carboxyl-terminal signaling domain harboring several tyrosine residues that can be phosphorylated. (Plowman et al. (1993) Proc. Natl. Acad. Sci. (U.S.A.) 90:1746-1750). The sequence of the HER2/neu extracellular (ECD) domain was described by Franklin et al. (2004) Cancer Cell. 5(4):317-328, and is available in Protein DataBank Record 1S78 (2004).

HER2/neu functions as a growth factor receptor and is often expressed by tumors such as breast cancer, ovarian cancer and lung cancer. HER2/neu is overexpressed in 25-30% of human breast and ovarian cancers, and is associated with aggressive clinical progression and poor prognosis in these patients. (Slamon et al. (1987) Science 235: 177-182; Slamon et al. (1989) Science 244:707-712). Overexpression of HER2/neu has also been observed in other carcinomas including carcinomas of the stomach, endometrium, salivary gland, lung, kidney, colon, thyroid, pancreas and bladder. (See, e.g., King et al. (1985) Science 229:974; McCann et al. (1990) Cancer 65:88-92; Yonemura et al. (1991) Cancer Research 51:1034).

Activation of HER2/neu has been correlated with reduced clinical responsiveness to hormone therapy in breast cancer patients. (Wright et. al. (1989) Cancer Res. 49:2087-2090; Kurokawa & Arteaga (2001) Clin. Cancer Res. 7:4436s-42s, 4411s-4412s). Indeed, HER2/neu expression is sufficient to convey anti-estrogen resistance. (Benz et. al. (1993) Breast Cancer Res. Treat. 24:85-95). HER2/neu, as well as HER-3, also appears to be involved in the onset of hormone resistance in prostate cancer patients. Approximately one-third of prostate cancer patients receive hormone therapy treatment aimed at disrupting the action of testicular and adrenal androgens. As with breast cancer, resistance is inevitable. Recent data suggests that signals emanating from HER2/neu and HER-3 induce a "hormone-refractory" state. (Mellinghoff et. al. (2004) Cancer Cell 6:517-527).

Several truncated and spliced versions of HER2/neu are known. For example, a truncated ECD located in the perinuclear cytoplasm of some gastric carcinoma cells is produced by an alternative transcript generated by use of a polyadenylation signal within an intron. (Yamamoto et al. (1986) Nature 319:230-234; and Scott et al. (1993) Mol. Cell. Biol. 13:2247-2257). No particular therapeutic, diagnostic or research utility has been ascribed to this truncated ECD polypeptide. The ECD of HER2/neu can also be proteolytically shed from breast carcinoma cells in culture, and is found in the serum of some cancer patients where it is may be a serum marker of metastatic breast cancer and overall poor prognosis. (Petch et al. (1990) Mol. Cell. Biol. 10:2973-2982; Leitzel et al. (1992) J. Clin. Oncol. 10:1436-1443; Scott et al. (1993) Mol. Cell. Biol. 13:2247-2257; and Lee and Maihle (1998) Oncogene 16:3243-3252). In some HER2/neu overexpressing tumor cells, 4-aminophenylmercuric acetate (APMA), a well-known metalloprotease activator, activates metalloproteases such as ADAM10 and ADAM15 to cleave the HER2/neu receptor into two parts: a truncated membrane-associated receptor known as p95, and a soluble ECD known as p105 or ECD105. (See, e.g., Molina et al. (2001) Cancer Res. 61:4744-4749; U.S. Patent Publication No. 2004/0247602). Loss of the ECD renders the p95 receptor a constitutively active tyrosine kinase, which can deliver growth and survival signals to cancer cells. (See, e.g., U.S. Pat. No. 6,541,214).

Studies have shown that in HER2/neu overexpressing breast cancer cells, treatment with antibodies specific to HER2/neu in combination with chemotherapeutic agents (e.g., cisplatin, doxoubicin, taxol) elicits a higher cytotoxic response than treatment with chemotherapy alone. (Hancock et al. (1991) Cancer Res. 51:4575-4580; Arteaga et al. (1994) Cancer 54:3758-3765; Pietras et al. (1994) Oncogene 9:1829-1838). One possible mechanism by which HER2/neu antibodies might enhance response to chemotherapeutic agents is through the modulation of HER2/neu protein expression or by interfering with DNA repair. (Stancovski et al. (1991) Proc. Natl. Acad. Sci. (U.S.A.) 88:8691-8695; Bacus et al. (1992) Cell Growth & Diff. 3:401-411; Bacus et al. (1993) Cancer Res. 53:5251-5261; Klapper et al. (1997) Oncogene 14:2099-2109; Klapper et al. (2000) Cancer Res. 60:3384-3388; Arteaga et al. (2001) J Clinical Oncology 19(18s):32s-40s).

A number of monoclonal antibodies and small molecule tyrosine kinase inhibitors targeting HER-1 or HER2/neu have been developed. For example, a murine monoclonal antibody known as 4D5 recognizes an extracellular epitope (amino acids 529 to 627) in the cysteine-rich II domain of HER2/neu that resides very close to the transmembrane region. Treatment of breast cancer cells with 4D5 partially blocks NDF/heregulin activation of HER2/neu-HER-3 complexes, as measured by receptor phosphorylation assays. (Carter et al. (1992) Proc. Natl. Acad. Sci. (U.S.A.) 89:4285-4289; Sliwkowski et al. (1999) Sem. in Oncol. 26:60-70; Ye et al. (1999) Oncogene 18:731-738; Vogel et al. (2001) Oncology 61(suppl 2):37-42; Vogel et al. (2002) Journal of Clinical Oncology 20(3):719-726; Fujimoto-Ouchi et al. (2002) Cancer Chemother. Pharmacol. 49:211-216). Administration of 4D5 to humans, however, was a clinical failure because patients quickly developed HAMA responses, so humanized forms were developed. The sequence and crystal structure of humanized antibody 4D5 have been described in U.S. Pat. No. 6,054,297, Carter et al., supra, and Eigenbrot et al. (1993) J. Mol. Biol. 229:969-95.

A humanized form of 4D5 known as trastuzumab (sold as Herceptin® by Genentech, Inc.) was developed and approved for treating cancers involving the overexpression or gene amplification of HER2/neu, including breast cancer. (Cobleigh et al. (1999) J. Clin. Oncol. 17:2639-2648). Trastuzumab inhibits the APMA-mediated cleavage of HER2/neu into the ECD and p95 portions in vitro, and is believed to work in vitro through different mechanisms, including the possible inhibition of HER2/neu shedding. (Pegram et al. (1998) Journal of Clinical Oncology 16(8): 2659-2671; Baselga et al. (2001) Seminars in Oncology 28(5)(suppl. 16):4-11; Baselga et al. (2001) Annals of Oncology 12 (suppl. 1):535-541). Trastuzumab therapy has various drawbacks, however, such as cardiotoxicity and development of HAHA responses in some patients.

Thus, there is still a need for new or improved forms of HER2/neu antibodies for use in cancer therapies, for example 4D5 antibodies having increasing affinity or specificity, reduced potential for HAMA or HAHA responses, altered effector functions, and the like.

Fc Receptors

The interaction of antibody-antigen complexes with cells of the immune system results in a wide array of responses, ranging from effector functions such as antibody-dependent cytotoxicity, mast cell degranulation, and phagocytosis to immunomodulatory signals such as regulating lymphocyte proliferation and antibody secretion. All these interactions are initiated through the binding of the Fc domain of antibodies or immune complexes to Fc receptors, which are specialized cell surface receptors on hematopoietic cells. The diversity of cellular responses triggered by antibodies and immune complexes results from the structural heterogeneity of Fc receptors. Fc receptors share structurally related ligand binding domains which presumably mediate intracellular signaling.

The Fc receptors, members of the immunoglobulin gene superfamily of proteins, are surface glycoproteins that can bind the Fc portion of immunoglobulin molecules. Each member of the family recognizes immunoglobulins of one or more isotypes through a recognition domain on the a chain of the Fc receptor. Fc receptors are defined by their specificity for immunoglobulin subtypes. Fc receptors for IgG are referred to as "FcγR," for IgE as "FεR," and for IgA as "FcαR." Different accessory cells bear Fc receptors for antibodies of different isotype, and the isotype of the antibody determines which accessory cells will be engaged in a given response (Billadeau et al. (2002) J. Clin. Investigat. 2 (109):161-81; Gerber et al. (2001) Microbes Infection 3:131-139; Ravetch et al. (2001) Annu. Rev. Immunol. 19:275-90; Ravetch et al. (2000) Science 290:84-89; Ravetch (1994) Cell 78(4):553-560; Ravetch et al. (1991) Annu. Rev. Immunol. 9:457-492; see also, Immunobiology: The Immune System in Health and Disease (4th ed. 1999), Elsevier Science Ltd/Garland Publishing, New York). An overview of various receptors is presented in Table 1.

TABLE 1

Receptors for the Fc Regions of Immunoglobulin Isotypes

| Receptor | Binding | Cell Type | Effect of Ligation |
|---|---|---|---|
| FcγRI (CD64) | IgG1 $10^8$ $M^{-1}$ | Macrophages Neutrophils Eosinophils Dendritic cells | Uptake Stimulation Activation of respiratory burst Induction of killing |
| FcγRII-A (CD32) | IgG1 $2 \times 10^6$ $M^{-1}$ | Macrophages Neutrophils Eosinophils Dendritic cells Platelets Langerhan cells | Uptake Granule release |
| FcγRII-B1 (CD32) | IgG1 $2 \times 10^6$ $M^{-1}$ | B cells Mast cells | No uptake Inhibition of Stimulation |
| FcγRII-B2 (CD32) | IgG1 $2 \times 10^6$ $M^{-1}$ | Macrophages Neutrophils Eosinophils | Uptake Inhibition of Stimulation |
| FcγRIII (CD16) | IgG1 $5 \times 10^5$ $M^{-1}$ | NK cells Eosinophils Macrophages Neutrophils Mast Cells | Induction of Killing |
| FcεRI | IgE $10^{10}$ $M^{-1}$ | Mast cells Eosinophil Basophils | Secretion of granules |
| FcαRI (CD89) | IgA1, IgA2 $10^7$ $M^{-1}$ | Macrophages Neutrophils Eosinophils | Uptake Induction of killing |

Each Fcγ receptor ("FcγR") is an integral membrane glycoprotein, possessing extracellular domains related to a C2-set of immunoglobulin-related domains, a single membrane spanning domain and an intracytoplasmic domain of variable length. There are four known FcγRs, designated FcγRI (CD64), FcγRII (CD32), FcγRIII (CD16), and FcγRIV. The receptors are encoded by distinct genes; however, the extensive homology between the family members suggest they arose from a common progenitor perhaps by gene duplication.

Both activating and inhibitory signals are transduced through the FcγRs following ligation. These diametrically opposing functions result from structural differences among the different receptor isoforms. Two distinct domains within the cytoplasmic signaling domains of the receptor called immunoreceptor tyrosine based activation motifs (ITAMs) or immunoreceptor tyrosine based inhibitory motifs (ITIMS) account for the different responses. The recruitment of different cytoplasmic enzymes to these structures dictates the outcome of the FcγR-mediated cellular responses. ITAM-containing FcγR complexes include FcγRI, FcγRIIA, FcγRIIIA, and FcγRIV, whereas ITIM-containing complexes only include FcγRIIB.

FcγRI displays high affinity for the antibody constant region and restricted isotype specificity (Hulett and Hogarth (1994) Adv Immunol 57:1-127). FcγRII proteins are 40 KDa integral membrane glycoproteins which bind only the complexed IgG due to a low affinity for monomeric Ig ($10^6$ $M-1$). This receptor is the most widely expressed FcγR, present on all hematopoietic cells, including monocytes, macrophages, B cells, NK cells, neutrophils, mast cells, and platelets. FcγRII has only two immunoglobulin-like regions in its immunoglobulin binding chain and hence a much lower affinity for IgG than FcγRI. There are three known human FcγRII genes (FcγRII-A, FcγRII-B, FcγRII-C), all of which bind IgG in aggregates or immune complexes. Human neutrophils express the FcγRIIA gene. The FcγRIIB gene is expressed on B lymphocytes; its extracellular domain is 96% identical to FcγRIIA and binds IgG complexes in an indistinguishable manner.

Distinct differences within the cytoplasmic domains of FcγRII-A and FcγRII-B create two functionally heterogenous responses to receptor ligation. The FcγRII-A isoform initiates intracellular signaling leading to cell activation such as phagocytosis and respiratory burst, whereas the FcγRII-B isoform initiates inhibitory signals, e.g., inhibiting B-cell activation. FcγRIIA clustering via immune complexes or specific antibody cross-linking serves to aggregate ITAMs along with receptor-associated kinases which facilitate ITAM phosphorylation. ITAM phosphorylation serves as a docking site for Syk kinase, activation of which results in activation of downstream substrates (e.g., PI3K). Cellular activation leads to release of proinflammatory mediators. When co-ligated or co-aggregated along with an activating FcγR having an ITAM, such as FcγRIIA or FcεRI, the ITIM in FcγRIIB becomes phosphorylated and recruits the SH2 domain of the src homology 2-containing inositol phosphatase (SHIP), which in turn is phosphorylated and associates with Shc (Ott (2002) J. Immunol. 162(9):4430-4439; Yamanshi et al. (1997) Cell 88:205; Carpino et al. (1997) Cell 88:197). SHIP hydrolyzes phosphoinositol messengers released as a consequence of ITAM-containing FcγR-mediated tyrosine kinase activation, consequently preventing the influx of intracellular Ca++, and dampening cellular responsiveness to FcγR ligation. Thus, B cell activation, B cell proliferation and antibody secretion is aborted, and FcγR-mediated phagocytosis is down-regulated (Tridandapani et al. (2002) J. Biol. Chem. 277(7):5082-89).

Specifically, coaggregation of FcγRIIA with FcγRIIB results in down-regulation of phosphorylation of Akt, which is a serine-threonine kinase that is involved in cellular regulation and serves to suppress apoptosis, and coaggregation of FcγRIIB with the high affinity IgE receptor FcεRI in mast cells leads to inhibition of antigen-induced degranulation, calcium mobilization, and cytokine production (Long (1999) Annu Rev. Immunol 17:875; Metcalfe et al. (1997) Physiol. Rev. 77:1033). Coaggregation of FcγRIIB and the B-cell receptor (BCR) leads to inhibition of BCR-mediated signaling, and inhibition of cell cycle progression and cellular survival. Although numerous effector functions of FcγRIIB-mediated inhibition of BCR signaling are mediated through SHIP, recently it has been demonstrated that lipopolysaccharide (LPS)-activated B cells from SHIP deficient mice exhibit significant FcγRIIB-mediated inhibition of calcium mobilization, Ins(1,4,5)P3 production, and Erk and Akt phosphorylation (Brauweiler et al. (2001) Journal of Immunology 167(1): 204-211).

The size of FcγRIII ranges between 40 and 80 kDa in mouse and man, due to heterogeneity within this class. Two human genes encode two transcripts, FcγRIIIA, an integral membrane glycoprotein, and FcγRIIIB, a glycosylphosphatidyl-inositol (GPI)-linked version. One murine gene encodes an FcγRIII homologous to the membrane spanning human FcγRIIIA. The FcγRIII shares structural characteristics with each of the other two FcγRs. Like FcγRII, FcγRIII binds IgG with low affinity and contains the corresponding two extracellular Ig-like domains FcγRIIIA is expressed in macrophages, mast cells, and is the lone FcγR in NK cells. The GPI-linked FcγRIIIB is currently known to be expressed only in human neutrophils.

FcγRIV (also known as mFcRIV) requires association of the FcR gamma-chain for optimal expression and function on myeloid cells; its signaling potential is also enhanced by a cytoplasmic "YEEP" motif that recruits the adaptor molecule Crk-L and phosphatidylinositol-3-OH kinase. FcγRIV preferentially binds immunoglobulin E antibodies of the b allotype (IgEb) as well as IgG2a and IgG2b antibodies. Ligation of FcγRIV by antigen-IgEb immune complexes promotes macrophage-mediated phagocytosis, presentation of antigen to T cells, production of proinflammatory cytokines and the late phase of cutaneous allergic reactions (Hirano et al. (2007) Nature Immunology 8:762-771). FcγRIV is a recently identified receptor, conserved in all mammalian species with intermediate affinity and restricted subclass specificity (Nimmerjahn et al. (2005) Immunity 23:41-51; Mechetina et al. (2002) Immunogenetics 54:463-468; Davis et al. (2002) Immunol Rev 190:23-36). FcRIII and FcRIV are physiologically important activation FcRs for mediating inflammatory disease triggered by cytotoxic antibodies or pathogenic immune complexes. FcRIV is found on dendritic cells, macrophages, monocytes and neutrophils.

Despite all such advances, a need remains for anti-HER2/neu antibodies that possess therapeutic use in the treatment of autoimmunity, cancer, inflammatory disease, and/or transplantation, and exhibit improved ability to mediate effector function from the Fc receptors. The present invention is directed to this and other needs.

SUMMARY OF THE INVENTION

Embodiments of the invention provide various polypeptides, for example a polypeptide comprising an immunoglobulin light chain variable domain having the amino acid sequence of SEQ ID NO: 4, a polypeptide comprising an immunoglobulin light chain having the amino acid sequence of SEQ ID NO: 2, and a polypeptide comprising a chimeric 4D5 immunoglobulin light chain comprising an N65S substitution. Other embodiments provide a polypeptide comprising an immunoglobulin heavy chain having the amino acid sequence of SEQ ID NO: 7, a polypeptide comprising an immunoglobulin heavy chain having an amino acid sequence selected from the group consisting of SEQ ID NO: 9, SEQ ID NO: 11, and SEQ ID NO: 13, and a polypeptide comprising a 4D5 immunoglobulin heavy chain comprising various substitutions.

The polypeptides may be antibodies, and may specifically bind human HER2/neu. The polypeptides and antibodies may comprise a variant Fc domain, which comprises one or more modifications, which may confer a phenotype alteration on the polypeptide or antibody, including altered effector function, increased or decreased binding to an FcγR, etc. The embodiments of the invention also provide polynucleotides encoding the polypeptides and antibodies, vectors comprising the polynucleotides, and host cells comprising the vectors. Methods of producing the polypeptides and antibodies, as well as methods of treating various diseases and disorders, are also provided.

In detail, the invention provides a polypeptide comprising a chimeric 4D5 immunoglobulin light chain comprising an N65S substitution, and particularly the embodiments of such polypeptide wherein the polypeptide comprises a light chain variable domain having the amino acid sequence of SEQ ID NO: 4 or of SEQ ID NO: 2.

The invention particularly concerns the embodiments of such polypeptides wherein the polypeptide is an antibody, and more particularly, an antibody that comprises a variant Fc domain having at least one modification in the Fc domain. The invention particularly concerns embodiments wherein the modification comprises at least one substitution selected from the group consisting of L235V, F243L, R292P, Y300L, V305I, and P396L.

The invention further concerns the embodiments of such antibodies wherein the modification in the Fc domain comprises:
 (A) at least one substitution selected from the group consisting of F243L, D270E, R292P, S298N, Y300L, V305I, A330V, and P396L;
 (B) at least two substitutions selected from the group consisting of F243L and P396L; F243L and R292P; and R292P and V305I;
 (C) at least three substitutions selected from the group consisting of F243L, R292P and Y300L; F243L, R292P and V305I; F243L, R292P and P396L; and R292P, V305I and P396L; or
 (D) at least four substitutions selected from the group consisting of F243L, R292P, Y300L and P396L; and F243L, R292P, V305I and P396L;
and more particularly concerns antibodies wherein the modification in the Fc domain comprises:
 (1) F243L, R292P, and Y300L;
 (2) L235V, F243L, R292P, Y300L, and P396L; or
 (3) F243L, R292P, Y300L, V305I, and P396L.

The invention further concerns the embodiments of such antibodies wherein the variant Fc domain exhibits, as compared to a wild-type Fc domain:
 (A) enhanced antibody dependent cell mediated cytotoxicity (ADCC);
 (B) increased binding to FcγRIIA or to FcγRIIIA;
 (C) decreased binding to FcγRIIB; or
 (D) increased binding to FcγRIIB.

The invention further concerns a polypeptide comprising an immunoglobulin heavy chain comprising a variable domain having an amino acid sequence selected from the group consisting of SEQ ID NO: 9, SEQ ID NO: 11, and SEQ ID NO: 13.

The invention further concerns a polypeptide comprising a 4D5 immunoglobulin heavy chain comprising:
 (A) at least one substitution selected from the group consisting of: F243L, D270E, R292P, S298N, Y300L, V305I, A330V and P396L;
 (B) at least two substitutions selected from the group consisting of:
  (1) F243L and P396L;
  (2) F243L and R292P; and
  (3) R292P and V305I;
 (C) at least three substitutions selected from the group consisting of:
  (1) F243L, R292P and Y300L;
  (2) F243L, R292P and V305I;
  (3) F243L, R292P and P396L; and
  (4) R292P, V305I and P396L;
 (D) at least four substitutions selected from the group consisting of:
  (1) F243L, R292P, Y300L and P396L; and
  (2) F243L, R292P, V305I and P396L;
 or
 (E) at least F243L, R292P, Y300L, V305I and P396 substitutions.

The invention further concerns the embodiment of such a polypeptide wherein the polypeptide is an antibody.

The invention further concerns the embodiment of the above-described antibodies, wherein the antibody further comprises an immunoglobulin heavy chain comprising a variable domain having the amino acid sequence of SEQ ID NO: 7, SEQ ID NO: 9, SEQ ID NO: 11, or SEQ ID NO: 13.

The invention further concerns the embodiment of the above-described antibodies, wherein the antibody comprises:
(A) at least one substitution selected from the group consisting of: F243L, D270E, R292P, S298N, Y300L, V305I, A330V and P396L;
(B) at least two substitutions selected from the group consisting of:
  (1) F243L and P396L;
  (2) F243L and R292P; and
  (3) R292P and V305I;
(C) at least three substitutions selected from the group consisting of:
  (1) F243L, R292P and Y300L;
  (2) F243L, R292P and V305I;
  (3) F243L, R292P and P396L; and
  (4) R292P, V305I and P396L;
(D) at least four substitutions selected from the group consisting of:
  (1) F243L, R292P, Y300L and P396L; and
  (2) F243L, R292P, V305I and P396L;
or
(E) at least F243L, R292P, Y300L, V305I and P396 substitutions.

The invention further concerns the embodiments of the above-described antibodies wherein the immunoglobulin light chain comprises a variable domain having the amino acid sequence of SEQ ID NO: 4 and the immunoglobulin heavy chain comprises an amino acid sequence of SEQ ID NO: 9, SEQ ID NO: 11 or SEQ ID NO:13.

The invention further concerns the embodiments of the above-described antibodies wherein the antibody is a F(ab')$_2$ fragment, a F(ab) fragment, a single chain antibody, a monoclonal antibody or a diabody.

The invention further concerns the use of the above-described antibodies in the manufacture of a medicament for the treatment of cancer in a patient, and particularly, wherein the cancer is a HER2/neu-expressing cancer and wherein the antibody binds human HER2/neu.

The invention further concerns a method of treating cancer which comprises providing to a patient in need thereof an effective amount of the above-described antibodies, and particularly, wherein the cancer is a HER2/neu-expressing cancer and wherein the antibody binds human HER2/neu.

The invention further concerns the use of such antibodies wherein the treatment further comprises the step of administering a second therapeutic agent simultaneously or sequentially with the antibody, wherein the second therapeutic agent is selected from the group consisting of an anti-angiogenic agent, an anti-neoplastic agent, a chemotherapeutic agent, and a cytotoxic agent.

Additional advantages and features of the present invention will be apparent from the following detailed description, drawings and examples, which illustrate preferred embodiments of the invention.

BRIEF DESCRIPTION OF THE DRAWINGS

FIG. 1 depicts a sequence alignment comparing the sequences of the light chain variable region of a chimeric 4D5 antibody of a preferred embodiment (SEQ ID NO: 4) with murine (SEQ ID NO: 3) and humanized (SEQ ID NO: 5) 4D5 antibodies.

FIG. 2 depicts a comparison between the sequences of the heavy chains of ch4D5-wild-type Fc ("WT") (SEQ ID NO: 7), ch4D5-FcMT1 ("MT1") (SEQ ID NO: 9), ch4D5-FcMT2 ("MT2") (SEQ ID NO: 11), and ch4D5-FcMT3 ("MT3") (SEQ ID NO: 13). The CDRs are indicated with black bars shown underneath the pertinent residues.

FIG. 4 depicts the effect of ch4D5 on the proliferation of SKBR3 cells in vitro.

FIG. 10 depicts the results of ADCC assays performed to test the ability of various ch4D5 antibodies of the present embodiments to mediate ADCC in cancer cell lines (MDA-MB-435 in Panel A; MDA-MB-231 in Panel B) having very low or no HER2/neu expression levels (DAKO score of 0).

FIG. 12 depicts the results of ADCC assays performed to test the ability of various ch4D5 antibodies of the present embodiments to mediate ADCC in cancer cell lines (ZR75-1 in Panel A; JIMT-1 in Panel B) having moderate HER2/neu expression levels (DAKO score of 2+).

DETAILED DESCRIPTION OF THE INVENTION

Figure 3:
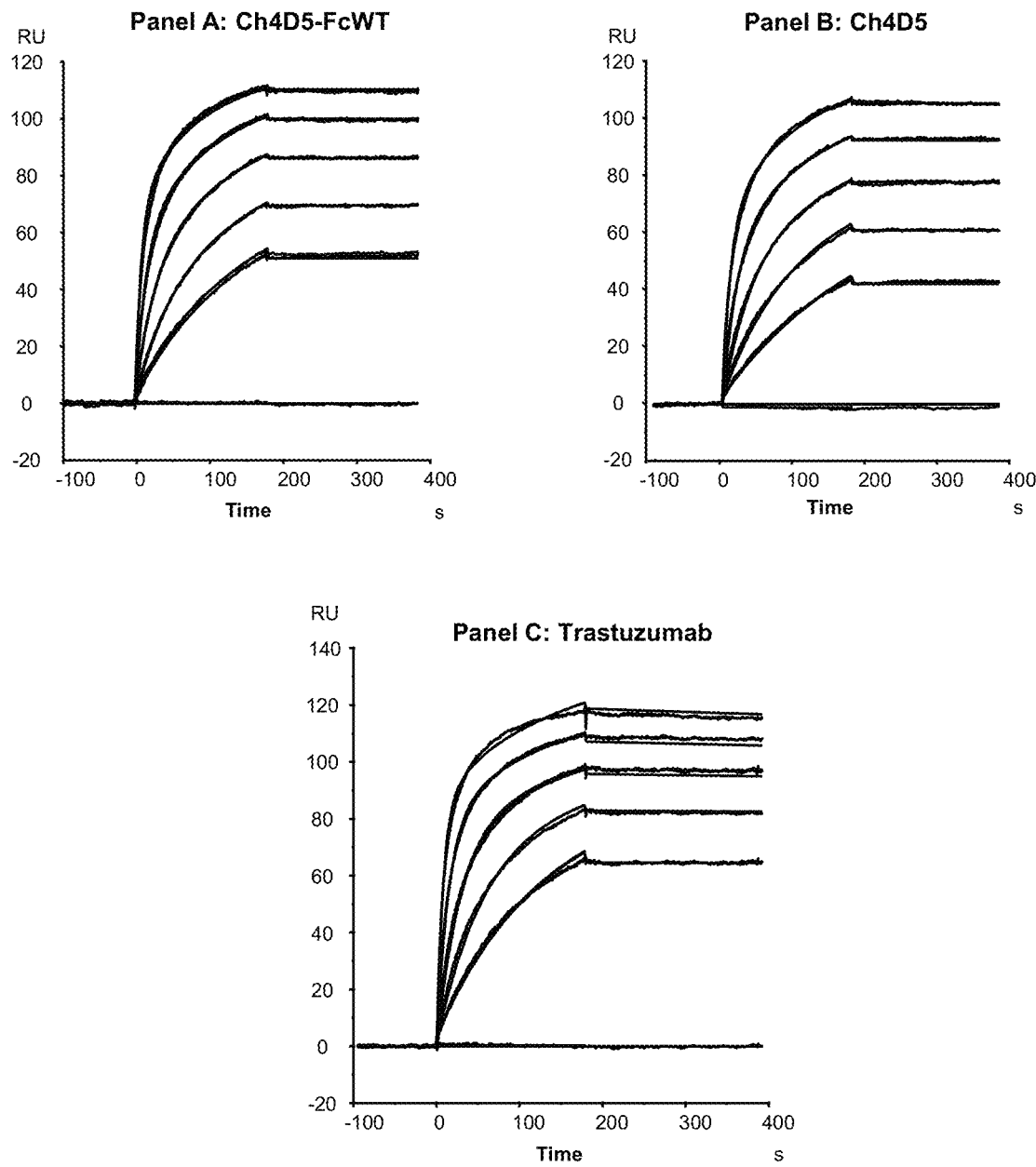
FIG. 3 depicts a BIACore analysis of ch4D5-wild-type Fc (panel A), ch4D5 (panel B) and trastuzumab (panel C) binding.

The present invention provides novel antibodies and methods for treatment, diagnosis and prognosis for certain cancers using antibodies against HER2/neu. In particular, the present invention provides anti-HER2/neu antibodies that are particularly useful as selective cytotoxic agents for HER2/neu overexpressing cells, for example chimeric 4D5 antibodies to HER2/neu, which have reduced glycosylation and altered effector functions as compared to known 4D5 antibodies. The invention also provides methods of using the antibodies and compositions comprising them in the diagnosis, prognosis and therapy of diseases such as cancer, autoimmune diseases, inflammatory disorders, and infectious disease.

Reference will now be made in detail to the presently preferred embodiments of the invention, which, together with the drawings and the following examples, serve to explain the principles of the invention. These embodiments are described in sufficient detail to enable those skilled in the art to practice the invention, and it is to be understood that other embodiments may be utilized, and that structural, biological, and chemical changes may be made without departing from the spirit and scope of the present invention. Unless otherwise defined, all technical and scientific terms used herein have the same meaning as commonly understood by one of ordinary skill in the art to which this invention belongs. One skilled in the art may refer to general reference texts for such definitions or for detailed descriptions of techniques discussed herein. These texts include Current Protocols in Molecular Biology (Ausubel et al., eds., John Wiley & Sons, and supplements through March 2008), Molecular Cloning: A Laboratory Manual (Sambrook and Russell, 3rd ed., 2001); Single-Molecule Techniques: A Laboratory Manual (Selvin & Ha, eds., Cold Spring Harbor Press, 2008); Current Protocols in Nucleic Acid Chemistry (Beaucage et al., eds., John Wiley & Sons, Inc., 2000); Current Protocols in Immunology (Coligan et al., eds., John Wiley & Sons, N.Y., and supplements through March 2008), Making and Using Antibodies: A Practical Handbook (Howard & Kaser, eds., CRC, 2006); Using Antibodies: A Laboratory Manual (Harlow & Lane, Cold Spring Harbor Press, 1999); Binding and Kinetics for Molecular Biologists (Goodrich & Kugel, Cold Spring Harbor Press, 2007); Current Protocols in Pharmacology (Enna et al., eds., John Wiley & Sons, N.Y., and supplements through March 2008), The Pharmacological Basis of Therapeutics (Goodman & Gilman, 11th ed., 2006), and Remington: The Science and Practice of Pharmacy (Lippincott Williams & Wilkins, 21st edition (2005), for example.

A. Definitions

As used herein, the term "ADCC" refers to Antibody Dependent Cellular Cytotoxicity, an in vitro cell-mediated reaction in which nonspecific cytotoxic cells that express FcγRs (e.g., monocytic cells such as Natural Killer (NK) cells and macrophages) recognize bound antibody on a target cell and subsequently cause lysis of the target cell.

As used herein, the term "antibody" refers to monoclonal antibodies, multispecific antibodies, human antibodies, humanized antibodies, synthetic antibodies, chimeric antibodies, polyclonal antibodies, camelized antibodies, single-chain Fvs (scFv), single chain antibodies, immunologically active antibody fragments (e.g., antibody fragments capable of binding to an epitope, e.g., Fab fragments, Fab' fragments, F(ab')2 fragments, Fv fragments, fragments containing either a VL or VH domain or a complementary determining region (CDR) that immunospecifically binds an antigen, etc.), bi-functional or multi-functional antibodies, disulfide-linked bispecific Fvs (sdFv), intrabodies, and diabodies, and epitope-binding fragments of any of the above. In particular, the term antibodies is intended to encompass immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass (see, e.g., United States Patent Publication Nos.: 20040185045; 20050037000; 20050064514; 20050215767; 20070004909; 20070036799; 20070077246; and 20070244303).

Reference to a "B cell antigen receptor" or "BCR" is intended to reference the B cell antigen receptor, which includes a membrane immunoglobulin (mIg) antigen binding component, or a biologically active portion thereof (i.e, a portion capable of binding a ligand and/or capable of associating with a transducer component), and transducer CD79a and CD79b components, or biologically active portions thereof (i.e., a portion capable of transducing an intracellular signal and/or capable of associating with an extracellular ligand binding portion).

As used herein, the term "cancer" refers to a neoplasm or tumor resulting from abnormal uncontrolled growth of cells. As used herein, cancer explicitly includes, leukemias and lymphomas. In some embodiments, cancer refers to a benign tumor, which has remained localized. In other embodiments, cancer refers to a malignant tumor, which has invaded and destroyed neighboring body structures and spread to distant sites. In some embodiments, the cancer is associated with a specific cancer antigen.

The terms "cell proliferative disorder" and "proliferative disorder" refer to disorders that are associated with some degree of abnormal cell proliferation. In one embodiment, the cell proliferative disorder is cancer.

The term "chimeric," when referring to antibodies, refers to an antibody in which a portion of a heavy and/or light chain is identical to or homologous with an antibody from one species (e.g., mouse) or antibody class or subclass, while the remaining portion is identical to or homologous with an antibody of another species (e.g., human) or antibody class or subclass, so long as they exhibit the desired biological activity. Chimeric antibodies of interest herein include "primatized" antibodies comprising variable domain antigen-binding sequences derived from a non-human primate (e.g., Old World Monkey, Ape, etc.) and human constant region sequences.

As used herein, the term "Complementarity Determining Region" or "CDR" refers to the amino acid residues of an antibody variable domain that are necessary for antigen binding. Each variable domain typically has three CDR regions identified as $CDR_1$, $CDR_2$ and $CDR_3$.

As used herein, the term "diabody molecule" refers to a complex of two or more polypeptide chains or proteins, each comprising at least one $V_L$ and one $V_H$ domain or fragment thereof, wherein both domains are comprised within a single polypeptide chain. In certain embodiments a "diabody molecule" includes molecules comprising an Fc or a hinge-Fc domain. Said polypeptide chains in the complex may be the same or different, i.e., the diabody molecule may be a homo-multimer or a hetero-multimer. In specific aspects, a "diabody molecule" includes dimers or tetramers or said polypeptide chains containing both a $V_L$ and $V_H$ domain. The individual polypeptide chains comprising the multimeric proteins may be covalently joined to at least one other peptide of the multimer by interchain disulfide bonds.

As used herein, the terms "disorder" and "disease" are used interchangeably to refer to a condition in a subject. In particular, the term "autoimmune disease" is used interchangeably with the term "autoimmune disorder" to refer to a condition in a subject characterized by cellular, tissue and/or organ injury caused by an immunologic reaction of the subject to its own cells, tissues and/or organs. The term "inflammatory disease" is used interchangeably with the term "inflammatory disorder" to refer to a condition in a subject characterized by inflammation, preferably chronic inflammation. Autoimmune disorders may or may not be associated with inflammation. Moreover, inflammation may or may not be caused by an autoimmune disorder. Thus, certain disorders may be characterized as both autoimmune and inflammatory disorders.

The term "effector cell" as used herein refers to a cell of the immune system that expresses one or more Fc receptors and mediates one or more effector functions. Effector cells include but are not limited to monocytes, macrophages, neutrophils, dendritic cells, eosinophils, mast cells, platelets, B cells, large granular lymphocytes, Langerhans' cells, natural killer (NK) cells, and may be from any organism including but not limited to humans, mice, rats, rabbits, and monkeys.

The term "effector cell" refers to biological activities attributable to the interaction of an antibody Fc region with an Fc receptor or ligand. An antibody may have one or more effector functions. Non-limiting examples of antibody effector functions include antibody-dependent cell-mediated cytotoxicity (ADCC), C1q binding, complement dependent cytotoxicity (CDC), down regulation of cell surface receptors (e.g., B-cell receptor; BCR), opsonization, opsonophagocytosis, cell binding, and rosetting. Effector functions include both those that operate after the binding of an antigen and those that operate independent of antigen binding.

As used herein, the term "epitope" refers to that portion of a polypeptide or protein or a non-protein molecule that is immunospecifically bound by an antibody. An epitope may have immunogenic activity, such that it elicits an antibody production response in an animal. The ability of an epitope to immunospecifically bind an antibody may be determined by for example, an immunoassay. Epitopes need not necessarily be immunogenic.

The terms "Fc receptor" or "FcR" are used herein to describe a receptor that binds to the Fc region of an antibody. An exemplary FcR is a native sequence human FcR. An FcR may be one which binds an IgG antibody (a gamma receptor) and includes receptors of the FcγRI, FcγRII, FcγRIII, and FcγRIV subclasses, including allelic variants and alternatively spliced forms of these receptors, e.g., there are at least two known FcγRII receptors, FcγRIIA and FcγRIIB. The term FcR also includes the neonatal receptor, FcRn, which is responsible for the transfer of maternal IgGs to the fetus.

As used herein, the term "Fc region" is used to define a C-terminal region of an IgG heavy chain. Although the boundaries may vary slightly, the human IgG heavy chain Fc region is defined to stretch from Cys226 to the carboxy terminus. The Fc region of an IgG comprises two constant domains, $C_{H2}$ and $C_{H3}$. The $C_{H2}$ domain of a human IgG Fc region (also referred to as "Cγ2" domain) usually extends from amino acid 231 to amino acid 338, and the $C_{H3}$ domain of a human IgG Fc region usually extends from amino acids 342 to 447.

The term "glycosylation site" refers to an amino acid residue or residues that is recognized by a mammalian cell as a location for the attachment of sugar residues. Amino acid residues to which carbohydrates, such as oligosaccharides, are attached are usually asparagine (N-linkage), serine (O-linkage), and threonine (O-linkage) residues. The specific sites of attachment usually have a characteristic sequence of amino acids, referred to as a "glycosylation site sequence." The glycosylation site sequence for N-linked glycosylation is: Asn-X-Ser/Thr, where X can be any of the conventional amino acids other than proline. The Fc region of human IgG has two N-linked glycosylation sites, one in each of the $C_{H2}$ domains, at the asparagine at position 297 (Asn 297).

As used herein, the term "HAMA response" refers to the Human Anti-Mouse Antibody response, which is a deleterious immunogenic response that occurs when a human immune system recognizes a murine antibody as foreign and attacks it. A HAMA response can cause toxic shock or death. Chimeric and humanized antibodies reduce the likelihood of a HAMA response by decreasing the non-human portions of administered antibodies, but there is still potential for a Human Anti-Human Antibody response ("HAHA response") immune response to such antibodies.

The terms "heavy chain," "light chain" ("CL"), "light chain variable region" ("VL"), "heavy chain variable region" ("VH"), "framework region" ("FR"), "heavy chain constant domain" ("CH"), "light chain constant domain" ("CL") refer to domains in naturally occurring immunoglobulins and the corresponding domains of synthetic (e.g., recombinant) binding proteins (e.g., humanized antibodies). The basic structural unit of naturally occurring immunoglobulins (e.g., IgG) is a tetramer having two light chains and two heavy chains. Usually naturally occurring immunoglobulin is expressed as a glycoprotein of about 150 KDa, although IgG can also be produced in a non-glycosylated form. The amino-terminal ("N") portion of each chain includes a variable region of about 100 to 110 or more amino acids primarily responsible for antigen recognition. The carboxy-terminal ("C") portion of each chain defines a constant region, with light chains having a single constant domain and heavy chains usually having three constant domains and a hinge region. Thus, the structure of the light chains of a naturally occurring IgG molecule is N-VL-CL-C and the structure of IgG heavy chains is N-VH-CH1-H-CH2-CH3-C (where H is the hinge region). The variable regions of an IgG molecule consists of the complementarity determining regions (CDRs), which contain the residues in contact with antigen and non-CDR segments, referred to as framework segments, which maintain the structure and determine the positioning of the CDR loops. Thus, the VL and VH domains have the structure N-FR1-CDR1-FR2-CDR2-FR3-CDR3-FR4-C.

As used herein, the term "heterologous" nucleic acid denotes DNA, RNA, etc. that is introduced into a host cell. The nucleic acid may be derived from any of a variety of sources including genomic DNA, mRNA, cDNA, synthetic DNA and fusions or combinations of these. The nucleic acid may include a polynucleotide from the same cell or cell type as the host or recipient cell or a polynucleotide from a different cell type, for example, from a mammal or plant, and may, optionally, include marker or selection genes, for example, antibiotic resistance genes, temperature resistance genes, etc.

The term "hinge region" is generally defined as stretching from Glu216 to Pro230 of human IgG1. Hinge regions of other IgG isotypes may be aligned with the IgG1 sequence by placing the first and last cysteine residues forming inter-heavy chain S—S bonds in the same positions.

As used herein, the term "humanized" has its usual meaning in the art. In general terms, humanization of a non-human antibody involves substituting the CDR sequences from non-human immunoglobulin $V_L$ and $V_H$ regions into human framework regions. Further, as used herein, "humanized" antibodies may comprise additional substitutions and mutations in the CDR and/or framework regions introduced to increase affinity or for other purposes.

For example, substitution of nonhuman framework residues in the human sequence can increase affinity. The resulting variable domains have non-human CDR sequences and framework sequences derived from human antibody framework sequence(s) or a human consensus sequence. A variety of different human framework regions may be used singly or in combination as a basis for a humanized antibody.

As used herein, the term "immunomodulatory agent" and variations thereof refer to an agent that modulates a host's immune system. In certain embodiments, an immunomodulatory agent is an immunosuppressant agent. In certain other embodiments, an immunomodulatory agent is an immunostimulatory agent Immunomodatory agents include, but are not limited to, small molecules, peptides, polypeptides, fusion proteins, antibodies, inorganic molecules, mimetic agents, and organic molecules.

As used herein, the term "immunospecifically binds," refers to the specific binding exhibited between an antibody and the epitope that it recognizes Such binding will typically exhibit a $K_D$ of at least about 0.1 mM, more usually at least about 1 µM, preferably at least about 0.1 µM or less, and most preferably, 0.01 µM or less. Preferably, the antibodies of the invention immunospecifically bind to proteins with high affinity (e.g., low $K_D$).

An antibody that immunospecifically binds to an antigen may bind to other peptides or polypeptides with lower affinity as determined by, e.g., immunoassays, BIAcore, or other assays known in the art. Preferably, molecules that specifically bind an antigen do not cross react with other proteins. Molecules that specifically bind an antigen can be identified, for example, by immunoassays, BIAcore, or other techniques known to those of skill in the art.

The term "Antibody Engineering Technology Art" as used herein refers to technology disclosed in U.S. Provisional Patent Application Nos. 60/781,564; 60/945,523; 61/015, 106; filed Dec. 19, 2007, and 61/019,051 filed Jan. 4, 2008; US 20040185045; US 20040197347; US 20040197866; US 20050037000; US 20050064514; US 20050215767; US 20060134709; US 20060177439; US 20070004909; US 20070036799; US 20070037216; US 20070077246; US 20070244303; US 20080044429; US 20080050371; 11/869, 410; 11/952,568; U.S. Pat. No. 7,112,439; WO 04/063351; WO 06/088494; WO 07/024249; WO 06/113665; WO 07/021841; WO 07/106707; or PCT/US07/86793

The term "monoclonal antibody" as used herein refers to an antibody obtained from a population of substantially homogeneous antibodies, i.e., the individual antibodies comprising the population are identical except for possible naturally occurring mutations that may be present in minor amounts, and the term "polyclonal antibody" as used herein refers to an antibody obtained from a population of heterogenous antibodies. Monoclonal antibodies are highly specific, being directed against a single epitope. In addition to their specificity, monoclonal antibodies are advantageous in that they may be synthesized without contamination by other antibodies. The term "monoclonal" indicates the character of the antibody as being obtained from a substantially homogeneous population of antibodies, and is not to be construed as requiring production of the antibody by any particular method.

As used herein, the terms "nucleic acids" and "nucleotide sequences" include DNA molecules (e.g., cDNA or genomic DNA), RNA molecules (e.g., mRNA), combinations of DNA and RNA molecules or hybrid DNA/RNA molecules, and analogs of DNA or RNA molecules. Such analogs can be generated using, for example, nucleotide analogs, which include, but are not limited to, inosine or tritylated bases. Such analogs can also comprise DNA or RNA molecules comprising modified backbones that lend beneficial attributes to the molecules such as, for example, nuclease resistance or an increased ability to cross cellular membranes. The nucleic acids or nucleotide sequences can be single-stranded, double-stranded, may contain both single-stranded and double-stranded portions, and may contain triple-stranded portions, but preferably is double-stranded DNA.

"Substantial sequence identity," as used herein, refers to two or more sequences or subsequences (e.g., domains) that have at least about 80% amino acid residue identity, preferably at least about 90%, or at least about 95% identity when compared and aligned for maximum correspondence. Sequence identity between two similar sequences (e.g., antibody variable regions) can be measured by algorithms such as that of Smith & Waterman, 1981, Adv. Appl. Math. 2:482 [local homology algorithm], Needleman & Wunsch, 1970, J. Mol. Biol. 48:443 [homology alignment algorithm], Pearson & Lipman, 1988, Proc. Natl. Acad. Sci. (U.S.A.) 85:2444 [search for similarity method], or Altschul et al., 1990, J. Mol. Biol. 215:403-10 [BLAST algorithm]. When using any of the aforementioned algorithms, the default parameters (for Window length, gap penalty, etc.) are used. An amino acid sequence is said to be "substantially similar to" a second sequence when the degree of sequence identity is at least about 70% identical, preferably at least about 80%, or at least about 90%, or even at least about 95%, identical. A nucleic acid sequence is said to be "substantially similar to" a second sequence when either: (1) the degree of sequence identity is at least about 70% identical, preferably at least about 80%, or at least about 90%, or even at least about 95%, identical, or the nucleic acid sequence encodes a polypeptide that is at least about 70% identical, preferably at least about 80%, or at least about 90%, or even at least about 95%, identical to the polypeptide encoded by the second sequence. Sequences that are substantially identical are also substantially similar.

When referring to antibodies, the assignment of amino acids to each domain is in accordance with Kabat, *Sequences Of Proteins Of Immunological Interest* (National Institutes of Health, Bethesda, Md., 1987 and 1991), which is expressly incorporated herein by reference. Throughout the present specification, the numbering of the residues in an IgG heavy chain is that of the EU index as in Kabat, and refers to the numbering of the human IgG1 EU antibody.

B. Antibodies

The present invention particularly encompasses chimeric antibodies and polypeptides that specifically bind to HER2/neu, preferably human HER2/neu. The antibodies have reduced glycosylation as compared to known 4D5 antibodies such as murine 4D5 and trastuzumab, due to the removal of a glycosylation site in the variable region of the light chain. In particular, the antibodies lack a glycosylation site in the variable region of the light chain, which in the native murine 4D5 comprises an N-R-S sequence at positions 65, 66 and 67. Preferably the antibodies have enhanced binding affinity for HER2/neu, and more preferably the antibodies have enhanced effector function, both as compared to a native 4D5 antibody.

The antibodies comprise a chimeric 4D5 immunoglobulin light chain lacking an N-linked glycosylation site at positions 65, 66 and 67 of the light chain variable region. In a particular embodiment, the antibodies comprise a modification, preferably a substitution, at position 65 of the variable region of the light chain ($V_L$). In a preferred embodiment, the antibodies comprise a light chain encoded by the nucleic acid sequence of SEQ ID NO: 1, or comprise the amino acid sequence of SEQ ID NO: 2. The nucleic acid and amino acid sequences of a preferred light chain of the present invention are presented below:

```
Chimeric light chain nucleic acid sequence (SEQ ID NO: 1):
gacatcgtga tgacccagtc ccacaagttc atgtccacct ctgtgggcga tagggtcagc    60
atcacctgca aggccagcca ggatgtgaat actgctgtag cctggtatca gcagaaacca   120
ggacattctc ccaaactgct gatttactcc gcatccttcc ggtacactgg agtccctgat   180
cgcttcactg gcagcagatc tgggacagat ttcactttca ccatcagcag tgtgcaggct   240
gaagacctgg cagtttatta ctgtcagcaa cattatacta cacctcccac cttcggaggg   300
ggtaccaagg tggagatcaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gttag                  645

Chimeric light chain amino acid sequence (SEQ ID NO: 2):
DIVMTQSHKF MSTSVGDRVS ITCKASQDVN TAVAWYQQKP GHSPKLLIYS ASFRYTGVPD    60

RFTGSRSGTD FTFTISSVQA EDLAVYYCQQ HYTTPPTFGG GTKVEIKRTV AAPSVFIFPP   120

SDEQLKSGTA SVVCLLNNFY PREAKVQWKV DNALQSGNSQ ESVTEQDSKD STYSLSSTLT   180

LSKADYEKHK VYACEVTHQG LSSPVTKSFN RGEC                               214
```

These antibodies having a modification at positions 65 of the $V_L$ region lack an N-linked glycosylation site found in the native murine 4D5 antibody, as can be seen in FIG. 1, which depicts an exemplary comparison between the $V_L$ region amino acid sequences of a chimeric 4D5 antibody having an N65S modification (SEQ ID NO: 4), and the native murine (SEQ ID NO: 3) and humanized (SEQ ID NO: 5) 4D5 antibodies. In another preferred embodiment, the antibodies comprise a N65S modification in the $V_L$ region, and preferably have a $V_L$ region amino acid sequence of SEQ ID NO: 4. These sequences are presented below:

```
Native murine V_L region amino acid sequence (SEQ ID NO: 3):
DIVMTQSHKF MSTSVGDRVS ITCKASQDVN TAVAWYQQKP GHSPKLLIYS ASFRYTGVPD    60

RFTGNRSGTD FTFTISSVQA EDLAVYYCQQ HYTTPPTFGG GTKLEIKRA               109

Chimeric V_L region amino acid sequence (SEQ ID NO: 4):
DIVMTQSHKF MSTSVGDRVS ITCKASQDVN TAVAWYQQKP GHSPKLLIYS ASFRYTGVPD    60

RFTGSRSGTD FTFTISSVQA EDLAVYYCQQ HYTTPPTFGG GTKVEIKRT               109

Humanized V_L region amino acid sequence (SEQ ID NO: 5):
DIQMTQSPSS LSASVGDRVT ITCRASQDVN TAVAWYQQKP GKAPKLLIYS ASFLESGVPS    60

RFSGSRSGTD FTLTISSLQP EDFATYYCQQ HYTTPPTFGQ GTKVEIKRT               109
```

In one embodiment, the heavy chain has a murine 4D5 wild-type Fc region, preferably encoded by the nucleic acid sequence of SEQ ID NO: 6, or having the amino acid sequence of SEQ ID NO: 7. These sequences are presented below:

```
Heavy chain having wild-type Fc region nucleic acid sequence (SEQ ID
NO: 6):
caggttcagc tgcagcagtc tggccctgag ctggtgaagc caggggcctc actcaagttg    60
tcctgtacag cttctggctt caacatcaaa gacacctata tccactgggt gaaacagagg   120
cctgaacagg gcctggaatg gattggaagg atttatccta ccaatggcta tactagatat   180
gacccaaagt tccaggacaa ggccactatc acagcagaca tcctccaa cacagcctac    240 ctgcaagtca gccgcctgac atctgaggac actgccgtct attactgctc ccggtgggga   300
ggggacggct tctatgctat ggactactgg ggtcagggag cctccgtgac cgtgagctcc   360
```

-continued

```
gcctccacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagag agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag gcagccccg agaaccacag gtgtacaccc tgcccccatc ccgggatgag   1080
ctgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctac agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa tga                                1353
```

Heavy chain having wild-type Fc region amino acid sequence (SEQ ID NO: 7):

```
QVQLQQSGPE LVKPGASLKL SCTASGFNIK DTYIHWVKQR PEQGLEWIGR IYPTNGYTRY     60

DPKFQDKATI TADTSSNTAY LQVSRLTSED TAVYYCSRWG GDGFYAMDYW GQGASVTVSS    120

ASTKGPSVFP LAPSSKSTSG GTAALGCLVK DYFPEPVTVS WNSGALTSGV HTFPAVLQSS    180

GLYSLSSVVT VPSSSLGTQT YICNVNHKPS NTKVDKRVEP KSCDKTHTCP PCPAPELLGG    240

PSVFLFPPKP KDTLMISRTP EVTCVVVDVS HEDPEVKFNW YVDGVEVHNA KTKPREEQYN    300

STYRVVSVLT VLHQDWLNGK EYKCKVSNKA LPAPIEKTIS KAKGQPREPQ VYTLPPSRDE    360

LTKNQVSLTC LVKGFYPSDI AVEWESNGQP ENNYKTTPPV LDSDGSFFLY SKLTVDKSRW    420

QQGNVFSCSV MHEALHNHYT QKSLSLSPGK                                     450
```

In other embodiments, the heavy chain is a variant of a murine 4D5 antibody heavy chain, preferably comprising a variant Fc region, and more preferably comprising a variant Fc region such as FcMT1, FcMT2, or FcMT3. These sequences are presented below:

Heavy chain having FcMT1 variant Fc region nucleic acid sequence (SEQ ID NO: 8):

```
caggttcagc tgcagcagtc tggccctgag ctggtgaagc caggggcctc actcaagttg     60
tcctgtacag cttctggctt caacatcaaa gacacctata tccactgggt gaaacagagg    120
cctgaacagg gcctggaatg gattggaagg atttatccta ccaatggcta tactagatat    180
gacccaaagt tccaggacaa ggccactatc acagcagaca catcctccaa cacagcctac    240
ctgcaagtca gccgcctgac atctgaggac actgccgtct attactgctc ccggtgggga    300
ggggacggct ctatgctat ggactactgg ggtcagggag cctccgtgac cgtgagctcc    360
gcctccacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
```

-continued

```
ggactctact ccctcagcag cgtggtgacc gtgccctcca gcagcttggg cacccagacc      600
tacatctgca acgtgaatca caagcccagc aacaccaagg tggacaagag agttgagccc      660
aaatcttgtg acaaaactca cacatgccca ccgtgcccag cacctgaact cctggggga      720 ccgtcagtct tcctcttacc cccaaaaccc aaggacaccc tcatgatctc ccggaccct      780 gaggtcacat gcgtggtggt ggacgtgagc cacgaagacc ctgaggtcaa gttcaactgg      840
tacgtggacg gcgtggaggt gcataatgcc aagacaaagc cgccggagga gcagtacaac      900
agcacgctcc gtgtggtcag catcctcacc gtcctgcacc aggactggct gaatggcaag      960
gagtacaagt gcaaggtctc caacaaagcc ctcccagccc ccatcgagaa aaccatctcc     1020
aaagccaaag gcagccccg agaaccacag gtgtacaccc tgcccccatc ccgggatgag     1080
ctgaccaaga accaggtcag cctgacctgc ctggtcaaag gcttctatcc cagcgacatc     1140
gccgtggagt gggagagcaa tgggcagccg gagaacaact acaagaccac gcctctcgtg     1200
ctggactccg acggctcctt cttcctctac agcaagctca ccgtggacaa gagcaggtgg     1260
cagcagggga acgtcttctc atgctccgtg atgcatgagg ctctgcacaa ccactacacg     1320
cagaagagcc tctccctgtc tccgggtaaa tga                                 1353
```

Heavy chain having FcMT1 variant Fc region amino acid sequence (SEQ ID NO: 9):

```
QVQLQQSGPE LVKPGASLKL SCTASGFNIK DTYIHWVKQR PEQGLEWIGR IYPTNGYTRY      60

DPKFQDKATI TADTSSNTAY LQVSRLTSED TAVYYCSRWG GDGFYAMDYW GQGASVTVSS     120

ASTKGPSVFP LAPSSKSTSG GTAALGCLVK DYFPEPVTVS WNSGALTSGV HTFPAVLQSS     180

GLYSLSSVVT VPSSSLGTQT YICNVNHKPS NTKVDKRVEP KSCDKTHTCP PCPAPELLGG     240

PSVFLLPPKP KDTLMISRTP EVTCVVVDVS HEDPEVKFNW YVDGVEVHNA KTKPPEEQYN     300

STLRVVSILT VLHQDWLNGK EYKCKVSNKA LPAPIEKTIS KAKGQPREPQ VYTLPPSRDE     360

LTKNQVSLTC LVKGFYPSDI AVEWESNGQP ENNYKTTPLV LDSDGSFFLY SKLTVDKSRW     420

QQGNVFSCSV MHEALHNHYT QKSLSLSPGK                                     450
```

Heavy chain having FcMT2 variant Fc region nucleic acid sequence (SEQ ID NO: 10):

```
caggttcagc tgcagcagtc tggccctgag ctggtgaagc caggggcctc actcaagttg       60
tcctgtacag cttctggctt caacatcaaa gacacctata tccactgggt gaaacagagg      120
cctgaacagg gcctggaatg gattggaagg atttatccta ccaatggcta ctactagatat     180 gacccaaagt tccaggacaa ggccactatc acagcagaca catcctccaa cacagcctac      240
ctgcaagtca gccgcctgac atctgaggac actgccgtct attactgctc ccggtgggga     300
ggggacggct tctatgctat ggactactgg ggtcaggag cctccgtgac cgtgagctcc       360
gcctccacca agggcccatc ggtcttcccc ctggcaccct cctccaagag cacctctggg      420
ggcacagcgg ccctgggctg cctggtcaag gactacttcc ccgaaccggt gacggtgtcg      480
tggaactcag gcgccctgac cagcggcgtg cacaccttcc cggctgtcct acagtcctca      540
ggactctact ccctcagcag cgtggtgacc gtgccctcca gcagcttggg cacccagacc      600
tacatctgca acgtgaatca caagcccagc aacaccaagg tggacaagag agttgagccc      660
aaatcttgtg acaaaactca cacatgccca ccgtgcccag cacctgaact cgtggggga      720 ccgtcagtct tcctcttacc cccaaaaccc aaggacaccc tcatgatctc ccggaccct      780 gaggtcacat gcgtggtggt ggacgtgagc cacgaagacc ctgaggtcaa gttcaactgg      840
tacgtggacg gcgtggaggt gcataatgcc aagacaaagc cgccggagga gcagtacaac      900
agcacgctcc gtgtggtcag cgtcctcacc gtcctgcacc aggactggct gaatggcaag      960
gagtacaagt gcaaggtctc caacaaagcc ctcccagccc ccatcgagaa aaccatctcc     1020
```

-continued

```
aaagccaaag ggcagccccg agaaccacag gtgtacaccc tgcccccatc ccgggatgag    1080
ctgaccaaga accaggtcag cctgacctgc ctggtcaaag gcttctatcc cagcgacatc    1140
gccgtggagt gggagagcaa tgggcagccg gagaacaact acaagaccac gcctctcgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa tga                                 1353
```

Heavy chain having FcMT2 variant Fc region amino acid sequence (SEQ ID NO: 11):

```
QVQLQQSGPE LVKPGASLKL SCTASGFNIK DTYIHWVKQR PEQGLEWIGR IYPTNGYTRY     60

DPKFQDKATI TADTSSNTAY LQVSRLTSED TAVYYCSRWG GDGFYAMDYW GQGASVTVSS    120

ASTKGPSVFP LAPSSKSTSG GTAALGCLVK DYFPEPVTVS WNSGALTSGV HTFPAVLQSS    180

GLYSLSSVVT VPSSSLGTQT YICNVNHKPS NTKVDKRVEP KSCDKTHTCP PCPAPELVGG    240

PSVFLLPPKP KDTLMISRTP EVTCVVVDVS HEDPEVKFNW YVDGVEVHNA KTKPPEEQYN    300

STLRVVSVLT VLHQDWLNGK EYKCKVSNKA LPAPIEKTIS KAKGQPREPQ VYTLPPSRDE    360

LTKNQVSLTC LVKGFYPSDI AVEWESNGQP ENNYKTTPLV LDSDGSFFLY SKLTVDKSRW    420

QQGNVFSCSV MHEALHNHYT QKSLSLSPGK                                     450
```

Heavy chain having FcMT3 variant Fc region nucleic acid sequence (SEQ ID NO: 12):

```
caggttcagc tgcagcagtc tggccctgag ctggtgaagc caggggcctc actcaagttg     60
tcctgtacag cttctggctt caacatcaaa gacacctata tccactgggt gaaacagagg    120
cctgaacagg cctggaatg gattggaagg atttatccta ccaatggcta ctagatat      180 gacccaaagt tccaggacaa ggccactatc acagcagaca catcctccaa cacagcctac    240
ctgcaagtca gccgcctgac atctgaggac actgccgtct attactgctc ccggtgggga    300
ggggacggct tctatgctat ggactactgg ggtcagggag cctccgtgac cgtgagctcc    360
gcctccacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagag agttgagccc    660
aaatcttgtg acaaaactca cacatgccca ccgtgcccag cacctgaact cctgggggga    720
ccgtcagtct tcctcttacc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcggagga gcagtacaac    900 agcacgctcc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag ggcagccccg agaaccacag gtgtacaccc tgcccccatc ccgggatgag   1080
ctgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctac agcaagctca ccgtggacaa gagcaggtgg   1260
```

-continued

```
cagcagggga acgtcttctc atgctccgtg atgcatgagg ctctgcacaa ccactacacg   1320
cagaagagcc tctccctgtc tccgggtaaa tga                                1353
```

Heavy chain having FcMT3 variant Fc region amino acid sequence (SEQ ID
NO: 13):

```
QVQLQQSGPE LVKPGASLKL SCTASGFNIK DTYIHWVKQR PEQGLEWIGR IYPTNGYTRY    60

DPKFQDKATI TADTSSNTAY LQVSRLTSED TAVYYCSRWG GDGFYAMDYW GQGASVTVSS   120

ASTKGPSVFP LAPSSKSTSG GTAALGCLVK DYFPEPVTVS WNSGALTSGV HTFPAVLQSS   180

GLYSLSSVVT VPSSSLGTQT YICNVNHKPS NTKVDKRVEP KSCDKTHTCP PCPAPELLGG   240

PSVFLLPPKP KDTLMISRTP EVTCVVVDVS HEDPEVKFNW YVDGVEVHNA KTKPPEEQYN   300

STLRVVSVLT VLHQDWLNGK EYKCKVSNKA LPAPIEKTIS KAKGQPREPQ VYTLPPSRDE   360

LTKNQVSLTC LVKGFYPSDI AVEWESNGQP ENNYKTTPPV LDSDGSFFLY SKLTVDKSRW   420

QQGNVFSCSV MHEALHNHYT QKSLSLSPGK                                    450
```

In one embodiment, a variant 4D5 heavy chain has a modification in the Fc region, and is encoded by the nucleic acid sequence of SEQ ID NO: 8 or comprises the amino acid sequence of SEQ ID NO: 9, or is encoded by the nucleic acid sequence of SEQ ID NO: 10 or comprises the amino acid sequence of SEQ ID NO: 11, or is encoded by the nucleic acid sequence of SEQ ID NO: 12 or comprises the amino acid sequence of SEQ ID NO: 13. Preferably, the antibodies comprise a heavy chain encoded by a nucleic acid sequence selected from the group consisting of SEQ ID NO: 6, SEQ ID NO: 8, SEQ ID NO: 10, and SEQ ID NO: 12, or comprising an amino acid sequence selected from the group consisting of SEQ ID NO: 7, SEQ ID NO: 9, SEQ ID NO: 11, and SEQ ID NO: 13.

In one embodiment, an anti-HER2/neu antibody comprises an immunoglobulin light chain having a N65S modification in the $V_L$ region, and an immunoglobulin heavy chain having a modified Fc region. Preferably, an anti-HER2/neu antibody comprises a light chain having the amino acid sequence of SEQ ID NO: 2, and a heavy chain having an amino acid sequence selected from the group consisting of SEQ ID NO: 7, SEQ ID NO: 9, SEQ ID NO: 11, and SEQ ID NO: 13. In some embodiments, a polypeptide of the invention further comprises a light chain constant domain fused to a light chain variable domain, which in some embodiments comprises at least SEQ ID NO: 4. In other embodiments, the antibody is modified, a fragment, or a modified fragment.

Chimeric 4D5 antibodies were constructed in accordance with the various embodiments of the invention, to enhance binding to activating low-affinity Fc receptors, and to not alter, or only minimally increase, binding to the low-affinity inhibitor receptor CD32B (FcγRII-B). The antibodies include the following wild-type and Fc-optimized antibodies:

ch4D5-wild-type Fc, which has a light chain having an amino acid sequence of SEQ ID NO: 2, and a heavy chain having an amino acid sequence of SEQ ID NO: 7. ch4D5-wild-type Fc has an N65S substitution on the light chain, which results in a de-glycosylated light chain ch4D5-FcMT1, which has a light chain having an amino acid sequence of SEQ ID NO: 2, and a heavy chain having an amino acid sequence of SEQ ID NO: 9. ch4D5-FcMT1 has an N65S substitution on the light chain, which results in a de-glycosylated light chain, and F243L, R292P, Y300L, V305I, and P396L substitutions on the heavy chain (all numbered according to Kabat). ch4D5-FcMT1 exhibits a 10-fold increase in binding to human CD16A (FcγRIII-A), and binding to CD16-158$^{Phe}$ is enhanced in a proportionally greater fashion than binding to CD16-158$^{Val}$.

ch4D5-FcMT2, which has a light chain having an amino acid sequence of SEQ ID NO: 2, and a heavy chain having an amino acid sequence of SEQ ID NO: 11. ch4D5-FcMT2 has an N65S substitution on the light chain, which results in a de-glycosylated light chain, and L235V, F243L, R292P, Y300L, and P396L substitutions on the heavy chain (all numbered according to Kabat). This antibody is a further refinement of the ch4D5-FcMT1 antibody, and has similar CD16A binding properties, but also has a more favorable reduction in binding to CD32B (FcγRII-B).

ch4D5-FcMT3, which has a light chain having an amino acid sequence of SEQ ID NO: 2, and a heavy chain having an amino acid sequence of SEQ ID NO: 13. ch4D5-FcMT3 has an N65S substitution on the light chain, which results in a de-glycosylated light chain, and F243L, R292P, and Y300L substitutions on the heavy chain (all numbered according to Kabat). This antibody is a further refinement of the ch4D5-FcMT1 antibody, and has similar CD16A binding properties, but also has a more favorable reduction in binding to CD32B (FcγRII-B).

ch4D5-Ag ch4D5-N297Q, which has a light chain having an amino acid sequence of SEQ ID NO: 2, and a heavy chain having an N297Q substitution (numbered according to Kabat).

A comparison of the heavy chain sequences of the ch4D5-wild-type Fc and the Fc-optimized variants ch4D5-FcMT1, ch4D5-FcMT2, and ch4D5-FcMT3 is shown in FIG. 2. The CDRs are indicated with black bars shown underneath the pertinent residues.

Polypeptides (especially antibodies) contemplated by the present invention may comprise all or part of any amino acid sequence of the present invention. For example, in one embodiment a polypeptide comprises a murine 4D5 immunoglobulin light chain having an N65S substitution, and in another embodiment a polypeptide comprises a murine 4D5 immunoglobulin heavy chain variant. In another embodiment, a polypeptide comprises an immunoglobulin light chain variable domain having the amino acid sequence of SEQ ID NO: 4, or an immunoglobulin light chain having the amino acid sequence of SEQ ID NO: 2. In another embodiment, the polypeptide comprises a variant Fc domain, or an immunoglobulin heavy chain having the amino acid sequence of SEQ ID NO: 7, SEQ ID NO: 9, SEQ ID NO: 11, or SEQ ID NO: 13, or a 4D5 immunoglobulin heavy chain comprising F243L, R292P, and Y300L substitutions.

Polypeptides (especially antibodies) contemplated by the present invention may be in a complex with one another or with other non-immunoglobulin polypeptides (e.g., enzymes, hormones, structural proteins, etc.). For example, an embodiment may provide a polypeptide complex comprising two polypeptides, wherein one of said polypeptides comprises a heavy chain, and the other polypeptide comprises a variant light chain, or wherein both polypeptides comprise the same sequences. Complexing can be mediated by any suitable technique, including by dimerization/multimerization at a dimerization/multimerization domain such as those described herein or covalent interactions (such as through a disulfide linkage) (which in some contexts is part of a dimerization domain, for example a dimerization domain may contain a leucine zipper sequence and a cysteine). In another embodiment, a composition may comprise polypeptides and/or polynucleotides of the invention, for example a composition may comprise a plurality of any of the polypeptides described herein. A composition comprising a polynucleotide or polypeptide may be in the form of a kit or an article of manufacture (optionally packaged with instructions, buffers, etc.).

It is also contemplated that polypeptide variants (and in particular antibody variants) can be prepared. The polypeptide variants may possess sequence modifications (e.g., substitutions, deletions and/or additions) at desired positions within their amino acid sequences relative to the native amino acid sequence. Those skilled in the art will appreciate that amino acid changes may alter post-translational processes of the antibody or polypeptide, such as changing the number or position of glycosylation sites or altering the membrane anchoring characteristics. In a preferred embodiment, the antibody and polypeptide variants are Fc region variants.

Variants may have the same or altered activity as compared to a native antibody or polypeptide. For example, it may be desirable that the variant have the same activity, but be modified in a manner so that it is more stable or has a longer half-life in vivo, for example by conjugating the antibody with albumin or a salvage receptor binding epitope, as described, e.g., in U.S. Pat. No. 5,739,277. Or, for example, it may be desirable that an antibody have an increased binding affinity to antigen, but the same effector function as a native antibody, or it may be desirable that an antibody have the same binding affinity to antigen, but a decreased effector function. Activity may be tested by, e.g., using in vitro assays such as ELISA assays, surface plasmon resonance assays, radiolabeled protein binding assays (RIA), or immunoprecipitation assays.

Substantial modifications in function or immunological identity may be accomplished by selecting modifications that differ significantly in their effect on maintaining (a) the structure of the polypeptide backbone in the area of the modification, for example, as a sheet or helical conformation, (b) the charge or hydrophobicity of the molecule at the target site, or (c) the bulk of the side chain Scanning amino acid analysis can also be employed to identify one or more amino acids along a contiguous sequence, for example as described by Cunningham and Wells (1989) Science 244: 1081-1085. Among the preferred scanning amino acids are relatively small, neutral amino acids, such as alanine, glycine, serine, and cysteine. Alanine is typically a preferred scanning amino acid among this group because it is the most common amino acid, is frequently found in both buried and exposed positions, and because it eliminates the side-chain beyond the beta-carbon and is less likely to alter the main-chain conformation of the variant. If alanine substitution does not yield adequate amounts of variant, an isoteric amino acid can be used. Further, any cysteine residue not involved in maintaining the proper conformation of the antibody or polypeptide may be substituted, generally with serine, to improve the oxidative stability of the molecule and prevent aberrant crosslinking. However, in certain circumstances, particularly where the antibody is an antibody fragment such as an Fv fragment, cysteine bond(s) may be added to the antibody or polypeptide to improve its stability.

B1. Fc Domain Variants

The polypeptides of the present invention may have variant Fc domains. Modification of the Fc domain normally leads to an altered phenotype, for example altered serum half-life, altered stability, altered susceptibility to cellular enzymes or altered effector function. It may be desirable to modify the antibody of the invention with respect to effector function, so as to enhance the effectiveness of the antibody in treating cancer, for example Reduction or elimination of effector function is desirable in certain cases, for example in the case of antibodies whose mechanism of action involves blocking or antagonism, but not killing of the cells bearing a target antigen. Increased effector function is generally desirable when directed to undesirable cells, such as tumor and foreign cells, where the FcγRs are expressed at low levels, for example, tumor specific B cells with low levels of FcγRIIB (e.g., non-Hodgkins lymphoma, CLL, and Burkitt's lymphoma). In said embodiments, molecules of the invention with conferred or altered effector function activity are useful for the treatment and/or prevention of a disease, disorder or infection where an enhanced efficacy of effector function activity is desired.

In certain embodiments, the molecules of the invention comprise one or more modifications to the amino acids of the Fc domain, which reduce the affinity and avidity of the Fc region and, thus, the molecule of the invention, for one or more FcγR receptors. In other embodiments, the molecules of the invention comprise one or more modifications to the amino acids of the Fc region, which increase the affinity and avidity of the Fc region and, thus, the molecule of the invention, for one or more FcγR receptors. In other embodiments, the molecules comprise a variant Fc domain wherein said variant confers or mediates increased ADCC activity and/or an increased binding to FcγRIIA, relative to a molecule comprising no Fc domain or comprising a wild-type Fc domain. In alternate embodiments, the molecules comprise a variant Fc domain wherein said variant confers or mediates decreased ADCC activity (or other effector function) and/or an increased binding to FcγRIIB, relative to a molecule comprising no Fc domain or comprising a wild-type Fc domain.

In some embodiments, the invention encompasses molecules comprising a variant Fc region, which variant Fc region does not show a detectable binding to any FcγR, relative to a comparable molecule comprising the wild-type Fc region. In other embodiments, the invention encompasses molecules comprising a variant Fc region, which variant Fc region only binds a single FcγR, preferably one of FcγRIIA, FcγRIIB, or FcγRIIIA.

The polypeptides of the present invention may comprise altered affinities for an activating and/or inhibitory Fcγ receptor. In one embodiment, the antibody or polypeptide comprises a variant Fc region that has increased affinity for FcγRIIB and decreased affinity for FcγRIIIA and/or FcγRIIA, relative to a comparable molecule with a wild-type Fc region. In another embodiment, the polypeptides of the present invention comprise a variant Fc region, which has decreased affinity for FcγRIIB and increased affinity for FcγRIIIA and/or FcγRIIA, relative to a comparable molecule with a wild-type Fc region. In yet another embodiment, the polypeptides of the present invention comprise a variant Fc region that has decreased affinity for FcγRIIB and decreased affinity for FcγRIIIA and/or FcγRIIA, relative to a comparable molecule with a wild-type Fc region. In still another embodiment, the polypeptides of the present invention comprise a variant Fc region, which has unchanged affinity for FcγRIIB and decreased (or increased) affinity for FcγRIIIA and/or FcγRIIA, relative to a comparable molecule with a wild-type Fc region.

In certain embodiments, the invention encompasses immunoglobulins comprising a variant Fc region with an altered affinity for FcγRIIIA and/or FcγRIIA such that the immunoglobulin has an enhanced effector function, e.g., antibody dependent cell mediated cytotoxicity. Non-limiting examples of effector cell functions include antibody-dependent cell mediated cytotoxicity (ADCC), antibody-dependent phagocytosis, phagocytosis, opsonization, opsonophagocytosis, cell binding, rosetting, C1q binding, and complement dependent cell mediated cytotoxicity.

In a preferred embodiment, the alteration in affinity or effector function is at least 2-fold, preferably at least 4-fold, at least 5-fold, at least 6-fold, at least 7-fold, at least 8-fold, at least 9-fold, at least 10-fold, at least 50-fold, or at least 100-fold, relative to a comparable molecule comprising a wild-type Fc region. In other embodiments of the invention, the variant Fc region immunospecifically binds one or more FcRs with at least 65%, preferably at least 70%, 75%, 80%, 85%, 90%, 95%, 100%, 125%, 150%, 175%, 200%, 225%, or 250% greater affinity relative to a molecule comprising a wild-type Fc region. Such measurements can be in vivo or in vitro assays, and in a preferred embodiment are in vitro assays such as ELISA or surface plasmon resonance assays.

In different embodiments, the molecules comprise a variant Fc domain wherein said variant agonizes at least one activity of an FcγR receptor, or antagonizes at least one activity of an FcγR receptor. In a preferred embodiment, the molecules comprise a variant that agonizes (or antagonizes) one or more activities of FcγRIIB, for example, B cell receptor-mediated signaling, activation of B cells, B cell proliferation, antibody production, intracellular calcium influx of B cells, cell cycle progression, FcγRIIB-mediated inhibition of FcεRI signaling, phosphorylation of FcγRIIB, SHIP recruitment, SHIP phosphorylation and association with Shc, or activity of one or more downstream molecules (e.g., MAP kinase, JNK, p38, or Akt) in the FcγRIIB signal transduction pathway. In another embodiment, the molecules comprise a variant that agonizes (or antagonizes) one or more activities of FcεRI, for example, mast cell activation, calcium mobilization, degranulation, cytokine production, or serotonin release.

In certain embodiments, the molecules comprise an Fc domain comprising domains or regions from two or more IgG isotypes (e.g., IgG1, IgG2, IgG3 and IgG4). The various IgG isotypes exhibit differing physical and functional properties including serum half-life, complement fixation, FcγR binding affinities and effector function activities (e.g. ADCC, CDC, etc.) due to differences in the amino acid sequences of their hinge and/or Fc domains, for example as described in Flesch and Neppert (1999) J. Clin. Lab. Anal. 14:141-156; Chappel et al. (1993) J. Biol. Chem. 33:25124-25131; Chappel et al. (1991) Proc. Natl. Acad. Sci. (U.S.A.) 88:9036-9040; Brüggemann et al. (1987) J. Exp. Med 166: 1351-1361. This type of variant Fc domain may be used alone, or in combination with an amino acid modification, to affect Fc-mediated effector function and/or binding activity. In combination, the amino acid modification and IgG hinge/Fc region may display similar functionality (e.g., increased affinity for FcγRIIA) and may act additively or, more preferably, synergistically to modify the effector functionality in the molecule of the invention, relative to a molecule of the invention comprising a wild-type Fc region. In other embodiments, the amino acid modification and IgG Fc region may display opposite functionality (e.g., increased and decreased affinity for FcγRIIA, respectively) and may act to selectively temper or reduce a specific functionality in the molecule of the invention, relative to a molecule of the invention not comprising an Fc region or comprising a wild-type Fc region of the same isotype.

In a preferred specific embodiment, the molecules comprise a variant Fc region, wherein said variant Fc region comprises at least one amino acid modification relative to a wild-type Fc region, such that said molecule has an altered affinity for an FcR, provided that said variant Fc region does not have a substitution at positions that make a direct contact with FcγR based on crystallographic and structural analysis of Fc-FcR interactions such as those disclosed by Sondermann et al. (2000) Nature 406:267-273. Examples of positions within the Fc region that make a direct contact with FcγR are amino acid residues 234-239 (hinge region), amino acid residues 265-269 (B/C loop), amino acid residues 297-299 (C'/E loop), and amino acid residues 327-332 (F/G loop). In some embodiments, the molecules of the invention comprise variant Fc regions comprise modification of at least one residue that does not make a direct contact with an FcγR based on structural and crystallographic analysis, e.g., is not within the Fc-FcγR binding site.

Variant Fc domains are well known in the art, and any known Fc variant may be used in the present invention to confer or modify the effector function exhibited by a molecule of the invention comprising an Fc domain (or portion thereof) as functionally assayed, e.g., in an NK dependent or macrophage dependent assay. For example, Fc domain variants identified as altering effector function are disclosed in the Antibody Engineering Technology Art, and any suitable variant disclosed therein may be used in the present molecules.

In certain embodiments, the molecules comprise a variant Fc region, having one or more amino acid modifications in one or more regions, which modification(s) alter (relative to a wild-type Fc region) the Ratio of Affinities of the variant Fc region to an activating FcγR (such as FcγRIIA or FcγRIIIA) relative to an inhibiting FcγR (such as FcγRIIB):

$$\text{Ratio of Affinities} = \frac{\text{Wild-Type to Variant Change in Affinity to } Fc\gamma R_{Activating}}{\text{Wild-Type to Variant Change in Affinity to } Fc\gamma R_{Inhibiting}}$$

Where an Fc variant has a Ratio of Affinities greater than 1, the methods of the invention have particular use in providing a therapeutic or prophylactic treatment of a disease, disorder, or infection, or the amelioration of a symptom thereof, where an enhanced efficacy of effector cell function (e.g., ADCC) mediated by FcγR is desired, e.g., cancer or infectious disease. Where an Fc variant has a Ratio of Affinities less than 1, the methods of the invention have particular use in providing a therapeutic or prophylactic treatment of a disease or disorder, or the amelioration of a symptom thereof, where a decreased efficacy of effector cell function mediated by FcγR is desired, e.g., autoimmune or inflammatory disorders. Table 2 lists exemplary single, double, triple, quadruple and quintuple mutations by whether their Ratio of Affinities is greater than or less than 1. Specific binding data for various mutations is listed in Table 3, and more information concerning these mutations may be found in the Antibody Engineering Technology Art.

TABLE 2

Exemplary Single and Multiple Mutations Listed by Ratio of Affinities

| Ratio | Single | Double | Triple | Quadruple | Quintuple |
|---|---|---|---|---|---|
| >1 | F243L D270E R292G R292P | F243L & R292P F243L & Y300L F243L & P396L D270E & P396L R292P & Y300L R292P & V305I R292P & P396L Y300L & P396L P396L & Q419H | F243L, P247L & N421K F243L, R292P & Y300L F243L, R292P & V305I F243L, R292P & P396L F243L, Y300L & P396L P247L, D270E & N421K R255L, D270E & P396L D270E, G316D & R416G D270E, K392T & P396L D270E, P396L & Q419H V284M, R292L & K370N R292P, Y300L & P396L | L234F, F243L, R292P & Y300L L235I, F243L, R292P & Y300L L235Q, F243L, R292P & Y300L F243L, P247L, D270E & N421K F243L, R255L, D270E & P396L F243L, D270E, G316D & R416G F243L, D270E, K392T & P396L F243L, D270E, P396L & Q419H F243L, R292P, Y300L, & P396L F243L, R292P, V305I & P396L P247L, D270E, Y300L & N421K R255L, D270E, R292G & P396L R255L, D270E, Y300L & P396L D270E, G316D, P396L & R416G | L235V, F243L, R292P, Y300L & P396L L235I, F243L, R292P, Y300L & P396L L235P, F243L, R292P, Y300L & P396L F243L, R292P, V305I, Y300L & P396L |
| <1 | Y300L P396L | F243L & P396L P247L & N421K R255L & P396L R292P & V305I K392T & P396L P396L & Q419H | F243L, R292P & V305I | | |

TABLE 3

Detailed Binding Information for Exemplary Fc Variants

| | CD16A | CD16A | | Ratio of Affinities CD16A/CD32B | |
|---|---|---|---|---|---|
| Fc sequence | V158 | F158 | CD32B | V158 | F158 |
| Ratio of Affinities > 1 Class I: Increased Binding to CD16; Decreased Binding to CD32B | | | | | |
| F243L | 4.79 | 3.44 | 0.84 | 5.70 | 4.10 |
| F243L P247L D270E N421K | 2.30 | 3.45 | 0.32 | 7.19 | 10.78 |
| F243L P247L N421K | 1.89 | 1.71 | 0.17 | 11.12 | 10.06 |
| F243L R255L D270E P396L | 1.75 | 1.64 | 0.38 | 4.61 | 4.32 |
| F243L D270E G316D R416G | 1.50 | 1.34 | 0.20 | 7.50 | 6.70 |
| F243L D270E K392T P396L | 3.16 | 2.44 | 0.44 | 7.18 | 5.55 |
| F243L D270E P396L Q419H | 1.46 | 1.15 | 0.26 | 5.62 | 4.42 |
| F243L R292P | 4.73 | | 0.12 | 39.4 | |
| F243L R292P | 4 | 1.67 | 0.16 | 25 | 10.44 |
| F243L R292P P300L | 6.69 | 2.3 | 0.32 | 20.9 | 7.19 |
| F243L R292P V305I | 2.56 | 1.43 | ND | >25 | >25 |

TABLE 3-continued

Detailed Binding Information for Exemplary Fc Variants

| | | | | Ratio of Affinities CD16A/ CD32B | |
|---|---|---|---|---|---|
| Fc sequence | CD16A V158 | CD16A F158 | CD32B | V158 | F158 |
| F243L R292P V305I P396L | 5.37 | 2.53 | 0.40 | 13.43 | 6.33 |
| P247L D270E N421K | 1.89 | 2.46 | 0.58 | 3.26 | 4.24 |
| R255L D270E R292G P396L | 1.39 | 1.30 | 0.65 | 2.14 | 2.00 |
| R255L D270E Y300L P396L | 1.52 | 1.74 | 0.87 | 1.75 | 2.00 |
| R255L D270E P396L | 1.34 | 1.65 | 0.87 | 1.54 | 1.90 |
| D270E | 1.25 | 1.48 | 0.39 | 3.21 | 3.79 |
| D270E G316D R416G | 2.18 | 2.49 | 0.78 | 2.79 | 3.19 |
| D270E K392T P396L | 1.81 | 2.28 | 0.79 | 2.29 | 2.89 |
| D270E P396L | 1.38 | 1.65 | 0.89 | 1.55 | 1.85 |
| D270E P396L G316D R416G | 1.22 | | 1.07 | 1.14 | |
| D270E P396L Q419H | 1.64 | 2.00 | 0.68 | 2.41 | 2.94 |
| V284M R292P K370N | 1.14 | 1.37 | 0.37 | 3.1 | 3.7 |
| R292G | 1.54 | | 0.25 | 6.2 | |
| R292P | 2.90 | | 0.25 | 11.60 | |
| R292P V305I | 1.32 | 1.28 | 0.37 | 3.6 | 3.46 |
| Class II: Decreased Binding to CD16; Greatly Decreased Binding to CD32B | | | | | |
| R292P | | 0.64 | 0.25 | | 2.56 |
| R292P F243L | | 0.6 | 0.12 | | 5.00 |
| Class III: Increased Binding to CD16; Unchanged Binding to CD32B | | | | | |
| F243I R292P Y300L V305I P396L | 10.9 | 3.12 | 1.05 | 10.4 | 2.97 |
| F243L R292P Y300L P396L | 10.06 | 5.62 | 1.07 | 9.40 | 5.25 |
| R292P V305I P396L | 1.85 | 1.90 | 0.92 | 2.01 | 2.07 |
| Class IV: Greatly Increased Binding to CD16; Increased Binding to CD32B | | | | | |
| F243L R292P Y300L V305I P396L | 10.06 | 8.25 | 1.38 | 7.29 | 5.98 |
| D270E G316D P396L R416G | 1.22 | | 1.07 | 1.14 | |
| Ratio of Affinities < 1 | | | | | |
| Class V: Unchanged Binding to CD16; Increased Binding to CD32B | | | | | |
| R255L P396L | 1.09 | | 2.22 | 0.49 | |
| Y300L | 1.01 | | 1.18 | | 0.99 |
| Class VI: Increased Binding to CD16; Greatly Increased Binding to CD32B | | | | | |
| F243L P396L | 1.49 | 1.60 | 2.22 | 0.67 | 0.72 |
| P247L N421K | 1.29 | 1.73 | 2.00 | 0.65 | 0.87 |
| R255L P396L | | 1.39 | 2.22 | 0.49 | 0.63 |
| R292P V305I | 1.59 | 2.11 | 2.67 | 0.60 | 0.79 |
| K392T P396L | 1.49 | 1.81 | 2.35 | 0.63 | 0.77 |
| P396L | 1.27 | 1.73 | 2.58 | 0.49 | 0.67 |
| P396L Q419H | 1.19 | 1.19 | 1.33 | 0.89 | 0.89 |
| Class VII: Decreased Binding to CD16; Increased/Unchanged Binding to CD32B | | | | | |
| D270E G316D P396L R416G | | 0.94 | 1.07 | | 0.88 |

In other embodiments, the molecules comprise a variant Fc region having one or more amino acid substitutions, which substitutions alter (relative to a wild-type Fc region) the binding of the variant Fc region, e.g., enhance the binding to an activating FcγR (such as FcγRIIA or FcγRIIIA) and/or reduce the binding to an inhibiting FcγR (such as FcγRIIB). Various Fc mutations having one or more amino acid changes were engineered and analyzed by surface plasmon resonance for $k_{off}$ as shown in Table 4. Dissociation rate constants for binding the various FcγR were determined by BIAcore analysis and directly compared with those for the wild-type Fc, with the ratio (x=WT $k_{off}$/mutant $k_{off}$) indicated in the right-hand columns of Table 4 with respect to each FcγR tested.

TABLE 4

Comparison Of $k_{off}$ Of Fc Mutants to Wild-Type Fc

| M | Amino Acid Change(s) | | | | $CD16A^V$ | $CD16A^F$ | $CD32A^H$ | CD32B |
|---|---|---|---|---|---|---|---|---|
| | One Amino Acid | | | | | | | |
| 1 | F243L | | | | 4.8 | 3.4 | 0.6 | 0.8 |
| 2 | D270E | | | | 1.3 | 1.5 | 2.2 | 0.4 |
| 3 | R292P | | | | 2.4 | 1.6 | 0.7 | 0.3 |
| 4 | S298N | | | | nd | nd | nt | 0.2 |
| 5 | Y300L | | | | 1.0 | 1.2 | 2.9 | 1.2 |
| 6 | V305I | | | | 0.9 | 0.6 | 1.3 | 1.2 |
| 7 | A330V | | | | 0.6 | 1.2 | 0.4 | 0.3 |
| 8 | P396L | | | | 1.3 | 1.7 | 1.6 | 2.6 |
| | Two Amino acids | | | | | | | |
| 9 | F243L | | P396L | | 2.2 | 2.0 | 1.5 | 1.6 |
| 10 | F243L R292P | | | | 4.0 | 1.7 | 0.5 | 0.2 |
| 11 | R292P V305I | | | | 1.3 | 1.3 | 0.8 | 0.4 |
| | Three Amino Acids | | | | | | | |
| 12 | F243L R292P Y300L | | | | 7.4 | 4.6 | 1.0 | 0.6 |
| 13 | F243L R292P V305I | | | | 2.6 | 1.4 | 0.2 | 0.1 |
| 14 | F243L R292P | | P396L | | 6.3 | 3.4 | 1.4 | 0.4 |
| 15 | R292P V305I P396L | | | | 1.9 | 1.9 | 1.5 | 0.9 |
| | Four Amino Acids | | | | | | | |
| 16 | F243L R292P Y300L | | P396L | | 10.1 | 5.6 | 1.7 | 1.1 |
| 17 | F243L R292P V305I P396L | | | | 4.0 | 2.3 | 0.8 | 0.4 |

TABLE 4-continued

Comparison Of $k_{off}$ Of Fc Mutants to Wild-Type Fc

| M | Amino Acid Change(s) | | | | | $CD16A^V$ | $CD16A^F$ | $CD32A^H$ | CD32B |
|---|---|---|---|---|---|---|---|---|---|
| | | | Five Amino Acids | | | | | | |
| 18 | F243L | R292P | Y300L | V305I | P396L | 10.1 | 8.3 | 3.2 | 1.4 |

Abbreviations:
M, Mutant Number;
nd, no detectable binding;
nt, not tested.
Values with ≥80% difference (≥0.8 fold) from wild-type in either direction are in bold.
Fc Mutant Numbers 2, 4, 8, 11 and 13 were identified directly by yeast display; all other mutants were constructed by site-directed mutagenesis.

There is also extensive guidance in the Antibody Engineering Technology Art concerning desirable modifications. Exemplary modifications that may be desirable in certain circumstances are listed below:

In a specific embodiment, in variant Fc regions, any amino acid modifications (e.g., substitutions) at any of positions 235, 240, 241, 243, 244, 247, 262, 263, 269, 298, 328, or 330 and preferably one or more of the following residues: A240, I240, L241, L243, H244, N298, I328 or V330. In a different specific embodiment, in variant Fc regions, any amino acid modifications (e.g., substitutions) at any of positions 268, 269, 270, 272, 276, 278, 283, 285, 286, 289, 292, 293, 301, 303, 305, 307, 309, 331, 333, 334, 335, 337, 338, 340, 360, 373, 376, 416, 419, 430, 434, 435, 437, 438 or 439 and preferably one or more of the following residues: H280, Q280, Y280, G290, S290, T290, Y290, N294, K295, P296, D298, N298, P298, V298, I300 or L300.

In a preferred embodiment, in variant Fc regions that bind an FcγR with an altered affinity, any amino acid modifications (e.g., substitutions) at any of positions 255, 256, 258, 267, 268, 269, 270, 272, 276, 278, 280, 283, 285, 286, 289, 290, 292, 293, 294, 295, 296, 298, 300, 301, 303, 305, 307, 309, 312, 320, 322, 326, 329, 330, 332, 331, 333, 334, 335, 337, 338, 339, 340, 359, 360, 373, 376, 416, 419, 430, 434, 435, 437, 438 or 439. Preferably, the variant Fc region has any of the following residues: A256, N268, Q272, D286, Q286, S286, A290, S290, A298, M301, A312, E320, M320, Q320, R320, E322, A326, D326, E326, N326, S326, K330, T339, A333, A334, E334, H334, L334, M334, Q334, V334, K335, Q335, A359, A360 or A430.

In a different embodiment, in variant Fc regions that bind an FcγR (via its Fc region) with a reduced affinity, any amino acid modifications (e.g., substitutions) at any of positions 252, 254, 265, 268, 269, 270, 278, 289, 292, 293, 294, 295, 296, 298, 300, 301, 303, 322, 324, 327, 329, 333, 335, 338, 340, 373, 376, 382, 388, 389, 414, 416, 419, 434, 435, 437, 438 or 439.

In a different embodiment, in variant Fc regions that bind an FcγR (via its Fc region) with an enhanced affinity, any amino acid modifications (e.g., substitutions) at any of positions 280, 283, 285, 286, 290, 294, 295, 298, 300, 301, 305, 307, 309, 312, 315, 331, 333, 334, 337, 340, 360, 378, 398 or 430. In a different embodiment, in variant Fc regions that binds FcγRIIA with an enhanced affinity, any of the following residues: A255, A256, A258, A267, A268, N268, A272, Q272, A276, A280, A283, A285, A286, D286, Q286, S286, A290, S290, M301, E320, M320, Q320, R320, E322, A326, D326, E326, S326, K330, A331, Q335, A337 or A430.

In other embodiments, the invention encompasses the use of any Fc variant known in the art, such as those disclosed in Jefferis et al. (2002) Immunol Lett 82:57-65; Presta et al. (2002) Biochem Soc Trans 30:487-90; Idusogie et al. (2001) J Immunol 166:2571-75; Shields et al. (2001) J Biol Chem 276:6591-6604; Idusogie et al. (2000) J Immunol 164:4178-84; Reddy et al. (2000) J Immunol 164:1925-33; Xu et al. (2000) Cell Immunol 200:16-26; Armour et al. (1999) Eur J Immunol 29:2613-24; Jefferis et al. (1996) Immunol Lett 54:101-04; Lund et al. (1996) J Immunol 157:4963-69; Hutchins et al. (1995) Proc. Natl. Acad. Sci. (U.S.A.) 92:11980-84; Jefferis et al. (1995) Immunol Lett. 44:111-17; Lund et al. (1995) FASEB J 9:115-19; Alegre et al. (1994) Transplantation 57:1537-43; Lund et al. (1992) Mol Immunol 29:53-59; Lund et al. (1991) J. Immunol 147:2657-62; Duncan et al. (1988) Nature 332:563-64; U.S. Pat. Nos. 5,624,821; 5,885,573; 6,194,551; 7,276,586; and 7,317,091; and PCT Publications WO 00/42072 and PCT WO 99/58572.

Preferred variants include one or more modifications at any of positions: 228, 230, 231, 232, 233, 234, 235, 239, 240, 241, 243, 244, 245, 247, 262, 263, 264, 265, 266, 271, 273, 275, 281, 284, 291, 296, 297, 298, 299, 302, 304, 305, 313, 323, 325, 326, 328, 330 or 332.

Particularly preferred variants include one or more modifications selected from groups A-AI:
A. 228E, 228K, 228Y or 228G;
B. 230A, 230E, 230Y or 230G;
C. 231E, 231K, 231Y, 231P or 231G;
D. 232E, 232K, 232Y, 232G;
E. 233D;
F. 234I or 234F;
G. 235D, 235Q, 235P, 235I or 235V;
H. 239D, 239E, 239N or 239Q;
I. 240A, 240I, 240M or 240T;
J. 243R, 243, 243Y, 243L, 243Q, 243W, 243H or 243I;
K. 244H;
L. 245A;
M. 247G, 247V or 247L;
N. 262A, 262E, 262I, 262T, 262E or 262F;
O. 263A, 263I, 263M or 263T;
P. 264F, 264E, 264R, 264I, 264A, 264T or 264W;
Q. 265F, 265Y, 265H, 265I, 265L, 265T, 265V, 265N or 265Q;
R. 266A, 266I, 266M or 266T;
S. 271D, 271E, 271N, 271Q, 271K, 271R, 271S, 271T, 271H, 271A, 271V, 271L, 271I, 271F, 271M, 271Y, 271W or 271G;
T. 273I;
U. 275L or 275W;
V. 281D, 281K, 281Y or 281P;
W. 284E, 284N, 284T, 284L, 284Y or 284M;
X. 291D, 291E, 291Q, 291T, 291H, 291I or 291G;

Y. 299A, 299D, 299E, 299F, 299G, 299H, 299I, 299K, 299L, 299M, 299N, 299P, 299Q, 299R, 299S, 299V, 299W or 299Y;
Z. 302I;
AA. 304D, 304N, 304T, 304H or 304L
AB. 305I;
AC. 313F;
AD. 323I;
AE. 325A, 325D, 325E, 325G, 325H, 325I, 325L, 325K, 325R, 325S, 325F, 325M, 325T, 325V, 325Y, 325W or 325P;
AF. 328D, 328Q, 328K, 328R, 328S, 328T, 328V, 328I, 328Y, 328W, 328P, 328G, 328A, 328E, 328F, 328H, 328M or 328N;
AG. 330L, 330Y, 330I or 330V;
AH. 332A, 332D, 332E, 332H, 332N, 332Q, 332T, 332K, 332R, 332S, 332V, 332L, 332F, 332M, 332W, 332P, 332G or 332Y; and
AI. 336E, 336K or 336Y.

Still more particularly preferred variants include one or more modifications selected from Groups 1-105:

| Group | Variant |
|---|---|
| 1 | A330L/I332E |
| 2 | D265F/N297E/I332E |
| 3 | D265Y/N297D/I332E |
| 4 | D265Y/N297D/T299L/I332E |
| 5 | F241E/F243Q/V262T/V264F |
| 6 | F241E/F243Q/V262T/V264E/I332E |
| 7 | F241E/F243R/V262E/V264R |
| 8 | F241E/F243R/V262E/V264R/I332E |
| 9 | F241E/F243Y/V262T/V264R |
| 10 | F241E/F243Y/V262T/V264R/I332E |
| 11 | F241L/F243L/V262I/V264I |
| 12 | F241L/V262I |
| 13 | F241R/F243Q/V262T/V264R |
| 14 | F241R/F243Q/V262T/V264R/I332E |
| 15 | F241W/F243W/V262A/V264A |
| 16 | F241Y/F243Y/V262T/V264T |
| 17 | F241Y/F243Y/V262T/V264T/N297D/I332E |
| 18 | F243L/V262I/V264W |
| 19 | P243L/V264I |
| 20 | L328D/I332E |
| 21 | L328E/I332E |
| 22 | L328H/I332E |
| 23 | L328I/I332E |
| 24 | L328M/I332E |
| 25 | L328N/I332E |
| 26 | L328Q/I332E |
| 27 | L328T/I332E |
| 28 | L328V/I332E |
| 29 | N297D/A330Y/I332E |
| 30 | N297D/I332E |
| 31 | N297D/I332E/S239D/A330L |
| 32 | N297D/S298A/A330Y/I332E |
| 33 | N297D/T299L/I332E |
| 34 | N297D/T299F/I332E/N297D/T299H/I332E |
| 35 | N297D/T299I/I332E |
| 36 | N297D/T299L/I332E |
| 37 | N297D/T299V/I332E |
| 38 | N297E/I332E |
| 39 | N297S/I332E |
| 40 | P230A/E233D/I332E |
| 41 | P244H/P245A/P247V |
| 42 | S239D/A330L/I332E |
| 43 | S239D/A330Y/I332E |
| 44 | S239D/A330Y/I332E/K326E |
| 45 | S239D/A330Y/I332E/K326T |
| 46 | S239D/A330Y/I332E/L234I |
| 47 | S239D/A330Y/I332E/L235D |
| 48 | S239D/A330Y/I332E/V240I |
| 49 | S239D/A330Y/I332E/V264T |
| 50 | S239D/A330Y/I332E/V266I |
| 51 | S239D/D265F/N297D/I332E |
| 52 | S239D/D265H/N297D/I332E |
| 53 | S239D/D265I/N297D/I332E |
| 54 | S239D/D265L/N297D/I332E |
| 55 | S239D/D265T/N297D/I332E |
| 56 | S239D/D265V/N297D/I332E |
| 57 | S239D/D265Y/N297D/I332E |
| 58 | S239D/I332D |
| 59 | S239D/I332E |
| 60 | S239D/I332E/A330I |
| 61 | S239D/I332N |
| 62 | S239D/I332Q |
| 63 | S239D/N297D/I332E |
| 64 | S239D/N297D/I332E/A330Y |
| 65 | S239D/N297D/I332E/A330Y/F241S/F243H/V262T/V264T |
| 66 | S239D/N297D/I332E/K326E |
| 67 | S239D/N297D/I332E/L235D |
| 68 | S239D/S298A/I332E |
| 69 | S239D/V264I/A330L/I332E |
| 70 | S239D/V264I/I332E |
| 71 | S239D/V264I/S298A/I332E |
| 72 | S239E/D265N |
| 73 | S239E/D265Q |
| 74 | S239E/I332D |
| 75 | S239E/I332E |
| 76 | S239E/I332N |
| 77 | S239E/I332Q |
| 78 | S239E/N297D/I332E |
| 79 | S239E/V264I/A330Y/I332 E |
| 80 | S239E/V264I/I332 E |
| 81 | S239E/V264I/S298A/A330Y/I332E |
| 82 | S239N/A330L/I332E |
| 83 | S239N/A330Y/I332E |
| 84 | S239N/I332D |
| 85 | S239N/I332E |
| 86 | S239N/I332N |
| 87 | S239N/I332Q |
| 88 | S239N1S298A/I332E |
| 89 | S239Q/I332D |
| 90 | S239Q/I332E |
| 91 | S239Q/I332N |
| 92 | S239Q/I332Q |
| 93 | S239Q/V264I/I332E |
| 94 | S298A/I332E |
| 95 | V264E/N297D/I332E |
| 96 | V264I/A330L/I332E |
| 97 | V264I/A330Y/I332E |
| 98 | V264I/I332E |
| 99 | V264I/S298A/I332E |
| 100 | Y296D/N297D/I332E |
| 101 | Y296E/N297D/I332 E |
| 102 | Y296H/N297D/I332E |
| 103 | Y296N/N297D/I332E |
| 104 | Y296Q/N297I/I332E |
| 105 | Y296T/N297D/I332E. |

Effector function can be modified by techniques such as those described in the Antibody Engineering Technology Art, or by other means. For example, cysteine residue(s) may be introduced in the Fc region, thereby allowing interchain disulfide bond formation in this region, resulting in the generation of a homodimeric antibody that may have improved internalization capability and/or increased complement-mediated cell killing and ADCC. See Caron et al. (1992) J. Exp Med. 176:1191-1195; and B. Shopes (1992) J. Immunol. 148:2918-2922. Homodimeric antibodies with enhanced anti-tumor activity may also be prepared using heterobifunctional cross-linkers as described in Wolff et al. (1993) Cancer Research 53:2560-2565. Alternatively, an antibody can be engineered which has dual Fc regions and may thereby have enhanced complement lysis and ADCC capabilities. Stevenson et al. (1989) Anti-Cancer Drug Design 3:219-230.

B2. Sequence Modifications

Generally, sequence modifications may be the substitution, deletion, or addition of one or more residues in the antibody or polypeptide that results in a change in the amino acid sequence as compared to the native sequence. Guidance in determining which amino acid residue may be inserted, substituted or deleted without adversely affecting the desired activity may be found by comparing the sequence of the antibody or polypeptide with that of homologous known protein molecules and minimizing the number of amino acid sequence changes made in regions of high homology. The variation allowed may be determined by systematically making insertions, deletions or substitutions of amino acids in the sequence and testing the resulting variants for activity exhibited by the full-length or mature native sequence.

Amino acid substitutions may involve the conservative or non-conservative substitution of one or more residues. Such substitutions are well-known in the art, for example a conservative substitution entails replacing an amino acid with another amino acid having similar structural and/or chemical properties, such as the replacement of a leucine with a serine. Non-conservative substitutions generally entail replacing an amino acid with another amino acid having different structural and/or chemical properties, for example an acidic amino acid (e.g., Glu or Asp) may be replaced with a basic amino acid (e.g., Lys or Asn).

A particularly preferred type of substitutional variant involves substituting one or more hypervariable region residues of a parent antibody (e.g., a humanized or human antibody), in order to obtain a variant antibody having improved biological properties relative to the parent antibody. A convenient way for generating such substitutional variants involves affinity maturation using phage display. Briefly, several hypervariable region sites are mutated to generate all possible amino substitutions at each site, the antibody variants thus generated are displayed on phage, and the phage-displayed variants are then screened for their biological activity (e.g., binding affinity). In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and its antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

The modification may also involve the incorporation (e.g., by substitution or addition) of unnatural amino acids, for example by methods such as those described in, e.g., Wang et al. (2002) Chem. Comm. 1:1-11; Wang et al. (2001) Science 292:498-500; and van Hest et al. (2001) Chem. Comm. 19:1897-1904. Alternative strategies focus on the enzymes responsible for the biosynthesis of amino acyl-tRNA, as described in, e.g., Tang et al. (2001) J. Am. Chem. 123(44):11089-11090; and Kiick et al. (2001) FEBS Lett. 505(3):465.

In a preferred embodiment, at least 1, 2, 3, 4, 5, 6, 7, 8, 9, 10, 11, 12, 13, 14, 15, 20, 25, 30, 35, 40, 45, or 50 amino acid residues have been modified. Additionally or alternatively, such modifications may be characterized as having no more than 1, 2, 3, 4, 5, 6, 7, 8, 9, 10, 11, 12, 13, 14, 15, 20, 25, 30, 35, 40, 45, or 50 modified amino acid residues. In a particularly preferred embodiment, at least 1 but no more than 10 residues have been modified. Additionally or alternatively, such modifications may be characterized as having no more than 15, 14, 13, 12, 11, 10, 9, 8, 7, 6, 5, 4, 3 or 2 modified amino acid residues. The modifications may be all substitutions, all deletions, all additions, or any combination of substitutions, deletions, or additions.

Nucleic acid molecules encoding amino acid sequence variants may be prepared by a variety of methods known in the art. These methods include, but are not limited to, isolation from a natural source (in the case of naturally occurring amino acid sequence variants) or preparation by oligonucleotide-mediated (or site-directed) mutagenesis, restriction selection mutagenesis, PCR mutagenesis, and cassette mutagenesis of an earlier prepared variant or a non-variant version of the antibody.

B3. Other Modifications

The polypeptide variants (especially antibody variants) of the present invention include analogs and derivatives that are modified, e.g., by the covalent attachment of any type of molecule as long as such covalent attachment permits the antibody to retain its epitope binding immunospecificity. For example, but not by way of limitation, the derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques, including, but not limited to specific chemical cleavage, acetylation, formylation, metabolic synthesis in the presence of tunicamycin, etc. Additionally, the analog or derivative can contain one or more unnatural amino acids.

The antibodies and polypeptides may be modified by introducing one or more glycosylation sites into the antibodies, deleting one or more glycosylation sites from the antibodies, or shifting an existing glycosylation site on the antibodies, preferably without altering the desired functionality of the antibodies, e.g., binding activity. Glycosylation sites may be introduced into, or deleted from, the variable and/or constant region of the antibodies, by methods known in the art. For example, a glycosylation site may be introduced into an antibody of the invention by modifying or mutating an amino acid sequence of the antibody so that the desired sequence (e.g., Asn-X-Thr/Ser) is obtained, and a glycosylation site may be shifted by modifying position 296 in the Fc region, so that position 296 and not position 297 is glycosylated. Methods of modifying the carbohydrate content (glycosylation) of proteins are well known in the art, for example as described in U.S. Pat. Nos. 6,472,511 and 6,218,149; U.S. Patent Publication Nos. 20030115614 and 20020028486; EP 0359096 B1; and WO 03/035835.

In some embodiments, molecules of the invention are engineered to comprise an altered glycosylation pattern or an altered glycoform. Engineered glycoforms may be useful for a variety of purposes, including, but not limited to, enhancing effector function. Engineered glycoforms may be generated by any method known to one skilled in the art, for example by using engineered or variant expression strains, by co-expression with one or more enzymes, for example, N-acetylglucosaminyltransferase III (GnT-III), by expressing an antibody of the invention in various organisms or cell lines from various organisms, or by modifying carbohydrate(s) after the antibody has been expressed and purified.

Methods for generating engineered glycoforms are known in the art, and include but are not limited to those described in, e.g., Okazaki et al. (2004) JMB 336:1239-1249; Shinkawa et al. (2003) J Biol Chem 278:3466-3473; Shields et al. (2002) J Biol Chem 277:26733-26740; Davies et al. (2001) Biotechnol Bioeng 74:288-294; Umana et al. (1999) Nat. Biotechnol 17:176-180; U.S. Pat. No. 6,602,684; U.S. Patent Publication Nos. 20030157108, 20030115614, and 20030003097; WO 02/311140; WO 02/30954; WO 01/292246; WO 00/61739; Potillegent™ technology available from Biowa, Inc. (Princeton, N.J.); and GlycoMAb™ glycosylation engineering technology available from GLYCART biotechnology AG (Zurich, Switzerland).

B4. Polypeptide Conjugates

The polypeptides of the present invention may be recombinantly fused or chemically conjugated (including both covalent and non-covalent conjugations) to heterologous polypeptides or portions thereof to generate fusion proteins. Preferably, the polypeptide of the present invention (especially an antibody) is fused to at least 10, at least 15, at least 20, at least 25, at least 30, at least 40, at least 50, at least 60, at least 70, at least 80, at least 90 or at least 100 amino acids of the heterologous polypeptide to generate a desired fusion protein. The fusion does not necessarily need to be direct, but may occur through linker sequences. Polypeptides of the present invention may also be attached to solid supports or semi-solid matrices, which are particularly useful for immunoassays or purification of the target antigen. Such supports and matrices include, but are not limited to, glass, cellulose, polyacrylamide, agarose beads, acrylamide beads, nylon, polystyrene, polyvinyl chloride or polypropylene. Attachment may be accomplished, for example, by methods described in Methods in Enzymology, 44 (1976).

The antibodies and polypeptides may be conjugated to a therapeutic agent in order to modify a given biological response, affect (e.g., increase) the serum half-life of the therapeutic agent, or target the therapeutic agent to a particular subset of cells. They may also be fused to marker sequences (e.g., a hexa-histidine peptide or a "flag" tag) to facilitate purification. Techniques for conjugating such therapeutic moieties to antibodies are well known; see, e.g., Hellstrom et al., "Antibodies For Drug Delivery", in Controlled Drug Delivery (2nd ed., Robinson et al. (eds.), 1987, pp. 623-53, Marcel Dekker, Inc.).

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of molecules of the invention (e.g., antibodies with higher affinities and lower dissociation rates). Antibodies and polypeptides of the invention, or their encoding nucleic acids, may be further altered by being subjected to random mutagenesis by error-prone PCR, random nucleotide insertion or other methods prior to recombination. One or more portions of a polynucleotide encoding a molecule of the invention, may be recombined with one or more components, motifs, sections, parts, domains, fragments, etc. of one or more heterologous molecules.

B5. Fragments

The invention additionally provides antibody and other polypeptide fragments. Such fragments may be truncated at the N-terminus or C-terminus, or may lack internal residues, for example, when compared with a full length native antibody or protein. Certain fragments may lack amino acid residues that are not essential for a desired biological activity. These fragments may be prepared by any of a number of conventional techniques. Desired peptide fragments may be chemically synthesized. An alternative approach involves generating antibody or polypeptide fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired antibody or polypeptide fragment, by polymerase chain reaction (PCR). Oligonucleotides that define the desired termini of the DNA fragment are employed at the 5' and 3' primers in the PCR. Preferably, antibody and polypeptide fragments share at least one biological and/or immunological activity with the native antibody or polypeptide disclosed herein.

In some embodiments, a polypeptide of the invention further comprises a dimerization domain, which can comprise a dimerization sequence, and/or sequence comprising one or more cysteine residues. In some embodiments, the dimerization domain will be located between an antibody heavy chain or light chain variable domain and at least a portion of a viral coat protein, and one or more disulfide bond and/or a single dimerization sequence may be present in the dimerization domain to provide for bivalent display. In some embodiments, heavy chains of a F(ab)$_2$ will dimerize at a dimerization domain not including a hinge region. The dimerization domain may comprise a leucine zipper sequence.

In another embodiment, the polypeptide fragments of the present invention comprise an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 30 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of another polypeptide. In a specific embodiment, a fragment of a polypeptide retains at least one function of the polypeptide.

B6. Diabodies and DARTs

Diabodies and dual affinity retargeting reagents ("DARTs") are also provided by the present invention. The diabodies and DARTs comprise antigen binding domains generally derived from the antibodies and polypeptides of the invention. The design and construction of diabodies and DARTs is described in, for example, U.S. Provisional Patent Application Nos. 61/019,051 filed on Jan. 4, 2008 and 60/945,523 filed on Jun. 21, 2007; U.S. patent application Ser. No. 11/409,339 filed on Apr. 17, 2006; Marvin et al. (2005) Acta Pharmacol. Sin. 26:649-658; Olafsen et al. (2004) Prot. Engr. Des. Sel. 17:21-27; Holliger et al. (1993) Proc. Natl. Acad. Sci. (U.S.A.) 90:6444-6448. Each polypeptide chain of a diabody molecule comprises a $V_L$ domain and a $V_H$ domain, from the same or different antibodies, which are covalently linked such that the domains are constrained from self assembly. Interaction of two of the polypeptide chains will produce two $V_L$-$V_H$ pairings, forming two epitope binding sites, i.e., a bivalent molecule. Neither the $V_H$ or $V_L$ domain is constrained to any position within the polypeptide chain, nor are the domains restricted in their relative positions to one another; the only restriction is that a complementary polypeptide chain be available in order to form functional diabody. The domains may be separated by a peptide linker, and the polypeptide chains may be engineered to comprise at least one cysteine residue on each chain, so that interchain disulfide bonds may be formed to stabilize the diabody.

Where the $V_L$ and $V_H$ domains are derived from the same antibody, the two complementary polypeptide chains may be identical, resulting in a bivalent monospecific antibody, or may be different, resulting in a bivalent bispecific antibody (e.g., one that binds ton two different epitopes on the same antigen). Where the $V_L$ and $V_H$ domains are derived from antibodies specific for different antigens, formation of a functional bispecific diabody requires the interaction of two different polypeptide chains, i.e., formation of a heterodimer. In a particular embodiment, at least one epitope binding site of the diabody is specific for an antigen on a particular cell, such as a B-cell or T-cell, a phagocytotic cell, a natural killer (NK) cell or a dendritic cell.

In various embodiments, one or more of the polypeptide chains of the diabody comprises an Fc domain. Fc domains in the polypeptide chains of the diabody molecules preferentially dimerize, resulting in the formation of a diabody molecule that exhibits immunoglobulin-like properties, e.g., Fc-FcγR interactions. Fc comprising diabodies may be dimers, e.g., comprised of two polypeptide chains, each comprising a $V_H$ domain, a $V_L$ domain and an Fc domain. In various embodiments, one or more of the polypeptide chains of the diabody comprises a hinge domain, which may be derived from any immunoglobulin isotype or allotype including IgA, IgD, IgG, IgE and IgM. In preferred embodiments, the hinge domain is derived from IgG, wherein the IgG isotype is IgG1, IgG2, IgG3 or IgG4, or an allotype thereof. The hinge domain may be engineered into a polypeptide chain in any position relative to other domains or portions of the chain, and in certain circumstances may be engineered together with an Fc domain such that the diabody molecule comprises a hinge-Fc domain.

In other embodiments, diabody molecules comprising Fc domains may be tetramers, which may comprise two "heavier" polypeptide chains (i.e. a polypeptide chain comprising a $V_L$, a $V_H$ and an Fc domain), and two "lighter" polypeptide chains (i.e., a polypeptide chain comprising a $V_L$ and a $V_H$). Such lighter and heavier chains may interact to form a monomer, and interact via their unpaired Fc domains to form an Ig-like molecule, which may be a DART molecule. Such an Ig-like diabody is tetravalent and may be monospecific, bispecific or tetraspecific. The Ig-like DART species has unique properties, because its domains may be designed to bind to the same epitope (so as to form a tetravalent, mono-epitope specific Ig-like DART capable of binding four identical antigen molecules), or to different epitopes or antigens. For example, its domains may be designed to bind to two epitopes of the same antigen (so as to form a tetravalent, mono-antigen specific, bi-epitope specific Ig-like DART), or to epitopes of different antigen molecules so as to form a tetravalent Ig-like DART having a pair of binding sites specific for a first antigen and a second pair of binding sites specific for a second antigen). Hybrid molecules having combinations of such attributes can be readily produced.

Although not intending to be bound by a particular mechanism of action, the diabody molecules of the invention exhibit enhanced therapeutic efficacy relative to therapeutic antibodies known in the art, in part, due to the ability of diabody to immunospecifically bind a target cell which expresses a particular antigen (e.g., FcγR) at reduced levels, for example, by virtue of the ability of the diabody to remain on the target cell longer due to an improved avidity of the diabody-epitope interaction. Thus, the diabodies of the invention have particular utility in treatment, prevention or management of a disease or disorder, such as cancer, in a sub-population, wherein the target antigen is expressed at low levels in the target cell population.

Due to their increased valency, low dissociation rates and rapid clearance from the circulation (for diabodies of small size, at or below ~50 kDa), diabody molecules known in the art have also shown particular use in the filed of tumor imaging. (Fitzgerald et al. (1997) Protein Eng. 10:1221). Of particular importance is the cross linking of differing cells, for example the cross linking of cytotoxic T cells to tumor cells. (Staerz et al. (1985) Nature 314:628-631; Holliger et al. (1996) Protein Eng. 9:299-305). Diabody epitope binding domains may also be directed to a surface determinant of any immune effector cell such as CD3, CD16, CD32, or CD64, which are expressed on T lymphocytes, natural killer (NK) cells or other mononuclear cells. In many studies, diabody binding to effector cell determinants, e.g., Fcγ receptors (FcγR), was also found to activate the effector cell. (Holliger et al. (1996) Protein Eng. 9:299-305; Holliger et al. (1999) Cancer Res. 59:2909-2916). Normally, effector cell activation is triggered by the binding of an antigen bound antibody to an effector cell via Fc-FcγR interaction; thus, in this regard, diabody molecules of the invention may exhibit Ig-like functionality independent of whether they comprise an Fc domain. By cross-linking tumor and effector cells, the diabody not only brings the effector cell within the proximity of the tumor cells but leads to effective tumor killing Cao and Lam (2003) Adv. Drug. Deliv. Rev. 55:171-97.

The diabody molecules of the present invention can be produced using a variety of methods, including de novo protein synthesis and recombinant expression of nucleic acids encoding the binding proteins. The desired nucleic acid sequences can be produced by recombinant methods (e.g., PCR mutagenesis of an earlier prepared variant of the desired polynucleotide) or by solid-phase DNA synthesis. Preferably recombinant expression methods are used. In one aspect, the invention provides a polynucleotide that comprises a sequence encoding a CD16A $V_H$ and/or $V_L$; in another aspect, the invention provides a polynucleotide that comprises a sequence encoding a CD32B $V_H$ and/or $V_L$. Because of the degeneracy of the genetic code, a variety of nucleic acid sequences encode each immunoglobulin amino acid sequence, and the present invention includes all nucleic acids encoding the binding proteins described herein.

B7. Production of Antibodies

The antibodies of the preferred embodiments of the invention may be produced or obtained in any of a variety of ways. For example, such antibodies may be obtained from plasma, synthetically, recombinantly or transgenically, via cell (e.g., hybridoma culture), etc. The production of synthetic proteins has been described in, e.g., Dawson et al. (2000) Ann. Rev Biochem. 69:923-960; Wilken et al. (1998) Curr. Opin. Biotechnol. 9(4):412-426; and Kochendoerfer et al. (1999) Curr. Opin. Chem. Biol. 3(6):665-671.

Production of recombinant and transgenic antibodies has been described in, e.g., Wang et al. (2007) IDrugs 10(8): 562-565; Hagemeyer et al. (2007) Semin. Thromb. Hemost. 33(2):185-195; Rasmussen et al. (2007) Biotechnol. Lett. 29(6):845-852; Gasser et al. (2007) Biotechnol. Lett. 29(2): 201-212; Aubrey et al. (2006) J. Soc. Biol. 200(4):345-354; Laffly et al. (2006) J. Soc. Biol. 200(4):325-343; Jefferis (2005) Biotechnol Prog. 21(1):11-16; Smith et al. (2004) J. Clin. Pathol. 57(9):912-917; Kipriyanov et al. (2004) Mol Biotechnol. 26(1):39-60; Fischer et al. (2003) Vaccine 21(7-8):820-825; Maynard et al. (2000) Ann. Rev. Biomed. Eng. 2:339-376; Young et al. (1998) Res. Immunol. 149(6):609-610; and Hudson (1998) Curr. Opin. Biotechnol. 9(4):395-402.

Production of antibodies via cell (e.g., hybridoma) culture has been described in, e.g., Laffly et al. (2006), supra; Aldington et al. (2007) J. Chromatogr. B Analyt. Technol. Biomed. Life Sci. 848(1):64-78; S. S. Farid (2006) J. Chromatogr. B Analyt. Technol. Biomed. Life Sci. 848(1):8-18; Birch et al. (2006) Adv. Drug Deliv. Rev. 58(5-6):671-685; Even et al. (2006) Trends Biotechnol. 24(3):105-108; Graumann et al. (2006) Biotechnol. J. 1(2):164-86; U.S. Pat. No. 7,112,439; and U.S. Patent Publications Nos. 20070037216 and 20040197866.

Antibodies may be produced via phage display methods, such as those disclosed in, e.g., Brinkman et al. (1995) J. Immunol. Methods 182:41-50; Ames et al. (1995) J. Immunol. Methods 184:177-86; Kettleborough et al. (1994) Eur. J. Immunol. 24:952-58; Persic et al. (1997) Gene 187:9-18; Burton et al. (1994) Advances in Immunology 57:191-280; PCT Publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108. Phage display technology can also be used to increase the affinity of an antibody for its antigen. The technology, referred to as affinity maturation, employs mutagenesis or CDR walking and re-selection using the cognate antigen to identify antibodies that bind with higher affinity to the antigen when compared with the initial or parental antibody. See, e.g., Glaser et al. (1992) J. Immunology 149:3903; Wu et al. (1998) Proc. Natl. Acad. Sci. (U.S.A.) 95:6037; Yelton et al. (1995) J. Immunology 155: 1994; Schier et al. (1996) J. Mol. Bio. 263:551.

Monoclonal antibodies may be made by a variety of methods known to those skilled in the art, for example, hybridoma methods as described in, e.g., Kohler et al. (1975) Nature 256:495, Kozbor et al. (1983) Immunology Today 4:72, or Cole et al. (1985) Monoclonal Antibodies and Cancer Therapy, Alan R. Liss, Inc., pp. 77-96, or recombinant DNA methods as described in, e.g., U.S. Pat. No. 4,816,567, or the antibodies may be isolated from phage antibody libraries using the techniques described in Clackson et al. (1991) Nature 352:624-628 and Marks et al. (1991) J. Mol. Biol. 222:581-597, for example Various procedures well known in the art may be used for the production of polyclonal antibodies to an antigen of interest. For example, various host animals can be immunized by injection with an antigen of interest or derivative thereof, including but not limited to rabbits, sheep, goats, dogs, mice, rats, and guinea pigs, and after allowing for an immunological response, the antibodies can be identified from the sera of the immunized animals.

Bispecific antibodies may also be made, for example through the co-expression of two immunoglobulin heavy chain-light chain pairs, where the two chains have different specificities, followed by purification of the desired molecule using affinity chromatography, as described by Milstein et al. (1983) Nature 305:537-39, WO 93/08829, Traunecker et al. (1991) EMBO J. 10:3655-59. In a different approach, antibody variable domains with the desired binding specificities (antibody-antigen combining sites) are fused to immunoglobulin constant domain sequences, for example to a heavy chain constant domain, comprising at least part of the hinge, $C_{H2}$, and $C_{H3}$ regions. The nucleic acids encoding these fusions may be inserted into the same or different expression vectors, and are expressed in a suitable host organism.

Fully human antibodies (also referred to as completely human antibodies) may be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. An overview of this technology for producing human antibodies is described in, for example, Lonberg and Huszar (1995) Int. Rev. Immunol. 13:65-93, and U.S. Pat. No. 5,633,425. Fully human antibodies can also be produced using other techniques known in the art, including phage display libraries, as described by Hoogenboom and Winter (1991) J. Mol. Biol. 227:381 and Marks et al. (1991) J. Mol. Biol. 222:581. Fully human antibodies may also be obtained commercially from, for example, Abgenix, Inc. (Freemont, Calif.) and Genpharm (San Jose, Calif.). Fully human antibodies that recognize a selected epitope may be generated using a technique referred to as "guided selection." In this approach a selected non-human monoclonal antibody, e.g., a mouse antibody, is used to guide the selection of a completely human antibody recognizing the same epitope, as described by, e.g., Jespers et al. (1994) Biotechnology 12:899-903.

The present invention also includes polynucleotides that encode the molecules of the invention, including the polypeptides and antibodies, as well as vectors comprising the polynucleotides, and host cells comprising the vectors. The polynucleotides encoding the molecules of the invention may be obtained, and the nucleotide sequence of the polynucleotides determined, by any method known in the art, for example, recombinant DNA techniques, site directed mutagenesis, PCR, etc. In one embodiment, human libraries or any other libraries available in the art, can be screened by standard techniques known in the art, to clone the nucleic acids encoding the molecules of the invention.

B8. Characterization of Antibodies

The antibodies of the present invention may be characterized in a variety of ways. In particular, antibodies of the invention may be assayed for the ability to immunospecifically bind to an antigen, e.g., HER2/neu, or, where the molecule comprises an Fc domain (or portion thereof) for the ability to exhibit Fc-FcγR interactions, i.e. specific binding of an Fc domain (or portion thereof) to an FcγR. Such an assay may be performed in solution (e.g., Houghten (1992) Bio/Techniques 13:412-421), on beads (Lam (1991) Nature 354:82-84), on chips (Fodor (1993) Nature 364:555-556), on bacteria (U.S. Pat. No. 5,223,409), on spores (U.S. Pat. Nos. 5,571,698; 5,403,484; and 5,223,409), on plasmids (Cull et al. (1992) Proc. Natl. Acad. Sci. (U.S.A.) 89:1865-1869) or on phage (Scott and Smith (1990) Science 249: 386-390; Devlin (1990) Science 249:404-406; Cwirla et al. (1990) Proc. Natl. Acad. Sci. (U.S.A.) 87:6378-6382; and Felici (1991) J. Mol. Biol. 222:301-310). Molecules that have been identified to immunospecifically bind to an antigen can then be assayed for their specificity and affinity for the antigen.

Immunoassays which can be used to analyze immunospecific binding, cross-reactivity, and Fc-FcγR interactions include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunochromatographic assays, immunodiffusion assays, agglutination assays, complement-fixation assays, immunoradiometric assays, fluorescent immunoassays, and protein A immunoassays, etc. (see, e.g., Ausubel et al., 2008, Current Protocols in Molecular Biology).

Binding affinity for a target antigen is typically measured or determined by standard antibody-antigen assays, such as Biacore competitive assays, saturation assays, or immunoassays such as ELISA or RIA.

Preferably, fluorescence activated cell sorting (FACS), using any of the techniques known to those skilled in the art, is used for immunological or functional based assays to characterize molecules of the invention. Flow sorters are capable of rapidly examining a large number of individual cells that have been bound, e.g., opsonized, by molecules of the invention (e.g., 10-100 million cells per hour). Additionally, specific parameters used for optimization of antibody behavior, include but are not limited to, antigen concentration, kinetic competition time, or FACS stringency, each of which may be varied in order to select for antibody molecules which exhibit specific binding properties. Flow cytometers for sorting and examining biological cells are well known in the art. Known flow cytometers are described, for example, in U.S. Pat. Nos. 4,347,935; 5,464,581; 5,483,469; 5,602,039; 5,643,796; and 6,211,477. Other known flow cytometers are the FACS Vantage™ system sold by Becton Dickinson and Company, and the COPAS™ system sold by Union Biometrica.

Surface plasmon resonance-based assays may be used to characterize the kinetic parameters of an antigen-binding domain or Fc-FcγR binding. Any method known to those skilled in the art may be used, for example the technology described in, e.g., Dong et al. (2002) Review in Mol. Biotech. 82:303-323; Mullet et al. (2000) Methods 22:77-91; Rich et al. (2000) Current Opinion in Biotechnology 11:54-61; Fivash et al. (1998) Current Opinion in Biotechnology 9:97-101; and U.S. Pat. Nos. 6,373,577; 6,289,286; 5,322,798; 5,341,215; and 6,268,125. The data is used to plot binding curves and determine rate constants, for example, $K_{on}$, $K_{off}$, and the apparent equilibrium binding constant $K_d$, for example as described in, e.g., Myszka (1997) Current Opinion in Biotechnology 8:50-57; O'Shannessy et al. (1996) Analytical Biochemistry 236:275-283; Morton et al. (1995) Analytical Biochemistry 227:176-185; Fisher et al. (1994) Current Opinion in Biotechnology 5:389-95; O'Shannessy (1994) Current Opinion in Biotechnology 5:65-71; and Chaiken et al. (1992) Analytical Biochemistry 201:197-210. In preferred embodiments, the kinetic parameters determined using an SPR analysis may be used as a predictive measure of how a molecule will function in a functional assay, e.g., ADCC.

Characterization of binding to FcγR by molecules comprising an Fc domain (or portion thereof) and/or comprising epitope binding domain specific for an FcγR may be performed according to the methods described in the Antibody Engineering Technology Art. Assays for effector cell functions are well-known, for example as described in Abdul-Majid et al. (2002) Scand. J. Immunol. 55:70-81; Perussia et al. (2000) Methods Mol. Biol. 121:179-192; Lehmann et al. (2000) J. Immunol. Methods 243(1-2):229-242; Ding et al. (1998) Immunity 8:403-411; Baggiolini et al. (1998) Experientia 44(10):841-848; Brown (1994) Methods Cell Biol. 45:147-164; and Munn et al. (1990) J. Exp. Med. 172:231-237.

For example, assays for FcγR-mediated phagocytosis may be conducted using human monocytes, by measuring the ability of THP-1 cells to phagocytose fluoresceinated IgG-opsonized sheep red blood cells (SRBC) by methods previously described in Tridandapani et al. (2000) J. Biol. Chem. 275:20480-20487, or using an antibody-dependent opsonophagocytosis assay (ADCP) as described by Bedzyk et al. (1989) J. Biol. Chem. 264(3):1565-1569. Standard methods known to those skilled in the art may be used to characterize the binding of C1q and mediation of complement dependent cytotoxicity (CDC) by molecules of the invention comprising Fc domains (or portions thereof). For example, to determine C1q binding, a C1q binding ELISA may be performed, and to assess complement activation, a complement dependent cytotoxicity (CDC) assay may be performed, e.g., as described in Gazzano-Santoro et al. (1996) J. Immunol. Methods 202:163.

In another embodiment, the molecules of the invention can be assayed for FcγR-mediated ADCC activity in effector cells, e.g., natural killer cells, using any of the standard methods known to those skilled in the art and described in, e.g., Weng et al. (2003) J. Clin. Oncol. 21:3940-3947; Perussia et al. (2000) Methods Mol. Biol. 121:179-192; Ding et al. (1998) Immunity 8:403-411. In a specific preferred embodiment, a time resolved fluorimetric assay is used for measuring ADCC activity against fluorescently-labeled target cells, as described in, e.g., Blomberg et al. (1996) Journal of Immunological Methods 193:199-206. Target cells used in the ADCC assays of the invention include, but are not limited to, breast cancer cell lines, e.g., SK-BR-3 with ATCC accession number HTB-30 (Tremp et al. (1976) Cancer Res. 33-41); B-lymphocytes; cells derived from Burkitts lymphoma, e.g., Raji cells with ATCC accession number CCL-86 (Epstein et al. (1965) J. Natl. Cancer Inst. 34:231-240), and Daudi cells with ATCC accession number CCL-213 (Klein et al. (1968) Cancer Res. 28:1300-1310). The target cells must be recognized by the antigen binding site of the molecule to be assayed. Preferably, the effector cells used in the ADCC assays of the invention are peripheral blood mononuclear cells (PBMC) that are preferably purified from normal human blood, using standard methods known to one skilled in the art, e.g., using Ficoll-Paque density gradient centrifugation.

C. Methods of Treatment & Pharmaceutical Compositions

The administration of the compositions (e.g., antibodies and polypeptides) of the present invention may be for a "prophylactic" or "therapeutic" purpose, or alternatively can be used for diagnostic purposes. The compositions of the present invention are said to be administered for a "therapeutic" purpose if the amount administered is physiologically significant to provide a therapy for an actual manifestation of the disease. When provided therapeutically, the compound is preferably provided at (or shortly after) the identification of a symptom of actual disease. The therapeutic administration of the compound serves to attenuate the severity of such disease or to reverse its progress. The compositions of the present invention are said to be administered for a "prophylactic" purpose if the amount administered is physiologically significant to provide a therapy for a potential disease or condition. When provided prophylactically, the compound is preferably provided in advance of any symptom thereof. The prophylactic administration of the compound serves to prevent or attenuate any subsequent advance or recurrence of the disease.

Providing a therapy or "treating" refers to any indicia of success in the treatment or amelioration of an injury, pathology or condition, including any objective or subjective parameter such as abatement, remission, diminishing of symptoms or making the injury, pathology or condition more tolerable to the patient, slowing in the rate of degeneration or decline, making the final point of degeneration less debilitating, or improving a patient's physical or mental well-being. The treatment or amelioration of symptoms can be based on objective or subjective parameters, including the results of a physical examination, neuropsychiatric exams, and/or a psychiatric evaluation.

Preferred subjects for treatment include animals, most preferably mammalian species such as humans or other primates, and domestic animals such as dogs, cats and the like, subject to disease and other pathological conditions. A "patient" refers to a subject, preferably mammalian (including human).

Certain embodiments of the present invention relate to pharmaceutical compositions comprising one or more therapeutic agents, and methods of administering a therapeutically effective amount of one or more therapeutic agents, which are capable of prophylactic and/or therapeutic treatment of disorders. The term "therapeutic agent" refers to any agent having a therapeutic effect to prophylactically or therapeutically treat a disorder. Exemplary therapeutic agents include the antibodies and polypeptides of the present invention, as well as other therapeutic agents that may be administered in combination with, or conjugated to, an antibody or polypeptide. In a preferred embodiment, the therapeutic agent is an antibody of the present invention, and preferably is an antibody fragment, a diabody, an Ig-like DART, or a fusion protein.

The molecules of the invention are particularly useful for the treatment and/or prevention of a disease, disorder or infection where an effector cell function (e.g., ADCC) mediated by FcγR is desired (e.g., cancer, infectious disease). For example, molecules of the invention may bind a cell surface antigen and an FcγR (e.g., FcγRIIIA) on an immune effector cell (e.g., NK cell), stimulating an effector function (e.g., ADCC, CDC, phagocytosis, opsonization, etc.) against said cell. In some embodiments, the antibodies and polypeptides of the invention are especially suited for the treatment of cancers. The efficacy of standard monoclonal antibody therapy depends on the FcγR polymorphism of the subject. Carton et al. (2002) Blood 99:754-758; Weng et al. (2003) J Clin Oncol. 21(21):3940-3947. These receptors are expressed on the surface of the effector cells and mediate ADCC. High affinity alleles improve the effector cells' ability to mediate ADCC. The antibodies and polypeptides of the invention may comprise a variant Fc domain that exhibits enhanced affinity to FcγR (relative to a wild type Fc domain) on effector cells, thus providing better immunotherapy reagents for patients regardless of their FcγR polymorphism.

For diagnostic purposes, the antibodies or polypeptides may be coupled to a detectable substance, so that they can be used, for example, to monitor the development or progression of a disease, disorder or infection. Examples of detectable substances include various enzymes (e.g., horseradish peroxidase, beta-galactosidase, etc.), prosthetic groups (e.g., avidin/biotin), fluorescent materials (e.g., umbelliferone, fluorescein, or phycoerythrin), luminescent materials (e.g., luminol), bioluminescent materials (e.g., luciferase or aequorin), radioactive materials (e.g., carbon-14, manganese-54, strontium-85 or zinc-65), positron emitting metals, and nonradioactive paramagnetic metal ions. The detectable substance may be coupled or conjugated either directly to the molecules of the invention or indirectly through an intermediate (e.g., a linker), using techniques known in the art.

C1. Treatable Disorders

Exemplary disorders that may be treated by various embodiments of the present invention include, but are not limited to, proliferative disorders, cell proliferative disorders, and cancer, autoimmune diseases, inflammatory disorders, and infectious diseases. In various embodiments, the invention encompasses methods and compositions for treatment, prevention or management of a disease or disorder in a subject, comprising administering to the subject a therapeutically effective amount of one or more molecules (antibodies or polypeptides) which bind to a disease antigen. For example, molecules of the invention are particularly useful for the prevention, inhibition, reduction of growth or regression of primary tumors, metastasis of cancer cells, and infectious diseases. Although not intending to be bound by a particular mechanism of action, molecules of the invention mediate effector function resulting in tumor clearance, tumor reduction or a combination thereof. In alternate embodiments, diabodies of the invention mediate therapeutic activity by cross-linking of cell surface antigens and/or receptors and enhanced apoptosis or negative growth regulatory signaling.

Antibodies with a decreased affinity for FcγRIIB and an increased affinity for FcγRIIIA and/or FcγRIIA may lead to an enhanced activating response upon FcγR binding and thus have therapeutic efficacy for treating and/or preventing cancer. Non-limiting examples of cancers treatable by the methods herein include acute myeloid lymphoma, adrenal carcinoma, adenocarcinoma, basal cancer, bladder cancer, bone cancer, bone and connective tissue sarcoma, brain cancer, breast cancer, bronchial cancer, cervical cancer, choriocarcinoma, chronic lymphocytic leukemia, chronic myelogenous leukemia, colon cancer, colorectal cancer, endometrial cancer, esophageal cancer, eye cancer, fallopian tube cancer, gall bladder cancer, gastrointestinal cancer, glioma, hairy cell leukemia, hepatoma, Hodgkin's disease, intrahepatic bile duct cancer, joint cancer, Kaposi's sarcoma, kidney cancer, larynx cancer, liver cancer, leukemia, lung cancer, lymphoblastic leukemia, lymphoma, malignant mesothelioma, medullobastoma, melanoma, mesothelioma, middle ear cancer, multiple myeloma, myeloma, myxosarcoma, nasal cavity cancer, nasopharynx cancer, neuroblastoma, Non-Hodgkin's lymphoma, non-small cell lung cancer, nose cancer, oral cavity cancer, ovarian cancer, pancreatic cancer, penal cancer, peritoneum cancer, pharynx cancer, pituitary gland cancer, prostate cancer, rectal cancer, renal cancer, salivary gland cancer, skin cancer, soft tissue sarcoma, squamous cell carcinoma, stomach cancer, testicular cancer, thyroid cancer, urinary cancer, uterine cancer, vaginal cancer, vesticular cancer, vulval cancer, and Wilm's tumor.

In some embodiments, the cancer is a hematopoietic cancer or blood-related cancer, such as lymphoma, leukemia, myeloma, lymphoid malignancy, cancer of the spleen, and cancer of the lymph nodes. In a preferred embodiment, the cancer is a B-cell associated cancer, such as, for example, high, intermediate or low grade lymphoma (including B cell lymphoma such as, for example, Burkitt's lymphoma, diffuse large cell lymphoma, follicular lymphoma, Hodgkin's lymphoma, mantle cell lymphoma, marginal zone lymphoma, mucosa-associated-lymphoid tissue B cell lymphoma, non-Hodgkin's lymphoma, small lymphocytic lymphoma, and T cell lymphomas) and leukemias (including chronic lymphocytic leukemia, such as B cell leukemia (CD5+B lymphocytes), chronic myeloid leukemia, lymphoid leukemia, such as acute lymphoblastic leukemia, myelodysplasia, myeloid leukemia, such as acute myeloid leukemia, and secondary leukemia), multiple myeloma, such as plasma cell malignancy, and other hematological and/or B cell- or T-cell-associated cancers. Other exemplary cancers are cancers of additional hematopoietic cells, including polymorphonuclear leukocytes, such as basophils, eosinophils, neutrophils and monocytes, dendritic cells, platelets, erythrocytes and natural killer cells.

In some embodiments, the cancer to be treated is breast cancer, prostate cancer, uterine cancer, ovarian cancer, colon cancer, endometrial cancer, adrenal carcinoma, or non-small cell lung cancer. In some embodiments, the cancer is breast cancer or prostate cancer. In some embodiments, the cancer is a cancer in which HER2/neu is overexpressed. In a specific embodiment, an antibody or polypeptide of the invention inhibits or reduces the growth of cancer cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth of cancer cells in the absence of the antibody or polypeptide of the invention.

Antibodies with an increased affinity for FcγRIIB and a decreased affinity for FcγRIIIA and/or FcγRIIA may lead to a diminished activating response upon FcγR binding and thus have therapeutic efficacy for treating and/or preventing inflammation and autoimmune disease. Examples of autoimmune disorders that may be treated by the methods herein include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erythematosus, Meniere's disease, mixed connective tissue disease, multiple sclerosis, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiff-man syndrome, systemic lupus erythematosus, takayasu arteritis, temporal arteristis/giant cell arteritis, type 1 or immune-mediated diabetes mellitus, ulcerative colitis, uveitis, vasculitides such as dermatitis herpetiformis vasculitis, vitiligo, and Wegener's granulomatosis.

Non-limiting examples of inflammatory disorders treatable by the methods herein include immune-mediated inflammatory disorders (IMIDs), which are inflammatory conditions caused and sustained by an antigen-specific, pathological immune response. Among these disorders are various types of allergic diseases, such as asthma, hay fever, and urticaria, arthritis, such as osteoarthritis and rheumatoid arthritis, chronic inflammation, chronic obstructive pulmonary disease (COPD), connective tissue disorders, fibrosis, graft rejection and graft-versus host-disease, inflammatory bowel disease (e.g., Crohn's disease and ulcerative colitis), inflammatory osteolysis, insulin-dependent diabetes, pulmonary fibrosis, retinitis, undifferentiated arthropathy, undifferentitated spondyloarthropathy, and uveitis. Molecules of the invention comprising at least one epitope binding domain specific for FcγRIIB and/or a variant Fc domain with an enhanced affinity for FcγRIIB and a decreased affinity for FcγRIIIA can also be used to prevent the rejection of transplants.

The anti-inflammatory polypeptides of the present invention will preferably reduce inflammation in an animal by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the inflammation in an animal that does not receive such polypeptides.

In certain embodiments, the polypeptides of the invention are toxic to an infectious agent, enhance immune response against said agent or enhance effector function against said agent, relative to the immune response in the absence of said molecule. Infectious diseases that can be treated or prevented by the molecules of the invention are caused by infectious agents including but not limited to bacteria, fungi, protozoans, and viruses. Non-limiting exemplary bacterial diseases include those caused by *Bacillus antracis* (anthrax), *Borrelia burgdorferi* (Lyme disease), *Candida, chlamydia*, cholera, diptheria, *E. coli, Enterococcus faecials, Heliobacter pylori, Klebsiella pneumoniae, legionella, mycobacterium, mycoplasma, Neisseria*, pertussis, plague, *Proteus vulgaris, Pseudomonas aeruginosa, S. pneumonia, Salmonella, staphylococcus, streptococcus*, and tetanus. Non-limiting protozoal diseases include those caused by kokzidioa, *leishmania*, malaria, or *trypanosoma*.

Non-limiting examples of viral diseases include those caused by adenovirus, arbovirus, coronavirus, coxsackie virus, cytomegalovirus, ebola, echinovirus, echovirus, endotoxin (LPS), enterovirus, Epstein Barr virus, hepatitis virus (e.g., hepatitis type A, hepatitis type B, hepatitis type C, murine hepatitis), herpes virus (e.g., herpes simplex type I (HSV-I), herpes simplex type II (HSV-II), murine gamma herpes virus), human immunodeficiency virus type I (HIV-I), human immunodeficiency virus type II (HIV-II), huntavirus, influenza, leukemia virus (e.g., murine leukemia, feline leukemia, etc.); measles virus, mumps virus, papilloma virus, papova virus, polio virus, respiratory syncytial virus, retrovirus, rhinovirus, rinderpest, rotavirus, rubella virus, small pox, T-cell lymphotropic virus 1, vaccinia, varicella, and agents of viral diseases such as viral meningitis, encephalitis, or dengue.

C2. Formulations

The pharmaceutical compositions can be formulated according to known methods for preparing pharmaceutically useful compositions, and may include a pharmaceutically acceptable carrier and/or an excipient. The compositions can be in any suitable form, for example tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders, to name just a few non-limiting alternatives. Such compositions may be prepared by any known method, for example by admixing the active ingredient with the carrier(s) or excipient(s) under sterile conditions.

The active ingredients can also be formulated so as to provide quick, sustained or delayed release of the active ingredient after administration to the patient by employing procedures known in the art. The physical and chemical characteristics of the compositions of the invention may be modified or optimized according to the skill in the art, depending on the mode of administration and the particular disease or disorder to be treated. The compositions may be provided in unit dosage form, a sealed container, or as part of a kit, which may include instructions for use and/or a plurality of unit dosage forms.

In particular embodiments, the therapeutic agents can be incorporated into a composition, by, e.g., encapsulation in liposomes, microparticles, microcapsules, recombinant cells capable of expressing the antibody or fusion protein, receptor-mediated endocytosis (See, e.g., Wu and Wu (1987) J. Biol. Chem. 262:4429-4432), construction of a nucleic acid as part of a retroviral or other vector, etc. In another particular embodiment, the therapeutic agents are supplied as a dry sterilized lyophilized powder or water free concentrate in a hermetically sealed container and can be reconstituted, e.g., with water or saline to the appropriate concentration for administration to a subject.

Preferably, the therapeutic agent is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. The lyophilized powder should be stored at between 2 and 8° C. in its original container and the molecules should be parenterally administered within 12 hours, preferably within 6 hours, within 5 hours, within 3 hours, or within 1 hour after being reconstituted. In an alternative embodiment, the therapeutic agents are supplied in liquid form in a hermetically sealed container indicating the quantity and concentration of the therapeutic agent. Preferably, the liquid form is supplied in a hermetically sealed container at least 1 mg/ml, more preferably at least 2.5 mg/ml, at least 5 mg/ml, at least 8 mg/ml, at least 10 mg/ml, at least 15 mg/ml, at least 25 mg/ml, at least 50 mg/ml, at least 100 mg/ml, at least 150 mg/ml, at least 200 mg/ml of the molecules.

C3. Kits

The compositions may also be included in a kit. The kit can include, in non-limiting aspects, a pharmaceutical composition comprising a therapeutic agent, instructions for administration and/or other components. In preferred embodiments, the kit can include a composition ready for administration. Containers of the kits can include a bottle, dispenser, package, compartment, or other types of containers, into which a component may be placed. The container can include indicia on its surface. The indicia, for example, can be a word, a phrase, an abbreviation, a picture, or a symbol. The containers can dispense a pre-determined amount of the component (e.g. compositions of the present invention). The composition can be dispensed in a spray, an aerosol, or in a liquid form or semi-solid form. The containers can have spray, pump, or squeeze mechanisms. In certain aspects, the kit can include a syringe for administering the compositions of the present invention.

Where there is more than one component in the kit (they may be packaged together), the kit also will generally contain a second, third or other additional containers into which the additional components may be separately placed.

The kits of the present invention also can include a container housing the components in close confinement for commercial sale. Such containers may include injection or blow-molded plastic containers into which the desired bottles, dispensers, or packages are retained. A kit can also include instructions for employing the kit components as well the use of any other compositions, compounds, agents, active ingredients, or objects not included in the kit. Instructions may include variations that can be implemented. The instructions can include an explanation of how to apply, use, and maintain the products or compositions, for example.

C4. Administration and Dosage

A variety of administration routes for the compositions of the present invention are available. The particular mode selected will depend, of course, upon the particular therapeutic agent selected, whether the administration is for prevention, diagnosis, or treatment of disease, the severity of the medical disorder being treated and dosage required for therapeutic efficacy. The methods of this invention may be practiced using any mode of administration that is medically acceptable, and produces effective levels of the active compounds without causing clinically unacceptable adverse effects. Such modes of administration include, but are not limited to, oral, buccal, sublingual, inhalation, mucosal, rectal, intranasal, topical, ocular, periocular, intraocular, transdermal, subcutaneous, intra-arterial, intravenous, intramuscular, parenteral, or infusion methodologies. In a specific embodiment, it may be desirable to administer the pharmaceutical compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers.

As used herein, the term "therapeutically effective amount" means the total amount of each active component of the pharmaceutical composition or method that is sufficient to show a meaningful patient benefit, i.e., healing or amelioration of chronic conditions, a reduction in symptoms, an increase in rate of healing of such conditions, or a detectable change in the levels of a substance in the treated or surrounding tissue. When applied to an individual active ingredient, administered alone, the term refers to that ingredient alone. When applied to a combination, the term refers to combined amounts of the active ingredients that result in the therapeutic effect, whether administered in combination, serially, or simultaneously.

The dosage schedule and amounts effective for therapeutic and prophylactic uses, i.e., the "dosing regimen", will depend upon a variety of factors, including the stage of the disease or condition, the severity of the disease or condition, the general state of the patient's health, the patient's physical status, age and the like. Therapeutic efficacy and toxicity of the compositions may be determined by standard pharmaceutical, pharmacological, and toxicological procedures in cell cultures or experimental animals. For example, numerous methods of determining $ED_{50}$ (the dose therapeutically effective in 50 percent of the population) and $LD_{50}$ (the dose lethal of 50 percent of the population) exist. The dose ratio between therapeutic and toxic effects is the therapeutic index, and it can be expressed as the ratio $ED_{50}/LD_{50}$. Compositions exhibiting high therapeutic indices are preferred. The data obtained from cell culture assays or animal studies may be used in formulating a range of dosages for human use. The dosage is preferably within a range of concentrations that includes the $ED_{50}$ with little or no toxicity, and may vary within this range depending on the dosage form employed, sensitivity of the patient, and the route of administration.

The dosage regimen also takes into consideration pharmacokinetics parameters well known in the art, i.e., the rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington, supra). The state of the art allows the clinician to determine the dosage regimen for each individual patient, therapeutic agent and disease or condition treated. Single or multiple administrations of the compositions of the present invention can be administered depending on the dosage and frequency as required and tolerated by the patient. The duration of prophylactic and therapeutic treatment will vary depending on the particular disease or condition being treated. Some diseases lend themselves to acute treatment whereas others require long-term therapy. If administration is not on a daily basis, for example if injections are given every few days, every few weeks, or every few months, then more therapeutic agent may be included in each administration, so that daily release of the agent is adequate to meet therapeutic needs.

In a preferred embodiment, the therapeutic agents of the invention are administered in metronomic dosing regimens, either by continuous infusion or frequent administration without extended rest periods. Such metronomic administration can involve dosing at constant intervals without rest periods. Typically the therapeutic agents, in particular cytotoxic agents, are used at lower doses. Such dosing regimens encompass the chronic daily administration of relatively low doses for extended periods of time, which can minimize toxic side effects and eliminate rest periods. Kamat et al. (2007) Cancer Research 67:281-88. In certain embodiments, the therapeutic agents are delivered by chronic low-dose or continuous infusion ranging from about 24 hours to about 2 days, to about 1 week, to about 2 weeks, to about 3 weeks to about 1 month to about 2 months, to about 3 months, to about 4 months, to about 5 months, to about 6 months. The scheduling of such dose regimens can be optimized by the skilled oncologist.

For antibodies encompassed by the invention, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. The dosage and frequency of administration may be reduced or altered by enhancing uptake and tissue penetration of the antibodies by modifications such as, for example, lipidation. In one embodiment, the dosage of the antibodies administered to a patient are 0.01 mg to 1000 mg/day, when used as single agent therapy. In another embodiment the antibodies are used in combination with other therapeutic compositions and the dosage administered to a patient are lower than when said molecules are used as a single agent therapy. In a preferred example, a subject is treated with antibodies in the range of between about 0.1 to 30 mg/kg body weight, one time per week for between about 1 to 10 weeks, preferably between 2 to 8 weeks, more preferably between about 3 to 7 weeks, and even more preferably for about 4, 5, or 6 weeks.

C5. Combination Therapies

The invention further encompasses administering the antibodies or polypeptides of the invention in combination with other therapies known to those skilled in the art for the treatment or prevention of cancer, autoimmune disease, inflammation, or infectious disease, including but not limited to, current standard and experimental chemotherapies, hormonal therapies, biological therapies, immunotherapies, radiation therapies, or surgery. In some embodiments, the antibodies or polypeptides of the invention may be administered in combination with a therapeutically or prophylactically effective amount of one or more therapeutic agents known to those skilled in the art for the treatment and/or prevention of cancer, autoimmune disease, infectious disease or intoxication.

As used herein, the term "combination" refers to the use of more than one therapeutic agent. The use of the term "combination" does not restrict the order in which therapeutic agents are administered to a subject with a disorder, nor does it mean that the agents are administered at exactly the same time, but rather it is meant that an antibody or polypeptide of the invention and the other agent are administered to a mammal in a sequence and within a time interval such that the antibody or polypeptide of the invention can act together with the other agent to provide an increased benefit than if they were administered otherwise. For example, each therapeutic agent (e.g., chemotherapy, radiation therapy, hormonal therapy or biological therapy) may be administered at the same time or sequentially in any order at different points in time; however, if not administered at the same time, they should be administered sufficiently close in time so as to provide the desired therapeutic or prophylactic effect. Each therapeutic agent can be administered separately, in any appropriate form and by any suitable route, e.g., one by the oral route and one parenterally.

In various embodiments, a first therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second (or subsequent) therapeutic agent to a subject with a disorder. In preferred embodiments, two or more agents are administered within the same patient visit, or no more than 12 hours apart, no more than 24 hours apart, or no more than 48 hours apart.

In certain embodiments, the therapeutic agents are cyclically administered to a subject. Cycling therapy involves the administration of a first agent for a period of time, followed by the administration of a second agent and/or third agent for a period of time and repeating this sequential administration. Cycling therapy can reduce the development of resistance to one or more of the therapies, avoid or reduce the side effects of one of the therapies, and/or improves the efficacy of the treatment. Exemplary cycles are about once every week, about once every 10 days, about once every two weeks, and about once every three weeks. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In an embodiment for the treatment of a cell proliferative disorder, an antibody or polypeptide of the present invention is conjugated to, or administered in combination with, another therapeutic agent, such as, but not limited to, an alkylating agent (e.g., mechlorethamine or cisplatin), angiogenesis inhibitor, anthracycline (e.g., daunorubicin/daunomycin or doxorubicin), antibiotic (e.g., dactinomycin, bleomycin, or anthramycin), antibody (e.g., an anti-VEGF antibody such as bevacizumab (sold as AVASTIN® by Genentech, Inc.), an anti-EGFR antibody such as panitumumab (sold as VECTIBIX™ by Amgen, Inc.), or an anti-integrin antibody such as natalizumab (sold as TYSABRI® by Biogen Idec and Elan Pharmaceuticals, Inc.)), an antimetabolite (e.g., methotrexate or 5-fluorouracil), an antimitotic agent (e.g., vincristine or paclitaxel), a cytotoxin (e.g., a cytostatic or cytocidal agent), a hormone therapy agent (e.g., a selective estrogen receptor modulator (e.g., tamoxifen or raloxifene), aromatase inhibitor, luteinizing hormone-releasing hormone analogue, progestational agent, adrenocorticosteroid, estrogen, androgen, anti-estrogen agent, androgen receptor blocking agent, 5-alpha reductase inhibitor, adrenal production inhibitor, etc.), a matrix metalloprotease inhibitor, a radioactive element (e.g., alpha-emitters, gamma-emitters, etc.), or any other chemotherapeutic agent.

Non-limiting examples of suitable angiogenesis inhibitors include ABT-627; angiostatin (plasminogen fragment); angiozyme; antiangiogenic antithrombin III; Bay 12-9566; benefin; bevacizumab; BMS-275291; bisphosphonates; cartilage-derived inhibitor (CDI); CAI; CD59 complement fragment; CEP-7055; Col 3; combretastatin A-4; endostatin (collagen XVIII fragment); farnesyl transferase inhibitors (FTI); fibronectin fragment; gro-beta; halofuginone; heparinases; heparin hexasaccharide fragment; HMV833; human chorionic gonadotropin (hCG); IM-862; interferon alpha/beta/gamma; interferon inducible protein (IP-10); interleukin-12; kringle 5 (plasminogen fragment); marimastat; metalloproteinase inhibitors (TIMPs); 2-methoxyestradiol; MMI 270 (CGS 27023A); MoAb IMC-1C11; neovastat; NM-3; panzem; PI-88; placental ribonuclease inhibitor; plasminogen activator inhibitor; platelet factor-4 (PF4); prinomastat; prolactin 16 kDa fragment; proliferin-related protein (PRP); PTK 787/ZK 222594; retinoids; solimastat; squalamine; SS 3304; SU 5416; SU6668; SU11248; tetrahydrocortisol-S; tetrathiomolybdate; thalidomide; thrombospondin-1 (TSP-1); TNP-470; transforming growth factor-beta (TGF-b); vasculostatin; vasostatin (calreticulin fragment); ZD6126; and ZD 6474.

Non-limiting examples of additional antibodies for the treatment of a cell proliferative disorder include antibodies to 17-1A, $\alpha v \beta_3$, AFP, CD3, CD18, CD20, CD22, CD33, CD44, CD52, CEA, CTLA-4, DNA-associated proteins, EGF receptor, Ep-CAM, GD2-ganglioside, gp IIIb/IIIa, gp72, HER2, HLA-DR 10 beta, HLA-DR antigen, IgE, ganglioside GD3, MUC-1, nuC242, PEM antigen, SK-1 antigen, tumor antigen CA125, tumor antigen MUC1, VEGF, and VEGF-receptor.

In a different embodiment, an antibody or polypeptide of the present invention may be administered in combination with a therapeutic agent or agents for the treatment of an inflammatory disorder, such as, but not limited to, antibodies, anticholinergic agents, beta-agonists, methyl xanthines, non-steroidal anti-inflammatory drugs (NSAIDs) (e.g., aspirin, ibuprofen, celecoxib or diclofenac), and steroidal anti-inflammatory drugs (e.g., glucocorticoids, dexamethasone, cortisones, prednisone or eicosanoids). The additional antibodies may be any suitable antibody for the treatment of inflammatory disease, such as, but not limited to antibodies to alpha4beta7, beta2-integrin, CBL, CD2, CD3, CD4, CD11a, CD11/18, CD14, CD18, CD23, CD25, CD40L, CD64 (FcR), CD80, CD147, Complement (C5), E-selectin, Fact VII, gpIIbIIIa, ICAM-3, IgE, IL-4, IL-5, IL-8, TNF-alpha, and VLA-4.

In a further embodiment, an antibody or polypeptide of the present invention may be administered in combination with a therapeutic agent or agents for the treatment of an autoimmune disorder, such as, but not limited to, antibodies, brequinar, cyclophosphamide, cyclosporine A, cytokine receptor modulators, deoxyspergualin, leflunomide, macrolide antibiotics, malononitriloamindes (e.g., leflunamide), methothrexate, methylprednisolone, mizoribine, mycophenolate mofetil, rapamycin (sirolimus), steroids, and T cell receptor modulators. The additional antibodies may be any suitable antibody for the treatment of an autoimmune disorder, and non-limiting examples include antibodies to a4b7 integrin receptor, CBL antigen, CD2, CD4, CD23, CD40, CD80, FcRI, Gamma Interferon, IL-8, inosine monophosphate dehydrogenase, ICE interleukin-1 beta, P38MAP kinase, and TNF.

In still another embodiment, an antibody or polypeptide of the present invention may be administered in combination with a therapeutic agent or agents for the treatment of an infectious disease, such as, but not limited to, an antibiotic, anti-fungal, or anti-viral agent. Antibiotics that can be used in combination with the molecules of the invention include, but are not limited to, 2,4 diaminopyrimidines (e.g., brodimoprim), aminoglycosides (e.g., apramycin, neomycin, or spectinomycin), amphenicols (e.g., chloramphenicol), amphomycins, ansamycins (e.g., rifamide and rifampin), bacitracins, carbacephems (e.g., loracarbef), carbapenems (e.g., biapenem and imipenem), cephalosporins (e.g., cephalexin or cefadroxil), cephamycins (e.g., cefbuperazone, cefmetazole, and cefminox), clarithromycins, erythromycins, lincosamides (e.g., clindamycin and lincomycin), macrolides (e.g., tobramycin), monobactams (e.g., carumonam), nitrofurans (e.g., furaltadone, and furazolium chloride), oxacephems (e.g., flomoxef and moxalactam), penicillins, quinolones (e.g., ofloxacin or ciprofloxacin), sulfonamides (e.g., benzylsulfamide, and sulfacytine), sulfones (e.g., diathymosulfone, glucosulfone sodium, and solasulfone), and tetracyclines (e.g., apicycline and chlortetracycline).

Antifungal agents that can be used in combination with the molecules of the invention include, but are not limited to, amphotericin B, butoconazole, ciclopirox, clotrimazole, econazole, fluconazole, flucytosine, griseofuldin, haloprogrin, intrathecal, itraconazole, ketoconazole, miconazole, naftifine, nystatin, terbinafine, terconazole, tioconazole, and undecylenate. Useful anti-viral agents that can be used in combination with the molecules of the invention include, but are not limited to, non-nucleoside reverse transcriptase inhibitors, nucleoside analogs, nucleoside reverse transcriptase inhibitors, and protease inhibitors. Non-limiting examples of such agents are acyclovir, adefovir, alpha interferons, amantadine, amprenavir, clevadine, entecavir, foscarnet, gangcyclovir, idoxuridine, indinavir, lopinavir, pleconaril, ribavirin, rimantadine, ritonavir, saquinavir, trifluridine, vidarabine, and zidovudine.

C6. Demonstration of Therapeutic Utility

The pharmaceutical compositions, prophylactic, or therapeutic agents of the invention are preferably tested in vitro, in a cell culture system, and in an animal model organism, such as a rodent animal model system, for the desired therapeutic activity prior to use in humans. For example, assays which can be used to determine whether administration of a specific pharmaceutical composition is desired, include cell culture assays in which a patient tissue sample is grown in culture, and exposed to or otherwise contacted with a pharmaceutical composition of the invention, and the effect of such composition upon the tissue sample is observed. The tissue sample can be obtained by biopsy from the patient. This test allows the identification of the therapeutically most effective prophylactic or therapeutic molecule(s) for each individual patient. In various specific embodiments, in vitro assays can be carried out with representative cells of cell types involved in an autoimmune or inflammatory disorder (e.g., T cells), to determine if a pharmaceutical composition of the invention has a desired effect upon such cell types.

Suitable animal model systems include, but are not limited to, rats, mice, chicken, cows, monkeys, pigs, dogs, rabbits, etc. Any animal system well-known in the art may be used. In a specific embodiment of the invention, combinations of prophylactic and/or therapeutic agents are tested in a mouse model system. Preferred animal models for use in the methods of the invention are, for example, transgenic mice expressing human FcγRs on mouse effector cells, e.g., any mouse model described in U.S. Pat. No. 5,877,396 can be used in the present invention.

Anti inflammatory activity can be determined by using various experimental and spontaneous animal models of inflammatory arthritis known in the art and described in Crofford L. J. and Wilder R. L., "Arthritis and Autoimmunity in Animals", in Arthritis and Allied Conditions: A Textbook of Rheumatology, McCarty et al. (eds.), Chapter 30 (Lee and Febiger, 1993). For example, adjuvant-induced arthritis models such as carrageenan-, xymosan-, or collagen-induced arthritis in rats, hamsters, rabbits, dogs and pigs, are useful in studying anti-inflammatory activity, and inhibition of carrageenan-induced paw edema in rats is a primary in vivo screen for the anti inflammatory activity of most NSAIDs, and is considered predictive of human efficacy. These models are described in, e.g., Winter et al. (1962) Proc. Soc. Exp. Biol Med. 111:544-47; and Hansra et al. (2000) Inflammation 24(2):141-55. Animal models for inflammatory bowel disease can also be used to assess the efficacy of therapies of the invention, for example the models described in, e.g., Strober (1985) Dig. Dis. Sci. 30(12 Suppl):3S-10S; Kim et al. (1992) Scand. J. Gastroentrol. 27:529-37). In these models, ulcerative cholitis and Crohn's disease can be induced in animals by oral administration of sulfated polysaccharides, dextran sulfate or chemical irritants.

Efficacy in treating autoimmune disorders may be assessed using animal models for autoimmune disorders such as type 1 diabetes, thyroid autoimmunity, systemic lupus eruthematosus, and glomerulonephritis, for example the models described in Flanders et al. (1999) Autoimmunity 29:235-46; Krogh et al. (1999) Biochimie 81:511-15; Foster (1999) Semin. Nephrol. 19:12-24, etc.

The anti-cancer activity of the therapeutic agents also can be determined by using various experimental animal models for the study of cancer such as the SCID mouse model, transgenic mice or nude mice with human xenografts, and other animal models such as hamsters, rabbits, etc. known in the art and described in Relevance of Tumor Models for Anticancer Drug Development (1999, eds. Fiebig and Burger); Contributions to Oncology (1999, Karger); The Nude Mouse in Oncology Research (1991, eds. Boven and Winograd); and Anticancer Drug Development Guide (1997 ed. Teicher). Preferred animal models are mouse xenograft models. Tumor cell lines that can be used as a source for xenograft tumors include but are not limited to, SKBR3 and MCF7 cells, which can be derived from patients with breast adenocarcinoma. These cells have both erbB2 and prolactin receptors. SKBR3 cells have been used routinely in the art as ADCC and xenograft tumor models. Alternatively, OVCAR3 cells derived from a human ovarian adenocarcinoma can be used as a source for xenograft tumors.

The therapeutic agents of the invention are preferably tested in vitro, and then in vivo, for the desired therapeutic or prophylactic activity, prior to use in humans. Therapeutic agents and methods may be screened using cells of a tumor or malignant cell line. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, decreased growth and/or colony formation in soft agar or tubular network formation in three-dimensional basement membrane or extracellular matrix preparation, etc.

The data obtained from the cell culture assays and animal studies can be used in formulating a range of dosage of the therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

D. Other Methods

D1. Gene Therapy

In a specific embodiment, nucleic acids comprising sequences encoding molecules of the invention, are administered to treat, prevent or ameliorate one or more symptoms associated with a disease, disorder, or infection, by way of gene therapy. Gene therapy refers to therapy performed by the administration to a subject of an expressed or expressible nucleic acid. In this embodiment of the invention, the nucleic acids produce their encoded antibody or fusion protein that mediates a therapeutic or prophylactic effect. Any methods for gene therapy available in the art may be used, for example the methods described in, e.g., Goldspiel et al. (1993) Clinical Pharmacy 12:488-505; Wu and Wu (1991) Biotherapy 3:87-95; Tolstoshev (1993) Ann. Rev. Pharmacol. Toxicol. 32:573-596; Mulligan (1993) Science 260:926-932; and Morgan and Anderson (1993) Ann. Rev. Biochem. 62:191-217.

In a preferred aspect, a composition of the invention comprises nucleic acids encoding an antibody, diabody, or fusion protein of the invention, said nucleic acids being part of an expression vector that expresses the antibody in a suitable host. In particular, such nucleic acids have promoters, preferably heterologous promoters, operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids, as described in Koller and Smithies (1989) Proc. Natl. Acad. Sci. (U.S.A.) 86:8932-35; and Zijlstra et al. (1989) Nature 342:435-38.

Delivery of the nucleic acids into a subject may be either direct, in which case the subject is directly exposed to the nucleic acid or nucleic acid-carrying vectors, or indirect, in which case, cells are first transformed with the nucleic acids in vitro, then transplanted into the subject. These two approaches are known, respectively, as in vivo or ex vivo gene therapy.

In a specific embodiment, a polynucleotide encoding a polypeptide of the present invention is administered in vivo, where it is expressed to produce the encoded polypeptide. This can be accomplished by any of numerous methods, such as by infection using retroviral or other viral vectors (as described in, e.g., U.S. Pat. No. 4,980,286; Miller et al. (1993) Meth. Enzymol. 217:581-599; Salmons and Gunzberg (1993) Human Gene Therapy 4:129-141; Grossman and Wilson (1993) Curr. Opin. in Genetics and Devel. 3:110-114; Kozarsky and Wilson (1993) Current Op. in Genetics and Dev. 3:499-503; Walsh et al. (1993) Proc. Soc. Exp. Biol. Med. 204:289-300; Bout et al. (1994) Human Gene Therapy 5:3-10; Boesen et al. (1994) Biotherapy 6:291-302; Clowes et al. (1994) J. Clin. Invest. 93:644-651; Klein et al. (1994) Blood 83:1467-1473; and U.S. Pat. No. 5,436,146), or by direct injection of naked DNA, or by use of microparticle bombardment (e.g., a gene gun), or coating with lipids or cell-surface receptors or transfecting agents, encapsulation in liposomes, microparticles, or microcapsules, or by administering them in linkage to a peptide which is known to enter the nucleus or in linkage to an antigen subject to receptor-mediated endocytosis (as described in, e.g., Wu and Wu (1987) J. Biol. Chem. 262:4429-4432; Joliot et al. (1991) Proc. Natl. Acad. Sci. (U.S.A.) 88:1864-1868; WO 92/06180; WO 92/22635; WO92/20316; WO93/14188; WO 93/20221) (which can be used to target cell types specifically expressing the receptors), etc.

A nucleic acid may be introduced into a cell prior to administration in vivo of the resulting recombinant cell, for example as described in WO 94/08598; Rheinwald (1980) Meth. Cell Bio. 21A:229; Pittelkow and Scott (1986) Mayo Clinic Proc. 61:771; Stemple and Anderson (1992) Cell 7 1:973-985. The resulting recombinant cells can be delivered to a subject by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art. Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc. In a preferred embodiment, the cell used for gene therapy is autologous to the subject.

D2. Vaccine Therapy

In some embodiments, the antibodies of the invention may be used to induce an immune response against an antigenic or immunogenic agent, including but not limited to cancer antigens and infectious disease antigens. The vaccine compositions of the invention comprise one or more antigenic or immunogenic agents to which an immune response is desired, wherein the one or more antigenic or immunogenic agents is coated with an antibody of the invention. The vaccine compositions of the invention are particularly effective in eliciting an immune response, preferably a protective immune response against the antigenic or immunogenic agent, which may be a virus against which an immune response is desired, or an antigen derived from other viral or non-viral pathogens.

In yet other embodiments, the invention encompasses pathogenic cells or viruses, preferably attenuated viruses, which express the antibody on their surface. The invention further encompasses methods to induce tolerance in a subject by administering a composition of the invention. Preferably a composition suitable for inducing tolerance in a subject, comprises an antigenic or immunogenic agent coated with an antibody of the invention.

D3. Targeting Liposomes or Other Microcarriers and Nanocarriers

In some embodiments, the antibodies of the invention can be used to prepare targeted liposomes for delivery of a desired therapeutic composition (e.g., anti-cancer agents) to a target cell (e.g., a prostate cancer cell or other HER2/neu expressing cell). The preparation and use of immunoliposomes for targeted delivery of antitumor drugs is reviewed in Mastrobattista et al. (1999) Advanced Drug Delivery Reviews 40:103-127. Liposomes are vesicular structures based on lipid bilayers. They can be as small as 20 nm and as large as 10 μm in diameter. They can be unilamellar (only one bilayer surrounds an aqueous core) or multilamellar (two or more bilayers concentrically oriented around an aqueous core). Targeting of liposomes using a variety of targeting agents (e.g., antibodies of the invention) is well known in the art. See, e.g., U.S. Pat. Nos. 4,957,773 and 4,603,044. Standard methods for coupling targeting agents to liposomes can be used. Antibody targeted liposomes can be constructed using, for instance, liposomes which incorporate protein A. See Renneisen et al. (1990) J. Biol. Chem. 265:16337-16342; and Leonetti et al. (1990) Proc. Natl. Acad. Sci. (U.S.A.) 87:2448-2451.

In a preferred embodiment, the liposomes are formed from standard vesicle-forming lipids, which generally include neutral and negatively charged phospholipids and a sterol, such as cholesterol. The selection of lipids is generally guided by consideration of, e.g., liposome size and stability of the liposomes in the bloodstream. A variety of methods are available for preparing liposomes, as described in, e.g., Szoka, et al. (1980) Ann. Rev. Biophys. Bioeng. 9:467; U.S. Pat. Nos. 4,235,871; 4,501,728; and 4,837,028. One method produces multilamellar vesicles of heterogeneous sizes. In this method, the vesicle forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous solution of the targeted drug and the targeting component (antibody) and allowed to hydrate, typically over a 15-60 minute period with agitation. The size distribution of the resulting multilamellar vesicles can be shifted toward smaller sizes by hydrating the lipids under more vigorous agitation conditions or by adding solubilizing detergents such as deoxycholate.

D4. Immunoassays

The antibodies of the invention can be used to detect HER2/neu, or cells expressing HER2/neu. Any of a number of methods may be used to achieve such detection. For example, immunological binding assays may be used (see, e.g., U.S. Pat. Nos. 4,366,241; 4,376,110; 4,517,288; and 4,837,168). For a review of the general immunoassays, see also Asai (ed. 1993) Methods in Cell Biology Vol. 37, Academic Press, New York; Stites & Terr (eds. 1991) Basic and Clinical Immunology 7th Ed.

Thus, the present invention provides methods of detecting cells that express HER2/neu. In one method, a biopsy is performed on the subject and the collected tissue is tested in vitro. The tissue or cells from the tissue is then contacted, with an anti-HER2/neu antibody of the invention. Any immune complexes which result indicate the presence of a HER2/neu protein in the biopsied sample. To facilitate such detection, the antibody can be radiolabeled or coupled to an effector molecule which is a detectable label, such as a radiolabel. In another method, the cells can be detected in vivo using typical imaging systems. Then, the localization of the label is determined by any of the known methods for detecting the label. A conventional method for visualizing diagnostic imaging can be used. For example, paramagnetic isotopes can be used for MRI. Internalization of the antibody may be important to extend the life within the organism beyond that provided by extracellular binding, which will be susceptible to clearance by the extracellular enzymatic environment coupled with circulatory clearance.

HER2/neu proteins can also be detected using standard immunoassay methods and the antibodies of the invention. Standard methods include, for example, radioimmunoassay, immunochromatographic methods, sandwich immunoassays (including ELISA), immunofluorescence assays, Western blot, affinity chromatography (affinity ligand bound to a solid phase), and in situ detection with labeled antibodies.

Having now generally described the invention, the same will be more readily understood through reference to the following examples, which are provided by way of illustration and are not intended to be limiting of the present invention unless specified.

Example 1

BIACore Affinity Determinations

The kinetic parameters of the binding of eluted and purified antibodies were analyzed using a BIAcore assay (BIAcore instrument 1000, BIAcore Inc., Piscataway, N.J.) and associated software. HER-2 was immobilized on one of the four flow cells (flow cell 2) of a sensor chip surface through amine coupling chemistry (by modification of carboxymethyl groups with mixture of NHS/EDC) such that about 1000 response units (RU) of receptor was immobilized on the surface. Following this, the unreacted active esters were "capped off" with an injection of 1M Et-NH2. Once a suitable surface was prepared, ch4D5-FcWT (wild-type Fc), ch4D5, and trastuzumab (control) were injected at concentrations of 6.25-200 nM over the surface at a flow rate of 70 mL/min for 180 sec.

Once an entire data set was collected, the resulting binding curves were globally fitted and the rate constants and apparent equilibrium binding constant were calculated using computer algorithms supplied by the manufacturer, as described in the BIAevaluation Software Handbook available from BIAcore, Inc. FIG. 3 shows the graphical results of the SPR analysis, and the calculated constants are provided in Table 5.

TABLE 5

Kinetic and Equilibrium Constants Calculated from BIAcore Data

| Analyte | Ka1 (1/mole * s) | Kd1 (1/s) | $K_D$ (nm) |
|---|---|---|---|
| ch4D5-wild-type Fc | $1.7 \times 10^5$ | $\sim 3.2 \times 10^{-7}$ (est.) | — |
| ch4D5 | $1.1 \times 10^5$ | $\sim 6.3 \times 10^{-6}$ (est.) | — |
| trastuzumab | $1.6 \times 10^5$ | $1.3 \times 10^{-4}$ | 0.8 |

Example 2

Apoptosis

Various cell lines were incubated overnight with ch4D5 and ch4D5-FcMT1. Apoptosis was assayed by FACS analysis, and results are shown in Table 6.

TABLE 6

| Cell Lines | Experiment 1 | | Experiment 2 | |
|---|---|---|---|---|
| | ch4D5 | ch4D5 FcMT1 | ch4D5 | ch4D5 FcMT1 |
| SKBR3 | 35% | 30% | 15% | 10% |
| JIMT | 10% | 10% | 12-30% | 10-30% |
| BT474 | 0 | 0 | 0 | 0 |
| MCF-7 | 0 | 0 | 0 | 0 |
| MDA MB 435 | 0 | 0 | 0 | 0 |
| MDA MB 468 | 10% | 10% | 5% | 0 |
| MDA MB 361 | 0 | 0 | 12% | 10% |
| MDA MB 453 | 20% | 20% | 20% | 20% |
| MDA MB 231 | 0 | 0 | 0 | 0 |
| ZR-75-1 | 0 | 0 | 0 | 0 |
| A549 | 0 | 0 | 0 | 0 |
| SKOV3 | 0 | 0 | 0 | 0 |
| HT-29 | 0 | 0 | 0 | 0 |
| OVCAR-3 | 10% | 14% | 5% | 19% |
| OVCAR-8 | 0 | 0 | 0 | 0 |
| BT-20 | 12% | 10% | 20% | 15% |

Example 3

Proliferation

[$^3$H]Thymidine ([$^3$H]TdR) incorporation into DNA was used as a biochemical index of SKBR3 cell proliferation, to compare the effects of various chimeric 4D5 antibodies of the present embodiments. The effect of ch4D5-Ag, ch4D5, and Ch4D-FcMT1 on CD16-158F+ and CD16-158V+ cells were studied and compared to controls. Results are depicted in FIG. 4.

Example 4

Anti-Tumor Activity in Mice (Breast Cancer Model)

Figure 5:
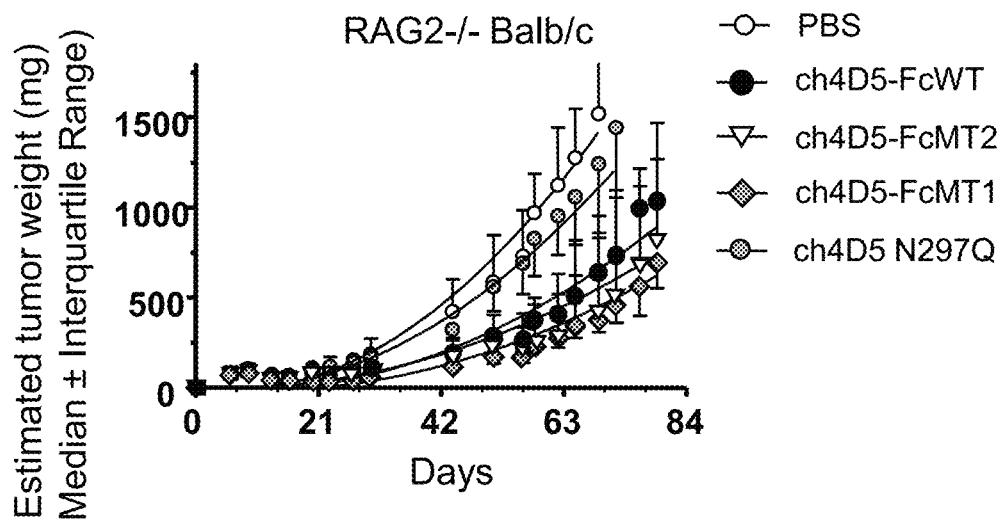
FIG. 5 depicts the enhanced anti-tumor activity of various antibodies of the present embodiments in non-transgenic mice.
Figure 6:
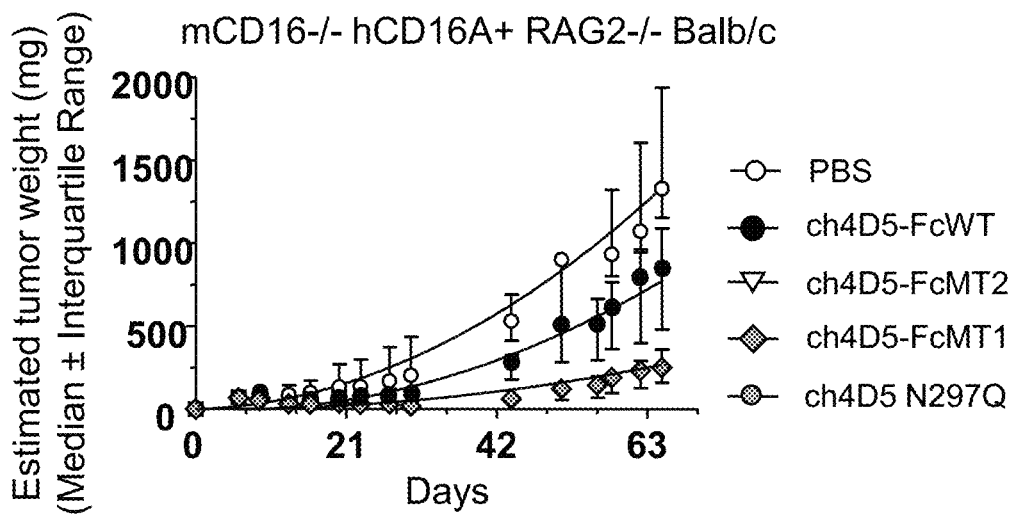
FIG. 6 depicts the enhanced anti-tumor activity of various antibodies of the present embodiments in hCD16A transgenic mice.

Anti-tumor activity of various antibodies was studied in a breast cancer model using non-transgenic and transgenic (hCD16A) mice. Fifty Balb/c RAG2−/− non-transgenic mice from MacroGenics breeding colony were injected s.c. at day 0 with JMT-1 breast cancer cells. Mice were divided into five groups of 10 mice each, and treated intraperitoneously (IP) weekly for 8 weeks with ch4D5 N297Q, ch4D5- wild-type Fc, ch4D5-FcMT1, ch4D5-FcMT2, or PBS (negative control). Tumor development is monitored twice per week, using calipers, and tumor weight is estimated by the following formula: tumor weight=(length×width$^2$)/2. Results are shown in FIG. 5. Twenty-three Balb/c RAG2−/− mCD16−/− hCD16A+ transgenic mice from MacroGenics breeding colony were injected s.c. at day 0 with JIMT-1 breast cancer cells. Mice were divided into three groups, and treated intraperitoneally (IP) weekly for 8 weeks with ch4D5-wild-type Fc (n=8), ch4D5-FcMT1 (n=8), or PBS (negative control; n=7). Tumor development is monitored twice per week, using calipers, and tumor weight is estimated by the following formula: tumor weight=(length×width$^2$)/2. Results are shown in FIG. 6.

Example 5

Anti-Tumor Activity in Mice (Ovarian Cancer Model)

Figure 7:
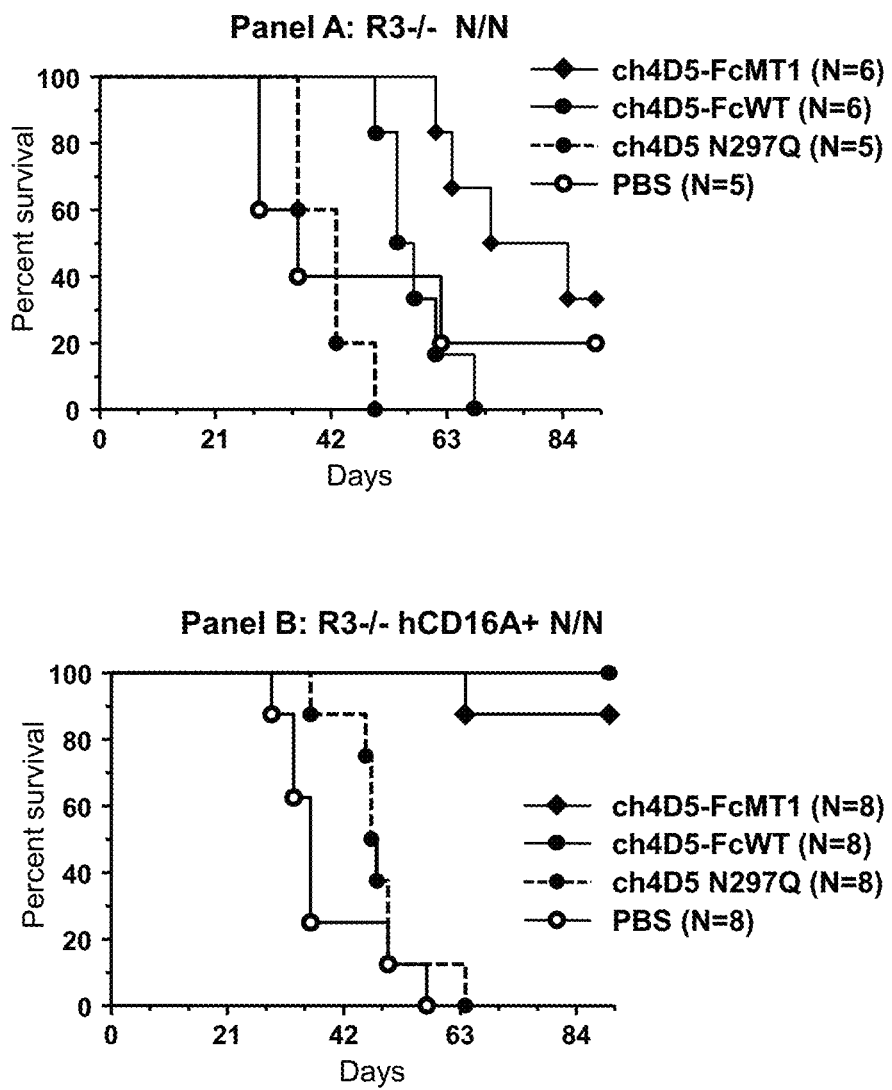
FIG. 7 depicts the role of mFcRIV and hCD16A in tumor growth inhibition by various antibodies of the present embodiments in non-transgenic and transgenic mice.
Figure 8:
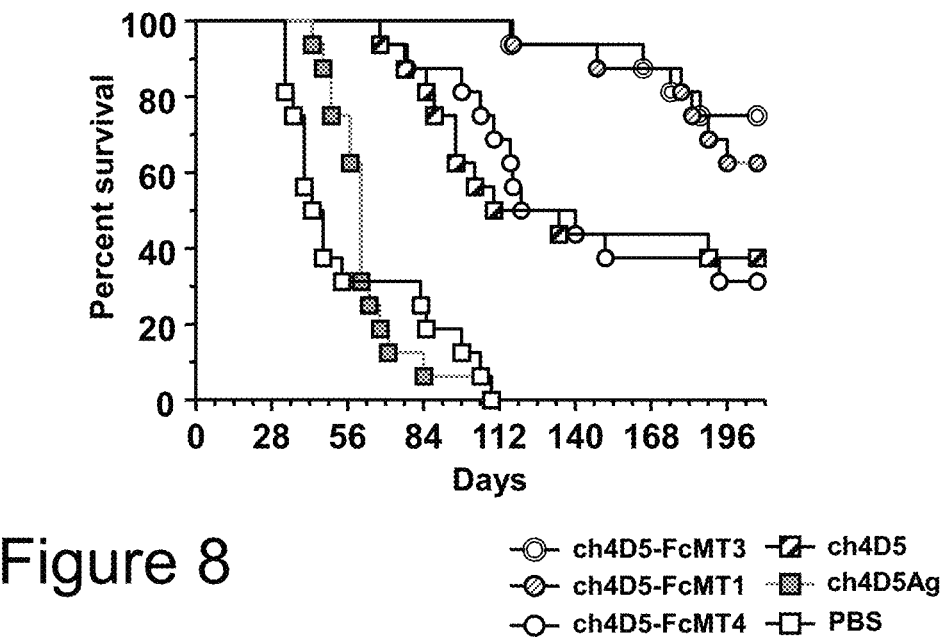
FIG. 8 depicts the enhanced anti-tumor activity of various antibodies of the present embodiments in hCD16A transgenic mice.

Anti-tumor activity of various antibodies was studied in an ovarian cancer model using non-transgenic and transgenic (hCD16A) mice. 22 R3−/− N/N non-transgenic mice from MacroGenics breeding colony were injected s.c. at day 0 with SKOV-3 ovarian cancer cells. Mice were divided into four groups, and treated intraperitoneally (IP) weekly for 8 weeks with ch4D5 N297Q (n=5), ch4D5-wild-type Fc (n=6), ch4D5-FcMT1 (n=6), or PBS (negative control; n=5). Tumor development is monitored twice per week, using calipers, and tumor weight is estimated by the following formula: tumor weight=(length×width$^2$)/2. Results are shown in FIG. 7, Panel A. 32 R3−/− N/N hCD16A+ transgenic mice from MacroGenics breeding colony were injected s.c. at day 0 with SKOV-3 ovarian cancer cells. Mice were divided into four groups, and treated intraperitoneally (IP) weekly for 8 weeks with ch4D5 N297Q (n=8), ch4D5-wild-type Fc (n=8), ch4D5-FcMT1 (n=8), or PBS (negative control; n=8). Tumor development is monitored twice per week, using calipers, and tumor weight is estimated by the following formula: tumor weight=(length×width$^2$)/2. Results are shown in FIG. 7, Panel B. 96 mCD16−/− huCD16A FoxN1−/− (nu/nu) transgenic mice from MacroGenics breeding colony were injected s.c. at day 0 with SKOV-3 ovarian cancer cells. Mice were divided into six groups of 16 mice each, and treated intraperitoneally (IP) weekly for 8 weeks with ch4D5-FcMT3, ch4D5-FcMT1, ch4D5-FcMT4, ch4D5, ch4D5Ag, or PBS (negative control). Tumor development is monitored twice per week, using calipers, and tumor weight is estimated by the following formula: tumor weight=(length×width$^2$)/2. Results are shown in FIG. 8.

Example 6

ADCC Assays in Various Cancer Cell Lines

Figure 9:
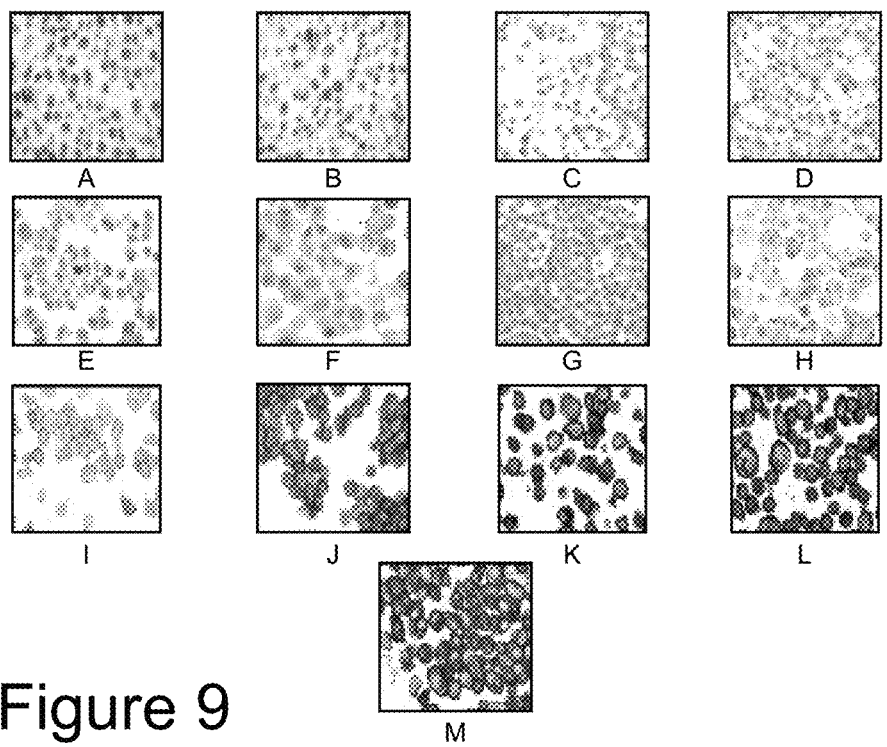
FIG. 9 illustrates representative immunohistochemical staining of cells from various cancer cell lines for HER2/neu. The various panels represent the different cell lines, i.e., Panel A: MDA-MB-435; Panel B: MDA-MB-231; Panel C: A549; Panel D: OVCAR-8; Panel E: MCF-7; Panel F: BT-20; Panel G: HT-29; Panel H: ZR75-1; Panel I: JIMT-1; Panel J: MDA-MB-453; Panel K: BT-474; Panel L: SKBR-3; and Panel M: mSKOV-3.
Figure 11:
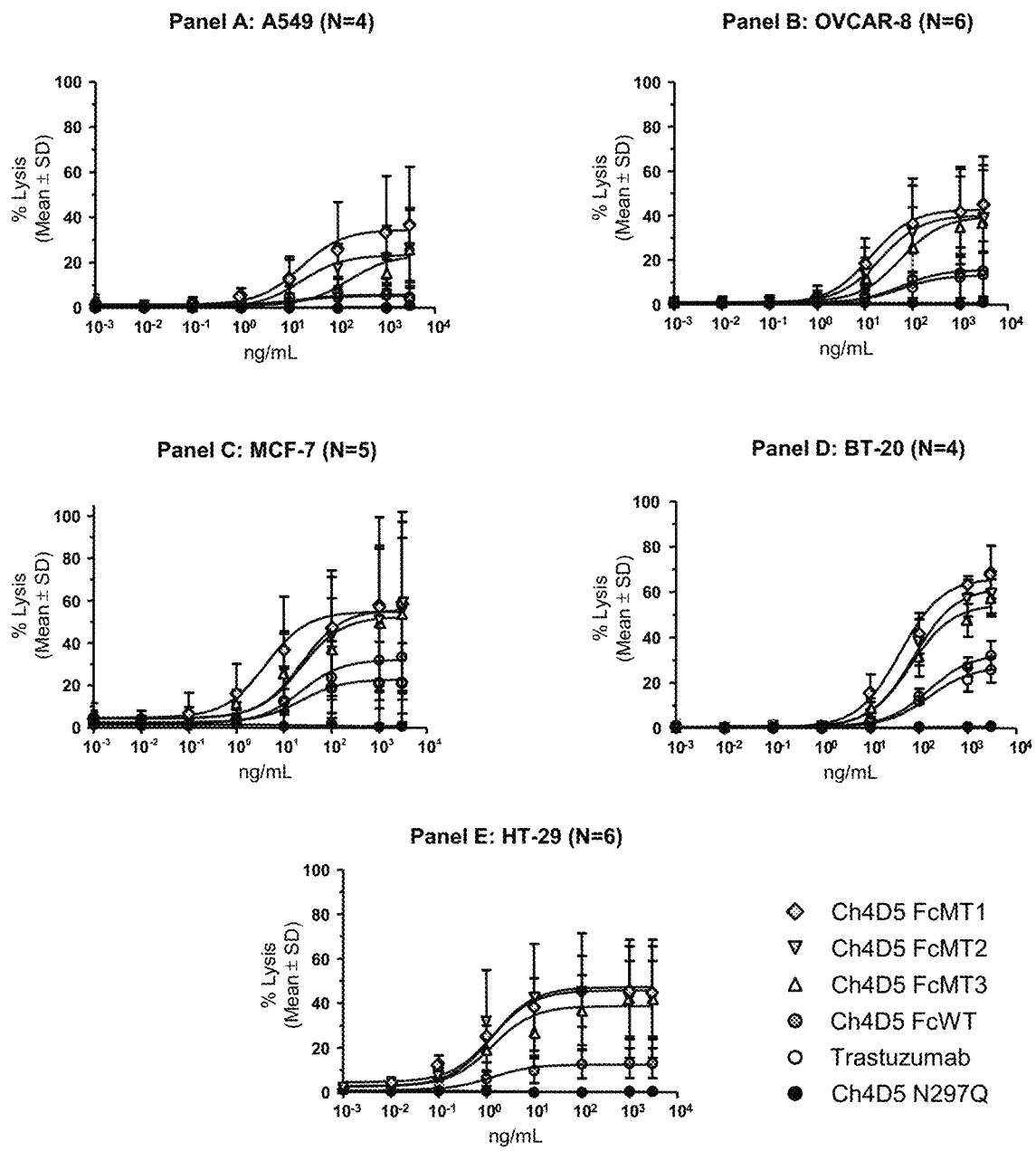
FIG. 11 depicts the results of ADCC assays performed to test the ability of various ch4D5 antibodies of the present embodiments to mediate ADCC in cancer cell lines (A549 in Panel A; OVCAR-8 in Panel B; MCF-7 in Panel C; BT-20 in Panel D; HT-29 in Panel E) having low HER2/neu expression levels (DAKO score of 1+).
Figure 13:
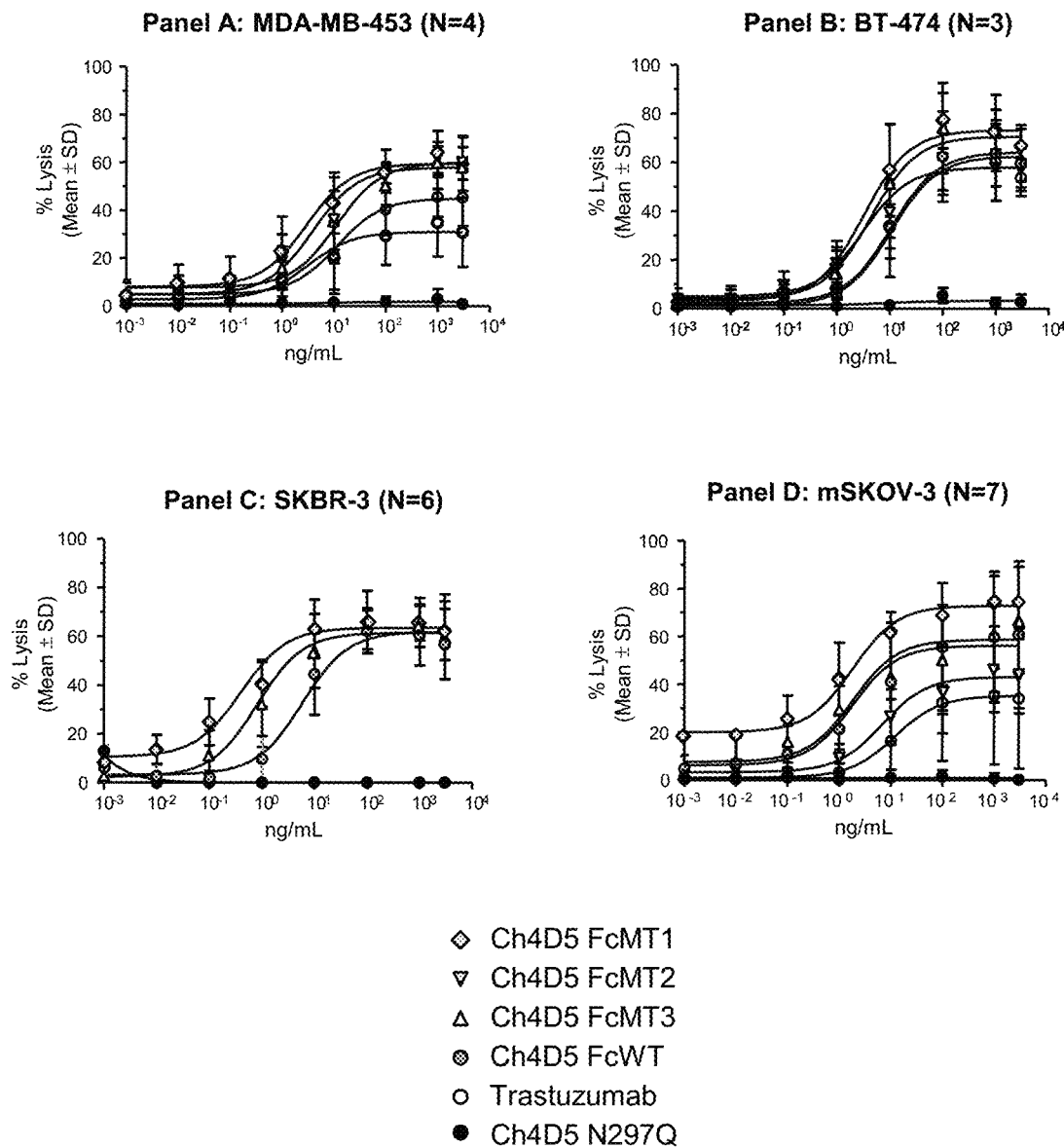
FIG. 13 depicts the results of ADCC assays performed to test the ability of various ch4D5 antibodies of the present embodiments to mediate ADCC in cancer cell lines (MDA-MB-453 in Panel A; BT-474 in Panel B; SKBR-3 in Panel C; mSKOV-3 in Panel D) having high HER2/neu expression levels (DAKO score of 3+).

FIG. 9 illustrates representative immunohistochemical staining of various cancer cell lines for HER2/neu. Cell lines were ranked according to their HER2/neu staining intensity as specified in the HER2/neu test kit sold as DAKO HerceptTest™ (DakoCytomation, Glostrup, Denmark): missing HER2/neu staining (DAKO score 0); weak HER2/neu staining (DAKO score 1+); moderate HER2/neu staining (DAKO score 2+); and strong HER2/neu staining (DAKO score 3+). The various panels represent the various cell lines, as shown in Table 7.

TABLE 7

DAKO Staining of Various Cancer Cell Lines in FIG. 9

| Panel | Cell Line | Description | Sites/Cell | Score |
|---|---|---|---|---|
| A | MDA-MB-435 | Breast carcinoma | 4.7 × 10$^3$ | 0 |
| B | MDA-MB-231 | Breast adenocarcinoma | 1.6 × 10$^4$ | 0 |
| C | A549 | Lung adenocarcinoma | 3.4 × 10$^4$ | 1+ |
| D | OVCAR-8 | Ovarian carcinoma | 4.4 × 10$^4$ | 1+ |
| E | MCF-7 | Breast adenocarcinoma | 4.5 × 10$^4$ | 1+ |
| F | BT-20 | Ductal carcinoma | 6.9 × 10$^4$ | 1+ |
| G | HT-29 | Colon/Colorectal cancer | 9.4 × 10$^4$ | 1+ |
| H | ZR75-1 | Ductal carcinoma | 1.4 × 10$^5$ | 2+ |
| I | JIMT-1 | Breast carcinoma | 2.0 × 10$^5$ | 2+ |
| J | MDA-MB-453 | Breast carcinoma | 2.8 × 10$^5$ | 3+ |
| K | BT-474 | Ductal carcinoma | 2.0 × 10$^6$ | 3+ |
| L | SKBR-3 | Breast carcinoma | 3.0 × 10$^6$ | 3+ |
| M | mSKOV-3 | Ovarian cancer | 4.0 × 10$^6$ | 3+ |

Several ch4D5 antibodies including ch4D5 antibodies having Fc variant domains were tested for the ability to mediate ADCC in the cancer cell lines, including ch4D5-FcMT1, ch4D5-FcMT2, ch4D5-FcMT3, ch4D5-FcWT (wild-type Fc), ch4D5 N297Q and trastuzumab (as a control). Data from valid assays (SR 20% MR, AICC 50% MR) is reported in Table 8, where EC$_{50}$ estimates were considered valid only if the model fit a max lysis of >20%. Comparison of EC$_{50}$ and max lysis parameters was performed by asking whether the best fit values obtained for the Fc-optimized antibodies were statistically different from those obtained for the Fc wild-type ch4D5 antibody by the sum-of-squares F test. Data were also fitted to sigmoidal dose-response models as shown in FIGS. 10-13.

TABLE 8

ADCC Assays in Various Cell Lines

| Cell Line | Antibody | EC50 (ng/mL) | p | Max Lysis (%) | p | FIG. (Panel) |
|---|---|---|---|---|---|---|
| MDA-MB-435 | ch4D5-FcMT1 | ND | — | 5 | NS | 10 (A) |
| | ch4D5-FcMT2 | ND | — | 13 | NS | |
| | ch4D5-FcMT3 | ND | — | 7 | NS | |
| | ch4D5-FcWT | ND | — | 7 | — | |
| | trastuzumab | ND | — | 7 | NS | |
| MDA-MB-231 | ch4D5-FcMT1 | 4 | NS | 27 | NS | 10 (B) |
| | ch4D5-FcMT2 | 12 | NS | 29 | NS | |
| | ch4D5-FcMT3 | ? | ? | 24 | NS | |
| | ch4D5-FcWT | 9 | — | 27 | — | |
| | trastuzumab | 7 | NS | 22 | NS | |
| A549 | ch4D5-FcMT1 | 14 | — | 34 | <0.01 | 11 (A) |
| | ch4D5-FcMT2 | 21 | — | 24 | <0.01 | |
| | ch4D5-FcMT3 | >100 | — | 23 | <0.01 | |
| | ch4D5-FcWT | ND | — | 6 | — | |
| | trastuzumab | ND | — | 5 | NS | |
| OVCAR-8 | ch4D5-FcMT1 | 14 | <0.01 | 43 | <0.01 | 11 (B) |
| | ch4D5-FcMT2 | 21 | <0.05 | 40 | <0.01 | |
| | ch4D5-FcMT3 | 26 | NS | 36 | <0.01 | |
| | ch4D5-FcWT | 57 | — | 16 | — | |
| | trastuzumab | 37 | NS | 13 | NS | |
| MCF-7 | ch4D5-FcMT1 | 4 | <0.05 | 55 | <0.01 | 11 (C) |
| | ch4D5-FcMT2 | 9 | NS | 51 | <0.01 | |
| | ch4D5-FcMT3 | 8 | NS | 48 | <0.01 | |
| | ch4D5-FcWT | 23 | NS | 32 | — | |
| | trastuzumab | 9 | — | 21 | NS | |
| BT-20 | ch4D5-FcMT1 | 42 | <0.01 | 66 | <0.01 | 11 (D) |
| | ch4D5-FcMT2 | 78 | <0.01 | 62 | <0.01 | |
| | ch4D5-FcMT3 | 67 | <0.01 | 55 | <0.01 | |
| | ch4D5-FcWT | >100 | — | 33 | — | |
| | trastuzumab | >100 | NS | 25 | NS | |
| HT-29 | ch4D5-FcMT1 | 0.4 | — | 43 | <0.01 | 11 (E) |
| | ch4D5-FcMT2 | 0.5 | — | 44 | <0.01 | |
| | ch4D5-FcMT3 | 1 | — | 38 | <0.01 | |
| | ch4D5-FcWT | ND | — | 13 | — | |

TABLE 8-continued

ADCC Assays in Various Cell Lines

| Cell Line | Antibody | EC50 (ng/mL) | p | Max Lysis (%) | p | FIG. (Panel) |
|---|---|---|---|---|---|---|
| ZR75-1 | ch4D5-FcMT1 | 14 | <0.01 | 78 | <0.01 | 12 (A) |
| | ch4D5-FcMT2 | 20 | NS | 67 | <0.01 | |
| | ch4D5-FcMT3 | 26 | <0.01 | 63 | <0.01 | |
| | ch4D5-FcWT | 38 | — | 38 | — | |
| | trastuzumab | ND | — | 23 | <0.01 | |
| JIMT-1 | ch4D5-FcMT1 | 8 | NS | 73 | <0.01 | 12 (B) |
| | ch4D5-FcMT2 | 7 | <0.05 | 70 | <0.01 | |
| | ch4D5-FcMT3 | 10 | NS | 65 | <0.01 | |
| | ch4D5-FcWT | 22 | — | 43 | — | |
| | trastuzumab | 10 | NS | 34 | NS | |
| MDA-MB-453 | ch4D5-FcMT1 | 3 | <0.05 | 59 | <0.01 | 13 (A) |
| | ch4D5-FcMT2 | 4 | <0.05 | 58 | <0.01 | |
| | ch4D5-FcMT3 | 6 | NS | 57 | <0.01 | |
| | ch4D5-FcWT | 11 | — | 45 | — | |
| | trastuzumab | 3 | <0.05 | 31 | <0.01 | |
| BT-474 | ch4D5-FcMT1 | 3 | <0.01 | 73 | <0.01 | 13 (B) |
| | ch4D5-FcMT2 | 3 | <0.05 | 58 | NS | |
| | ch4D5-FcMT3 | 4 | <0.05 | 71 | NS | |
| | ch4D5-FcWT | 11 | — | 64 | — | |
| | trastuzumab | 7 | NS | 60 | NS | |
| SKBR-3 | ch4D5-FcMT1 | 0.4 | <0.01 | 64 | NS | 13 (C) |
| | ch4D5-FcMT3 | 0.8 | <0.01 | 61 | NS | |
| | ch4D5-FcWT | 6 | — | 62 | — | |
| mSKOV-3 | ch4D5-FcMT1 | 1.2 | NS | 71 | <0.01 | 13 (D) |
| | ch4D5-FcMT2 | 7 | <0.05 | 43 | <0.05 | |
| | ch4D5-FcMT3 | 0.9 | <0.05 | 56 | NS | |
| | ch4D5-FcWT | 3 | — | 58 | — | |

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method of treating a HER2/neu-expressing cancer in a patient in need thereof having a CD16A Fc Receptor comprising a Phe at position 158, comprising administering to said patient a therapeutically effective amount of an antibody that binds human HER2/neu and comprises:
   (A) an immunoglobulin light chain comprising an amino acid sequence of SEQ ID NO: 2; and
   (B) an immunoglobulin heavy chain comprising an amino acid sequence of SEQ ID NO: 9, SEQ ID NO: 11, or SEQ ID NO: 13.

2. The method of claim 1, wherein said antibody is administered by intravenous infusion.

3. The method of claim 1, comprising the further step of administering a second therapeutic agent simultaneously or sequentially with said antibody.

4. The method of claim 3, wherein said second therapeutic agent and said antibody are administered no more than 12 hours apart, or no more than 24 hours apart, or no more than 96 hours apart.

5. The method of claim 3, wherein said second therapeutic agent is selected from the group consisting of an anti-angiogenic agent, an anti-neoplastic agent, a chemotherapeutic agent, and a cytotoxic agent.

6. The method of claim 3, wherein said second therapeutic agent is selected from the group consisting of an anti-mitotic agent, a hormone therapy agent, and an aromatase inhibitor.

7. The method of claim 1, wherein said antibody comprises an immunoglobulin heavy chain comprising an amino acid sequence of SEQ ID NO: 11.

8. The method of claim 2, wherein said antibody comprises an immunoglobulin heavy chain comprising an amino acid sequence of SEQ ID NO: 11.

9. The method of claim 3, wherein said antibody comprises an immunoglobulin heavy chain comprising an amino acid sequence of SEQ ID NO: 11.

10. The method of claim 4, wherein said antibody comprises an immunoglobulin heavy chain comprising an amino acid sequence of SEQ ID NO: 11.

11. The method of claim 5, wherein said antibody comprises an immunoglobulin heavy chain comprising an amino acid sequence of SEQ ID NO: 11.

12. The method of claim 6, wherein said antibody comprises an immunoglobulin heavy chain comprising an amino acid sequence of SEQ ID NO: 11.

13. A method of treating a HER2/neu-expressing cancer in a patient in need thereof having a CD16A Fc Receptor comprising a Phe at position 158, comprising administering to said patient a therapeutically effective amount of a pharmaceutical composition comprising an antibody that binds human HER2/neu and comprises:
   (A) an immunoglobulin light chain comprising an amino acid sequence of SEQ ID NO: 2; and
   (B) an immunoglobulin heavy chain comprising an amino acid sequence of SEQ ID NO: 9, SEQ ID NO: 11, or SEQ ID NO: 13; and
   (C) a pharmaceutically acceptable carrier and/or an excipient.

14. The method of claim 13, further comprising the steps of:
   providing said pharmaceutical composition as a sterile liquid in a hermetically sealed container; and
   extracting said pharmaceutical composition from said hermetically sealed container prior to said administering step.

15. The method of claim 14 wherein the concentration of said antibody in said sterile liquid is at least 1 mg/ml.

16. The method of claim 13, wherein said antibody comprises an immunoglobulin heavy chain comprising an amino acid sequence of SEQ ID NO: 11.

17. The method of claim 14, wherein said antibody comprises an immunoglobulin heavy chain comprising an amino acid sequence of SEQ ID NO: 11.

18. The method of claim 15, wherein said antibody comprises an immunoglobulin heavy chain comprising an amino acid sequence of SEQ ID NO: 11.

19. The method of claim 14, wherein the concentration of said antibody in said sterile liquid is at least 2.5 mg/ml.

20. The method of claim 14, wherein the concentration of said antibody in said sterile liquid is at least 5 mg/ml.

21. The method of claim 14, wherein the concentration of said antibody in said sterile liquid is at least 8 mg/ml.

22. The method of claim 14, wherein the concentration of said antibody in said sterile liquid is at least 10 mg/ml.

23. The method of claim 14, wherein the concentration of said antibody in said sterile liquid is at least 15 mg/ml.

24. The method of claim 14, wherein the concentration of said antibody in said sterile liquid is at least 25 mg/ml.

25. The method of claim 14, wherein the concentration of said antibody in said sterile liquid is at least 50 mg/ml.

26. The method of claim 14, wherein the concentration of said antibody in said sterile liquid is at least 100 mg/ml.

27. The method of claim 14, wherein the concentration of said antibody in said sterile liquid is at least 150 mg/ml.

28. The method of claim 14, wherein the concentration of said antibody in said sterile liquid is at least 200 mg/ml.

29. The method of claim 19, wherein said antibody comprises an immunoglobulin heavy chain comprising an amino acid sequence of SEQ ID NO: 11.

30. The method of claim 20, wherein said antibody comprises an immunoglobulin heavy chain comprising an amino acid sequence of SEQ ID NO: 11.

31. The method of claim 21 wherein said antibody comprises an immunoglobulin heavy chain comprising an amino acid sequence of SEQ ID NO: 11.

32. The method of claim 22, wherein said antibody comprises an immunoglobulin heavy chain comprising an amino acid sequence of SEQ ID NO: 11.

33. The method of claim 23, wherein said antibody comprises an immunoglobulin heavy chain comprising an amino acid sequence of SEQ ID NO: 11.

34. The method of claim 24, wherein said antibody comprises an immunoglobulin heavy chain comprising an amino acid sequence of SEQ ID NO: 11.

35. The method of claim 25, wherein said antibody comprises an immunoglobulin heavy chain comprising an amino acid sequence of SEQ ID NO: 11.

36. The method of claim 26, wherein said antibody comprises an immunoglobulin heavy chain comprising an amino acid sequence of SEQ ID NO: 11.

37. The method of claim 27, wherein said antibody comprises an immunoglobulin heavy chain comprising an amino acid sequence of SEQ ID NO: 11.

38. The method of claim 28, wherein said antibody comprises an immunoglobulin heavy chain comprising an amino acid sequence of SEQ ID NO: 11.

\* \* \* \* \*